United States Patent
Van Eyk et al.

(10) Patent No.: US 7,384,751 B1
(45) Date of Patent: *Jun. 10, 2008

(54) METHODS OF DIAGNOSING MUSCLE DAMAGE

(75) Inventors: Jennifer E. Van Eyk, Kingston (CA); Steven D. Iscoe, Kingston (CA); Jeremy A. Simpson, Kingston (CA)

(73) Assignee: Queen's University at Kingston, Kingston, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/115,589

(22) Filed: Jul. 15, 1998

Related U.S. Application Data

(60) Provisional application No. 60/052,697, filed on Jul. 16, 1997.

(51) Int. Cl.
 *G01N 33/53* (2006.01)
(52) U.S. Cl. .................. 435/7.1; 435/7.9; 435/7.92; 435/8; 435/21; 435/26
(58) Field of Classification Search ............... 435/7.1; 436/518 T
 See application file for complete search history.

(56) References Cited

U.S. PATENT DOCUMENTS 5,290,678 A 3/1994 Jackowski

FOREIGN PATENT DOCUMENTS

| WO | 9427156 | * 11/1994 |
| WO | WO 94/27156 A1 | 11/1994 |
| WO | WO 96/10076 | 4/1996 |
| WO | WO 96/10078 | 4/1996 |
| WO | WO 96/33415 | 10/1996 |

OTHER PUBLICATIONS

Lofberg et al. *Archives of Neurology*, vol. 52, pp. 1210-1214, 1995.*
Westfall et al. *Circulation Research*, vol. 70, pp. 302-313, 1992.*
Simpson et al. J Appl. Physiol. 2000 88: 753-760.*
Simpson et al. Clinical Chem. 2002; 48: 1112-1114.*
New York Times, Dec. 7, 2006; "Is Marathoning Too Much of a Good Thing for Your Heart?"*
Armstrong, R. B. et al., "Mechanisms of exercise-induced muscle fibre injury." *Sports Medicine*, Abstract 12: 184-207 (1991).
Barbato, R., et al., "Binding of cytosolic proteins to myofibrils in ischemic rat hearts." *Circulation Research* 78: 821-828 (1996).
Gao, W. D. et al., "Role of troponin I proteolysis in the pathogenesis of stunned myocardium." *Circulation Research* 80: 393-399 (1997).
Koller, A., et al., "Effects of prolonged strenuous endurance exercise on plasma myosin heavy chain fragments and other muscular proteins. Cycling vs running." *Journal of Sports Medicine & Physical Fitness* 38: 10-17 (1998).
Westfall, M.V., et al., "Alterations in myofibrillar function and protein profiles after complete global ischemia in rat hearts." *Circulation Research* 70: 302-313 (1992).
Collinson, P.O., et al., Measurement of Cardiac Troponins. *Ann. Clin. Biochem.* 38(Pt 5): 423-449 (2001).
Katrukha, A. G., et al., Degradation of Cardiac Troponin I: Implication for Reliable Immunodetection. *Clin. Chem.* 44 (12): 2433-2440 (1998).
Konagaya, M., et al., Increased Serum Myosin Light Chain 3 Level in Neuromuscular Diseases. *Muscle & Nerve* 10(5): 415-421 (1987).
Larue, C., et al., Immunoradiometric Assay of Myosin Heavy Chain Fragments in Plasma for Investigation of Myocardial Infarction. *Clin. Chem.* 37(1): 78-82 (1991).
Ravkilde, J., Creatine Kinase Isoenzyme MB Mass, Cardiac Troponin T, and Myosin Light Chain Isotype 1 as Serological Markers of Myocardial Injury and their Prognostic Importance in Acute Coronary Syndrome. *Dan. Med. Bull.* 45 (1): 34-50 (1998).
Shi, Q., et al., Degradation of Cardiac Troponin I in Serum Complicates Comparisons of Cardiac Troponin I Assays. *Clin. Chem.* 45 (7): 1018-1025 (1999).
Takahashi, M., et al., Use of Enzyme Immunoassay for Measurement of Skeletal Troponin-I Utilizing Isoform-Specific Monoclonal Antibodies. *Clin. Biochem.* 29 (4): 301-308 (1996).
McDonough et al., "Troponin I Degradation and Covalent Complex Formation Accompanies Myocardial Ischemia/Reperfusion Injury", Circ Res. 1999 84:9-20.
Van Eyk et al., "Breakdown and Release of Myofilament Proteins During Ischemia and Ischemia/Reperfusion in Rat Hearts-Identification of Degradation Products and Effects on the pCa-Force Relation", Circ Res. 1998 82:261-271.
U.S. Appl. No. 11/138,184, filed May 26, 2005, Van Eyk et al.

* cited by examiner

*Primary Examiner*—Elizabeth C. Kemmerer
*Assistant Examiner*—Christina Borgeest
(74) *Attorney, Agent, or Firm*—Licata & Tyrrell PC

(57) ABSTRACT

A method for assessing muscle damage in a biological sample obtained from a subject is disclosed. The method involves obtaining a biological sample from a subject being assessed for muscle damage, and evaluating the sample for the presence or absence of a myofilament protein modification product. The method can also be used to assess the extent and/or type of muscle damage in a subject by studying the profile of myofilament protein modification products detected in the sample taken from the subject. The invention further provides a method for screening for an agent which modulates the level of a myofilament protein modification product present in a biological sample or for a calcium sensitizing agent. The invention is applicable to cardiac muscle and skeletal muscle.

26 Claims, 22 Drawing Sheets

Figure . HPLC analysis of normoxic (bottom trace) and hypoxic urine (top trace) displayed at 278 nm. Some differences are noted with an asterisk. Each peak represents one or more proteins. The proteins were eluted with a 20 min isocratic wash (100 %A) followed by a linear gradient to 110 min (72% A; 28 % B) followed by another linear gradient to 120 min (20 % A; 80 %B). A-0.05% TFA in HOH; B-0.05% TFA in Acetonitrile.

Patient #1

Patient #2

Human Troponin I

```
cardiac         ADGSSDAARE  PRPAPAPIRR  RSSNYRAYAT  EPHAKKKSKI  SASRKLQLKT
slow skeletal   ..........  ..........  ..........  .PEVERKPKI  TASRKLLLKS
fast skeletal   ..........  ..........  ..........  .GDEEKRNRA  ITARRQHLKS cardiac         LLLQIAKQEL  EREAEERRGE  KGRALSTRCQ  PLELAGLGFA  ELQDLCRQLH
slow skeletal   LMLAKAKECW  EQEHEEREAE  KVRYLAERIP  TLQTRGLSLS  ALQDLCRELH
fast skeletal   VMLQIAATEL  EKEESRREAE  KQNYLAEHCP  PLHIPG.SMS  EVQELCKQLH cardiac         ARVDKVDEER  YDIEAKVTKN  ITEIADLTQK  IFDLRGKFKR  PTLRRVRISA
slow skeletal   AKVEVVDEER  YDIEAKCLHN  TREIKDLKLK  VMDLRGKFKR  PPLRRVRVSA
fast skeletal   AKIDAAEEEK  YDMEVRVQKT  SKELEDMNQK  LFDLRGKFKR  PPLRRVRMSA cardiac         DAMMQALLGA  RAKESLDLRA  HLKQVKKEDT  EKEN...REV  GDWRKNIDAL
slow skeletal   DAMLRALLGS  KHKVSMDLRA  NLKSVKKEDT  EKER..PVEV  GDWRKNVEAM
fast skeletal   DAMLKALLGS  KHKVCMDLRA  NLKQVKKEDT  EKERDL.RDV  GDWRKNIEEK cardiac         SGMEGRKKKF  ES.......
slow skeletal   SGMEGRKKMF  DAAKSPTSQ
fast skeletal   SGMEGRKKMF  ESES.....
```

1. Cardiac......209 amino acids.....(P19429 - swiss prot identification number)
   VALLINS W.J., et. al.
   *FEBS LETT.* 270:57-61, 1990.
2. slow...........186 amino acids....(P19237 - swiss prot identification number)
   WADE R., et. al.
   *GENOMICS* 7:346-357, 1990.
3. fast............181 amino acids....(P48788 - swiss prot identification number)
   ZHU L., et. al.
   *BIOCHIM. BIOPHYS. ACTA* 1217:338-340, 1994.

```
Sequences (1:2) Aligned. Score:  60
Sequences (1:3) Aligned. Score:  54
Sequences (2:3) Aligned. Score:  56
```

FIGURE 17A

Rat Troponin I

```
Human Cardiac    ADGSSDAARE  PRPAPAPIRR  RS.SNYRAYA  TEPHAKKKSK  ISASRKLQLK
Rat Cardiac      ADESSDAAGE  PQPAPAPVRR  RSSANYRAYA  TEPHAKKKSK  ISASRKLQLK
Rat Slow         ..........  ..........  ..........  ..PEVERKSK  ITASRKLMLK
Rat Fast         ..........  ..........  ..........  ..GDEEKRNR  AITARRQHLK Human Cardiac    TLLLQIAKQE  LEREAEERRG  EKGRALSTRC  QPLELAGLGF  AELQDLCRQL
Rat Cardiac      TLMLQIAKQE  MEREAEERRG  EKGRVLSTRC  QPLVLDGLGF  EELQDLCRQL
Rat Slow         SLMLAKAKEC  WEQEHEEREA  EKVRYLSERI  PTLQTRGLSL  SALQDLCREL
Rat Fast         SVMLQIAATE  LEKEESRRES  EKQNYLSEHC  PPLHIPGS.M  SEVQELCKQL Human Cardiac    HARVDKVDEE  RYDIEAKVTK  NITEIADLTQ  KIFDLRGKFK  RPTLRRVRIS
Rat Cardiac      HARVDKVDEE  RYDVEAKVTK  NITEIADLTQ  KIYDLRGKFK  RPTLRRVRIS
Rat Slow         HAKVEVVDEE  RYDIEAKCLH  NTREIKDLKL  KVLDLRGKFK  RPPLRRVRVS
Rat Fast         HAKIDAAEEE  KYDMEVKVQK  SSKELEDMNQ  KLFDLRGKFK  RPPLRRVRMS Human Cardiac    ADAMMQALLG  ARAKESLDLR  AHLKQVKKED  TEKEN...RE  VGDWRKNIDA
Rat Cardiac      ADAMMQALLG  TRAKESLDLR  AHLKQVKKED  IEKEN...RE  VGDWRKNIDA
Rat Slow         ADAMLRALLG  SKHKVSMDLR  ANLKSVKKED  TEKER..PVE  VGDWRKNVEA
Rat Fast         ADAMLKALLG  SKHKVCMDLR  ANLKQVKKED  TEKERDL.RD  VGDWRKNIEE Human Cardiac    LSGMEGRKKK  FES.......
Rat Cardiac      LSGMEGRKKK  FEG.......
Rat Slow         MSGMEGRKKM  FDAAKSPTLQ
Rat Fast         KSGMEGRKKM  FESES.....
```

1. Human cardiac TnI....209 amino acids ( P19429 - swiss prot identification number)
    VALLINS W.J., et. al.
    *FEBS LETT.* 270:57-61,1990.
2. Rat Cardiac TnI.........210 amino acids ( P23693 - swiss prot identification number)
    MURPHY A.M., et al.
    *BIOCHEMISTRY* 30:707-712, 1991.
3. Rat slow TnI.............186 amino acids ( P13413 - swiss prot identification number)
    KOPPE R.I., et. al.
    *J. BIOL. CHEM.* 264:14327-14333, 1989.
4. Rat fast TnI...............181 amino acids ( P27768 - swiss prot identification number)
    GRAVEL M., HASTINGS K.E.;
    SUBMITTED (XXX-1991) TO EMBL/GENBANK/DDBJ DATA BANKS.

Sequences (1:2) Aligned. Score: 92
Sequences (1:3) Aligned. Score: 61
Sequences (1:4) Aligned. Score: 55
Sequences (2:3) Aligned. Score: 60
Sequences (2:4) Aligned. Score: 54
Sequences (3:4) Aligned. Score: 56

FIGURE 17B

Human Troponin T

```
Cardiac         SDIEEVVEEY  EEEEQEEAAV  EEQEEAAEED  AEAEAETEET  RAEEDEEEEE
Slow skeletal   SDTEE..QEY  EEEQPEEEAA  EE.....EEE  APEE..PEP.  VAE.......
fast skeletal   SD.EE.VEQV  EEQYEEEEEA  QE.....EEE  VQED..TAEE  DAE.......

Cardiac         AKEAEDGPME  ESKPKP.RSF  MPNLVPPKIP  DGERVDFDDI  HRKRMEKDLN
Slow skeletal   .......PEE  E.RPKPSRPV  VPPLIPPKIP  EGERVDFDDI  HRKRMEKDLL
fast skeletal   ........EE  K..PRP....  ..KLTAPKIP  EGEKVDFDDI  QKKRQNKDLM Cardiac         ELQALIEAHF  ENRKKEEEEL  VSLKDRIERR  RAERAEQQRI  RNEREKERQN
Slow skeletal   ELQTLIDVHF  EQRKKEEEEL  VALKERIERR  RSERAEQQRF  RTEKERERQA
fast skeletal   ELQALIDSHF  EARKKEEEEL  VALKERIEKR  RAERAEQQRI  RAEKERERQN Cardiac         RLAEERARRE  EEENRRKAED  EARKKKALSN  M.MHFGGYIQ  KQAQTERKSG
Slow skeletal   KLAEEKMRKE  EEEAKKRAED  DAKKKKVLSN  MGAHFGGYLV  KAEQK.R..G
fast skeletal   RLAEEKARRE  EEDAKRRAED  DLKKKKALSS  MGANYSSYLA  KADQK.R..G Cardiac         KRQTEREKKK  KILAERRKVL  AIDHLNEDQL  R.........  .......EKA
Slow skeletal   KRQTGREMKV  RILSERKKPL  DIDYMGEEQL  RARSAWLPPS  QPSCPAREKA
fast skeletal   KKQTAREMKK  KILAERRKPL  NIDHLGEDKL  R.........  .......DKA Cardiac         KELWQSIYNL  EAEKFDLQEK  FKQQKYEINV  LRNRINDNQK  VSKTRG...K
Slow skeletal   QELSDWIHQL  ESEKFDLMAK  LKQQKYEINV  LYNRISHAQK  FRKGAG...K
fast skeletal   KELWETLHQL  EIDKFEFGEK  LKRQKYDITT  LRSRIDQAQK  HSKKAGTPAK Cardiac         AKVTGRWK
Slow skeletal   GRVGGRWK
fast skeletal   GKVGGRWK
```

Consensus length = 308

1. Cardiac......287 amino acids.....(P45379 - swiss prot identification number)
   MESNARD L., et. al.
   *FEBS LETT.* 328:139-144, 1993.
2. slow..........277 amino acids.....(P13805 - swiss prot identification number)
   GAHLMANN R., et. al.
   *J. BIOL. CHEM.* 262:16122-16126, 1987.
3. fast............257 amino acids.....(P45378 - swiss prot identification number)
   WU Q.-L., et. al.
   *DNA CELL BIOL.* 13:217-233, 1994.

```
Sequences (1:2) Aligned. Score: 58
Sequences (1:3) Aligned. Score: 61
Sequences (2:3) Aligned. Score: 63
```

FIGURE 17C

Rat Troponin T

```
Human Cardiac    SDIEEVVEEY  EEEEQEE...  ........AA  VEEQEEAAEE  DAEAEAETEE
Rat Cardiac      SDAEEEVVEY  EEEQEEEDWS  EEEEDEQEEA  VEEEDGEAEP  DPEGEAEAEE
Rat Fast sk      ..SDEETEQV  EEQYEEE...  ..........E  E......AQ.  ........EEE Human Cardiac    TRAEEDEEEE  EAKEAEDGPM  EESKPKP.RS  FMPNLVPPKI  PDGERVDFDD
Rat Cardiac      DKAEEVGPDE  EARDAEDGPV  EDSKPKPSRL  FMPNLVPPKI  PDGERVDFDD
Rat Fast sk      .VQEEAPEPE  EVQEEE....  ...KPRP...  ...KLTAPKI  PEGEKVDFDD Human Cardiac    IHRKRMEKDL  NELQALIEAH  FENRKKEEEE  LVSLKDRIER  RRAERAEQQR
Rat Cardiac      IHRKRMEKDL  NELQTLIEAH  FENRKKEEEE  LISLKDRIEK  RRAERAEQQR
Rat Fast sk      IQKKRQNKDL  MELQALIDSH  FEARKKEEEE  LIALKERIEK  RRAERAEQQR Human Cardiac    IRNEREKERQ  NRLAEERARR  EEEENRRKAE  DEARKKKALS  NMMHFGGYIQ
Rat Cardiac      IRNEREKERQ  NRLAEERARR  EEEENRRKAE  DEARKKKALS  NMMHFGGYIQ
Rat Fast sk      IRAEKERERQ  NRLAEEKARR  EEEDAKRRAE  DDLKKKKALS  SMG..ANYSS Human Cardiac    KQAQTERKSG  KRQTEREKKK  KILAERRKVL  AIDHLNEDQL  REKAKELWQS
Rat Cardiac      K.AQTERKSG  KRQTEREKKK  KILAERRKVL  AIDHLNEDQL  REKAKELWQS
Rat Fast sk      YLAKADQKRG  KKQTAREMKK  KILAERRKPL  NIDHLSDDKL  RDKAKELWDT Human Cardiac    IYNLEAEKFD  LQEKFKQQKY  EINVLRNRIN  DNQKVSKTRG  ...KAKVTGR
Rat Cardiac      IHNLEAEKFD  LQEKFKQQKY  EINVLRNRIN  DNQKVSKTRG  ...KAKVTGR
Rat Fast sk      LYQLETDKFE  FGEKLKRQKY  DITTLRSRID  QAQKHSKKAG  ATAKGKVGGR Human Cardiac    WK
Rat Cardiac      WK
Rat Fast sk      WK
```

1. Human cardiac TnT....287 amino acids ( P45379 - swiss prot identification number)
   MESNARD L., et. al.
   *FEBS LETT.* 328:139-144, 1993.
2. Rat Cardiac TnT.........298 amino acids ( P50753 - swiss prot identification number)
   JIN J.-P., et. al.
   *J. BIOL. CHEM.* 264:14471-14477, 1989.
3. Rat fast TnT...............258 amino acids ( P09739 - swiss prot identification number)
   BREITBART R.E., et. al.
   *J. MOL. BIOL.* 188:313-324, 1986.

```
Sequences (1:2) Aligned. Score:  88
Sequences (1:3) Aligned. Score:  60
Sequences (2:3) Aligned. Score:  59

Consensus length = 302
```

FIGURE 17D

```
                            SEQUENCE LISTING

<160> NUMBER OF SEQ ID NOS: 50

<210> SEQ ID NO 1
<211> LENGTH: 12
<212> TYPE: PRT
<213> ORGANISM: Unknown
<220> FEATURE:
<221> NAME/KEY: PEPTIDE
<222> LOCATION: (1)..(12)
<223> OTHER INFORMATION: Myosin light chain 1
<220> FEATURE:
<221> NAME/KEY: PEPTIDE
<222> LOCATION: (1)
<223> OTHER INFORMATION: May be any amino acid.
<220> FEATURE:
<221> NAME/KEY: PEPTIDE
<222> LOCATION: (2)
<223> OTHER INFORMATION: May be any amino acid.
<220> FEATURE:
<221> NAME/KEY: PEPTIDE
<222> LOCATION: (7)
<223> OTHER INFORMATION: May be either Pro or Ala.

<400> SEQUENCE: 1

Xaa Xaa Lys Lys Pro Glu Xaa Lys Ala Asp Asp Ala
  1               5                  10

<210> SEQ ID NO 2
<211> LENGTH: 12
<212> TYPE: PRT
<213> ORGANISM: Unknown
<220> FEATURE:
<221> NAME/KEY: PEPTIDE
<222> LOCATION: (1)..(12)
<223> OTHER INFORMATION: Myosin light chain 1
<220> FEATURE:
<221> NAME/KEY: PEPTIDE
<222> LOCATION: (1)
<223> OTHER INFORMATION: May be any amino acid.
```

-continued

```
<400> SEQUENCE: 2

Xaa Pro Ala Pro Ala Ala Ala Pro Ala Ala Ala Pro
 1               5                  10

<210> SEQ ID NO 3
<211> LENGTH: 11
<212> TYPE: PRT
<213> ORGANISM: Unknown
<220> FEATURE:
<221> NAME/KEY: PEPTIDE
<222> LOCATION: (1)..(11)
<223> OTHER INFORMATION: malate dehydrogenase
<220> FEATURE:
<221> NAME/KEY: PEPTIDE
<222> LOCATION: (1)
<223> OTHER INFORMATION: May be any amino acid.
<220> FEATURE:
<221> NAME/KEY: PEPTIDE
<222> LOCATION: (8)
<223> OTHER INFORMATION: May be any amino acid.

<400> SEQUENCE: 3

Xaa Lys Val Ala Leu Gly Ala Xaa Gly Gly Ile
 1               5                  10

<210> SEQ ID NO 4
<211> LENGTH: 13
<212> TYPE: PRT
<213> ORGANISM: Unknown
<220> FEATURE:
<221> NAME/KEY: PEPTIDE
<222> LOCATION: (1)..(13)
<223> OTHER INFORMATION: ATP g synthase chain
<220> FEATURE:
<221> NAME/KEY: PEPTIDE
<222> LOCATION: (1)
<223> OTHER INFORMATION: May be any amino acid.
<220> FEATURE:
<221> NAME/KEY: PEPTIDE
<222> LOCATION: (2)
<223> OTHER INFORMATION: May be any amino acid.

<400> SEQUENCE: 4

Xaa Xaa Leu Lys Asp Ile Thr Arg Arg Leu Lys Ser Ile
 1               5                  10

<210> SEQ ID NO 5
<211> LENGTH: 10
<212> TYPE: PRT
<213> ORGANISM: Unknown
<220> FEATURE:
<221> NAME/KEY: PEPTIDE
<222> LOCATION: (1)..(10)
<223> OTHER INFORMATION: ATP synthase oligomycin conferring protein
<220> FEATURE:
<221> NAME/KEY: PEPTIDE
<222> LOCATION: (1)
<223> OTHER INFORMATION: May be any amino acid.
<220> FEATURE:
<221> NAME/KEY: PEPTIDE
<222> LOCATION: (2)
<223> OTHER INFORMATION: May be any amino acid.

<400> SEQUENCE: 5

Xaa Xaa Lys Leu Val Arg Pro Pro Val Gln
 1               5                  10

<210> SEQ ID NO 6
<211> LENGTH: 10
<212> TYPE: PRT
```

```
-continued

<213> ORGANISM: Unknown
<220> FEATURE:
<221> NAME/KEY: PEPTIDE
<222> LOCATION: (1)..(10)
<223> OTHER INFORMATION: serum albumin
<220> FEATURE:
<221> NAME/KEY: PEPTIDE
<222> LOCATION: (1)
<223> OTHER INFORMATION: May be any amino acid.

<400> SEQUENCE: 6

Xaa Ala His Lys Ser Glu Ile Ala His Arg
 1               5                  10

<210> SEQ ID NO 7
<211> LENGTH: 11
<212> TYPE: PRT
<213> ORGANISM: Unknown
<220> FEATURE:
<221> NAME/KEY: PEPTIDE
<222> LOCATION: (1)..(11)
<223> OTHER INFORMATION: triose phosphate isomerase
<220> FEATURE:
<221> NAME/KEY: PEPTIDE
<222> LOCATION: (1)
<223> OTHER INFORMATION: May be any amino acid.
<220> FEATURE:
<221> NAME/KEY: PEPTIDE
<222> LOCATION: (4)
<223> OTHER INFORMATION: May be Arg or Leu.

<400> SEQUENCE: 7

Xaa Pro Ser Xaa Lys Phe Phe Val Gly Gly Asn
 1               5                  10

<210> SEQ ID NO 8
<211> LENGTH: 209
<212> TYPE: PRT
<213> ORGANISM: Unknown
<220> FEATURE:
<221> NAME/KEY: PEPTIDE
<222> LOCATION: (1)..(209)
<223> OTHER INFORMATION: Human cardiac troponin I
<220> FEATURE:
<223> OTHER INFORMATION: Swiss prot identification number P19429
<300> PUBLICATION INFORMATION:
<303> JOURNAL: FEBS Lett.
<304> VOLUME: 270
<305> ISSUE: 1-2
<306> PAGES: 57-61
<307> DATE: 1990-09-17

<400> SEQUENCE: 8

Ala Asp Gly Ser Ser Asp Ala Ala Arg Glu Pro Arg Pro Ala Pro Ala
 1               5                  10                  15

Pro Ile Arg Arg Arg Ser Ser Asn Tyr Arg Ala Tyr Ala Thr Glu Pro
                20                  25                  30

His Ala Lys Lys Lys Ser Lys Ile Ser Ala Ser Arg Lys Leu Gln Leu
         35                  40                  45

Lys Thr Leu Leu Leu Gln Ile Ala Lys Gln Glu Leu Glu Arg Glu Ala
     50                  55                  60

Glu Glu Arg Arg Gly Glu Lys Gly Arg Ala Leu Ser Thr Arg Cys Gln
 65                  70                  75                  80

Pro Leu Glu Leu Ala Gly Leu Gly Phe Ala Glu Leu Gln Asp Leu Cys
                 85                  90                  95

Arg Gln Leu His Ala Arg Val Asp Lys Val Asp Glu Glu Arg Tyr Asp
            100                 105                 110
```

```
Ile Glu Ala Lys Val Thr Lys Asn Ile Thr Glu Ile Ala Asp Leu Thr
            115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys Lys Phe Glu
        195                 200                 205

Ser
```

<210> SEQ ID NO 9
<211> LENGTH: 186
<212> TYPE: PRT
<213> ORGANISM: Unknown
<220> FEATURE:
<221> NAME/KEY: PEPTIDE
<222> LOCATION: (1)..(186)
<223> OTHER INFORMATION: Human slow skeletal troponin I
<220> FEATURE:
<223> OTHER INFORMATION: Swiss prot identification number P19237
<300> PUBLICATION INFORMATION:
<303> JOURNAL: Genomics
<304> VOLUME: 7
<305> ISSUE: 3
<306> PAGES: 346-357
<307> DATE: Jul-1990

<400> SEQUENCE: 9

```
Pro Glu Val Glu Arg Lys Pro Lys Ile Thr Ala Ser Arg Lys Leu Leu
  1               5                  10                  15

Leu Lys Ser Leu Met Leu Ala Lys Ala Lys Glu Cys Trp Glu Gln Glu
            20                  25                  30

His Glu Glu Arg Glu Ala Glu Lys Val Arg Tyr Leu Ala Glu Arg Ile
        35                  40                  45

Pro Thr Leu Gln Thr Arg Gly Leu Ser Leu Ser Ala Leu Gln Asp Leu
    50                  55                  60

Cys Arg Glu Leu His Ala Lys Val Glu Val Asp Glu Glu Arg Tyr
 65                  70                  75                  80

Asp Ile Glu Ala Lys Cys Leu His Asn Thr Arg Glu Ile Lys Asp Leu
                85                  90                  95

Lys Leu Lys Val Met Asp Leu Arg Gly Lys Phe Lys Arg Pro Pro Leu
            100                 105                 110

Arg Arg Val Arg Val Ser Ala Asp Ala Met Leu Arg Ala Leu Leu Gly
        115                 120                 125

Ser Lys His Lys Val Ser Met Asp Leu Arg Ala Asn Leu Lys Ser Val
    130                 135                 140

Lys Lys Glu Asp Thr Glu Lys Glu Arg Pro Val Glu Val Gly Asp Trp
145                 150                 155                 160

Arg Lys Asn Val Glu Ala Met Ser Gly Met Glu Gly Arg Lys Lys Met
                165                 170                 175

Phe Asp Ala Ala Lys Ser Pro Thr Ser Gln
            180                 185
```

<210> SEQ ID NO 10
<211> LENGTH: 181

```
<212> TYPE: PRT
<213> ORGANISM: Unknown
<220> FEATURE:
<221> NAME/KEY: PEPTIDE
<222> LOCATION: (1)..(181)
<223> OTHER INFORMATION: Human fast skeletal troponin I
<220> FEATURE:
<223> OTHER INFORMATION: Swiss prot identification number P48788
<300> PUBLICATION INFORMATION:
<303> JOURNAL: Biochim. Biophys. Acta
<304> VOLUME: 1217
<306> PAGES: 338-340
<307> DATE: 1994-04-06

<400> SEQUENCE: 10

Gly Asp Glu Glu Lys Arg Asn Arg Ala Ile Thr Ala Arg Arg Gln His
 1               5                  10                  15

Leu Lys Ser Val Met Leu Gln Ile Ala Ala Thr Glu Leu Glu Lys Glu
                20                  25                  30

Glu Ser Arg Arg Glu Ala Glu Lys Gln Asn Tyr Leu Ala Glu His Cys
            35                  40                  45

Pro Pro Leu His Ile Pro Gly Ser Met Ser Glu Val Gln Glu Leu Cys
        50                  55                  60

Lys Gln Leu His Ala Lys Ile Asp Ala Ala Glu Glu Lys Tyr Asp
 65                  70                  75                  80

Met Glu Val Arg Val Gln Lys Thr Ser Lys Glu Leu Glu Asp Met Asn
                85                  90                  95

Gln Lys Leu Phe Asp Leu Arg Gly Lys Phe Lys Arg Pro Pro Leu Arg
                100                 105                 110

Arg Val Arg Met Ser Ala Asp Ala Met Leu Lys Ala Leu Leu Gly Ser
            115                 120                 125

Lys His Lys Val Cys Met Asp Leu Arg Ala Asn Leu Lys Gln Val Lys
        130                 135                 140

Lys Glu Asp Thr Glu Lys Glu Arg Asp Leu Arg Asp Val Gly Asp Trp
145                 150                 155                 160

Arg Lys Asn Ile Glu Glu Lys Ser Gly Met Glu Gly Arg Lys Lys Met
                165                 170                 175

Phe Glu Ser Glu Ser
            180

<210> SEQ ID NO 11
<211> LENGTH: 210
<212> TYPE: PRT
<213> ORGANISM: Unknown
<220> FEATURE:
<221> NAME/KEY: PEPTIDE
<222> LOCATION: (1)..(210)
<223> OTHER INFORMATION: Rat cardiac troponin I
<220> FEATURE:
<223> OTHER INFORMATION: Swiss prot identification number P23693
<300> PUBLICATION INFORMATION:
<303> JOURNAL: Biochemistry
<304> VOLUME: 30
<305> ISSUE: 3
<306> PAGES: 707-712
<307> DATE: 1991-01-22

<400> SEQUENCE: 11

Ala Asp Glu Ser Ser Asp Ala Ala Gly Glu Pro Gln Pro Ala Pro Ala
 1               5                  10                  15

Pro Val Arg Arg Arg Ser Ser Ala Asn Tyr Arg Ala Tyr Ala Thr Glu
                20                  25                  30

Pro His Ala Lys Lys Lys Ser Lys Ile Ser Ala Ser Arg Lys Leu Gln
```

-continued

```
                35                  40                  45
Leu Lys Thr Leu Met Leu Gln Ile Ala Lys Gln Glu Met Glu Arg Glu
         50                  55                  60
Ala Glu Glu Arg Arg Gly Glu Lys Gly Arg Val Leu Ser Thr Arg Cys
 65                  70                  75                  80
Gln Pro Leu Val Leu Asp Gly Leu Gly Phe Glu Glu Leu Gln Asp Leu
                 85                  90                  95
Cys Arg Gln Leu His Ala Arg Val Asp Lys Val Asp Glu Glu Arg Tyr
            100                 105                 110
Asp Val Glu Ala Lys Val Thr Lys Asn Ile Thr Glu Ile Ala Asp Leu
            115                 120                 125
Thr Gln Lys Ile Tyr Asp Leu Arg Gly Lys Phe Lys Arg Pro Thr Leu
        130                 135                 140
Arg Arg Val Arg Ile Ser Ala Asp Ala Met Met Gln Ala Leu Leu Gly
145                 150                 155                 160
Thr Arg Ala Lys Glu Ser Leu Asp Leu Arg Ala His Leu Lys Gln Val
                165                 170                 175
Lys Lys Glu Asp Ile Glu Lys Glu Asn Arg Glu Val Gly Asp Trp Arg
            180                 185                 190
Lys Asn Ile Asp Ala Leu Ser Gly Met Glu Gly Arg Lys Lys Lys Phe
        195                 200                 205
Glu Gly
    210
```

```
<210> SEQ ID NO 12
<211> LENGTH: 186
<212> TYPE: PRT
<213> ORGANISM: Unknown
<220> FEATURE:
<221> NAME/KEY: PEPTIDE
<222> LOCATION: (1)..(186)
<223> OTHER INFORMATION: Rat slow skeletal troponin I
<220> FEATURE:
<223> OTHER INFORMATION: Swiss prot identification number P13413
<300> PUBLICATION INFORMATION:
<303> JOURNAL: J. Biol. Chem.
<304> VOLUME: 264
<305> ISSUE: 24
<306> PAGES: 14327-14333
<307> DATE: 1989-08-25

<400> SEQUENCE: 12

Pro Glu Val Glu Arg Lys Ser Lys Ile Thr Ala Ser Arg Lys Leu Met
  1               5                  10                  15
Leu Lys Ser Leu Met Leu Ala Lys Ala Lys Glu Cys Trp Glu Gln Glu
             20                  25                  30
His Glu Glu Arg Glu Ala Glu Lys Val Arg Tyr Leu Ser Glu Arg Ile
         35                  40                  45
Pro Thr Leu Gln Thr Arg Gly Leu Ser Leu Ser Ala Leu Gln Asp Leu
     50                  55                  60
Cys Arg Glu Leu His Ala Lys Val Glu Val Val Asp Glu Glu Arg Tyr
 65                  70                  75                  80
Asp Ile Glu Ala Lys Cys Leu His Asn Thr Arg Glu Ile Lys Asp Leu
                 85                  90                  95
Lys Leu Lys Val Leu Asp Leu Arg Gly Lys Phe Lys Arg Pro Pro Leu
            100                 105                 110
Arg Arg Val Arg Val Ser Ala Asp Ala Met Leu Arg Ala Leu Leu Gly
        115                 120                 125
```

```
Ser Lys His Lys Val Ser Met Asp Leu Arg Ala Asn Leu Lys Ser Val
        130                 135                 140
Lys Lys Glu Asp Thr Glu Lys Glu Arg Pro Val Glu Val Gly Asp Trp
145                 150                 155                 160
Arg Lys Asn Val Glu Ala Met Ser Gly Met Glu Gly Arg Lys Lys Met
                165                 170                 175
Phe Asp Ala Ala Lys Ser Pro Thr Leu Gln
            180                 185

<210> SEQ ID NO 13
<211> LENGTH: 181
<212> TYPE: PRT
<213> ORGANISM: Unknown
<220> FEATURE:
<221> NAME/KEY: PEPTIDE
<222> LOCATION: (1)..(181)
<223> OTHER INFORMATION: Rat fast skeletal troponin I
<220> FEATURE:
<223> OTHER INFORMATION: Swiss prot identification number P27768
<300> PUBLICATION INFORMATION:
<308> DATABASE ACCESSION NUMBER: EMBL/GENBANK/DDBJ DATA BANKS
<309> DATABASE ENTRY DATE: 1992-08-01

<400> SEQUENCE: 13

Gly Asp Glu Glu Lys Arg Asn Arg Ala Ile Thr Ala Arg Arg Gln His
1               5                   10                  15
Leu Lys Ser Val Met Leu Gln Ile Ala Ala Thr Glu Leu Glu Lys Glu
                20                  25                  30
Glu Ser Arg Arg Glu Ser Glu Lys Gln Asn Tyr Leu Ser Glu His Cys
            35                  40                  45
Pro Pro Leu His Ile Pro Gly Ser Met Ser Glu Val Gln Glu Leu Cys
        50                  55                  60
Lys Gln Leu His Ala Lys Ile Asp Ala Ala Glu Glu Glu Lys Tyr Asp
65                  70                  75                  80
Met Glu Val Lys Val Gln Lys Ser Ser Lys Glu Leu Glu Asp Met Asn
                85                  90                  95
Gln Lys Leu Phe Asp Leu Arg Gly Lys Phe Lys Arg Pro Pro Leu Arg
            100                 105                 110
Arg Val Arg Met Ser Ala Asp Ala Met Leu Lys Ala Leu Leu Gly Ser
        115                 120                 125
Lys His Lys Val Cys Met Asp Leu Arg Ala Asn Leu Lys Gln Val Lys
130                 135                 140
Lys Glu Asp Thr Glu Lys Glu Arg Asp Leu Arg Asp Val Gly Asp Trp
145                 150                 155                 160
Arg Lys Asn Ile Glu Glu Lys Ser Gly Met Glu Gly Arg Lys Lys Met
                165                 170                 175
Phe Glu Ser Glu Ser
            180

<210> SEQ ID NO 14
<211> LENGTH: 287
<212> TYPE: PRT
<213> ORGANISM: Unknown
<220> FEATURE:
<221> NAME/KEY: PEPTIDE
<222> LOCATION: (1)..(287)
<223> OTHER INFORMATION: Human cardiac troponin T
<220> FEATURE:
<223> OTHER INFORMATION: Swiss prot identification number P45379
<300> PUBLICATION INFORMATION:
<303> JOURNAL: FEBS Lett.
<304> VOLUME: 328
```

<305> ISSUE: 1-2
<306> PAGES: 139-144
<307> DATE: 1993-08-09

<400> SEQUENCE: 14

```
Ser Asp Ile Glu Glu Val Val Glu Glu Tyr Glu Glu Glu Gln Glu
 1               5                  10                  15

Glu Ala Ala Val Glu Glu Gln Glu Glu Ala Ala Glu Glu Asp Ala Glu
            20                  25                  30

Ala Glu Ala Glu Thr Glu Glu Thr Arg Ala Glu Glu Asp Glu Glu Glu
        35                  40                  45

Glu Glu Ala Lys Glu Ala Glu Asp Gly Pro Met Glu Glu Ser Lys Pro
50                  55                  60

Lys Pro Arg Ser Phe Met Pro Asn Leu Val Pro Pro Lys Ile Pro Asp
65                  70                  75                  80

Gly Glu Arg Val Asp Phe Asp Asp Ile His Arg Lys Arg Met Glu Lys
                85                  90                  95

Asp Leu Asn Glu Leu Gln Ala Leu Ile Glu Ala His Phe Glu Asn Arg
            100                 105                 110

Lys Lys Glu Glu Glu Glu Leu Val Ser Leu Lys Asp Arg Ile Glu Arg
        115                 120                 125

Arg Arg Ala Glu Arg Ala Glu Gln Gln Arg Ile Arg Asn Glu Arg Glu
130                 135                 140

Lys Glu Arg Gln Asn Arg Leu Ala Glu Glu Arg Ala Arg Arg Glu Glu
145                 150                 155                 160

Glu Glu Asn Arg Arg Lys Ala Glu Asp Glu Ala Arg Lys Lys Lys Ala
                165                 170                 175

Leu Ser Asn Met Met His Phe Gly Gly Tyr Ile Gln Lys Gln Ala Gln
            180                 185                 190

Thr Glu Arg Lys Ser Gly Lys Arg Gln Thr Glu Arg Glu Lys Lys Lys
        195                 200                 205

Lys Ile Leu Ala Glu Arg Arg Lys Val Leu Ala Ile Asp His Leu Asn
210                 215                 220

Glu Asp Gln Leu Arg Glu Lys Ala Lys Glu Leu Trp Gln Ser Ile Tyr
225                 230                 235                 240

Asn Leu Glu Ala Glu Lys Phe Asp Leu Gln Glu Lys Phe Lys Gln Gln
                245                 250                 255

Lys Tyr Glu Ile Asn Val Leu Arg Asn Arg Ile Asn Asp Asn Gln Lys
            260                 265                 270

Val Ser Lys Thr Arg Gly Lys Ala Lys Val Thr Gly Arg Trp Lys
        275                 280                 285
```

<210> SEQ ID NO 15
<211> LENGTH: 277
<212> TYPE: PRT
<213> ORGANISM: Unknown
<220> FEATURE:
<221> NAME/KEY: PEPTIDE
<222> LOCATION: (1)..(277)
<223> OTHER INFORMATION: Human slow skeletal troponin T
<220> FEATURE:
<223> OTHER INFORMATION: Swiss prot identification number P13805
<300> PUBLICATION INFORMATION:
<303> JOURNAL: J. Biol. Chem.
<304> VOLUME: 262
<305> ISSUE: 33
<306> PAGES: 16122-16126
<307> DATE: 1987-11-25

<400> SEQUENCE: 15

```
Ser Asp Thr Glu Glu Gln Glu Tyr Glu Glu Gln Pro Glu Glu
  1               5                  10                  15

Ala Ala Glu Glu Glu Glu Ala Pro Glu Glu Pro Glu Pro Val Ala
              20                  25                  30

Glu Pro Glu Glu Glu Arg Pro Lys Pro Ser Arg Pro Val Val Pro
              35                  40                  45

Leu Ile Pro Pro Lys Ile Pro Glu Gly Glu Arg Val Asp Phe Asp
 50                  55                  60

Ile His Arg Lys Arg Met Glu Lys Asp Leu Leu Glu Leu Gln Thr Leu
 65                  70                  75                  80

Ile Asp Val His Phe Glu Gln Arg Lys Lys Glu Glu Glu Leu Val
                  85                  90                  95

Ala Leu Lys Glu Arg Ile Glu Arg Arg Arg Ser Glu Arg Ala Glu Gln
              100                 105                 110

Gln Arg Phe Arg Thr Glu Lys Glu Arg Glu Arg Gln Ala Lys Leu Ala
              115                 120                 125

Glu Glu Lys Met Arg Lys Glu Glu Glu Ala Lys Lys Arg Ala Glu
              130                 135                 140

Asp Asp Ala Lys Lys Lys Lys Val Leu Ser Asn Met Gly Ala His Phe
145                 150                 155                 160

Gly Gly Tyr Leu Val Lys Ala Glu Gln Lys Arg Gly Lys Arg Gln Thr
              165                 170                 175

Gly Arg Glu Met Lys Val Arg Ile Leu Ser Glu Arg Lys Lys Pro Leu
              180                 185                 190

Asp Ile Asp Tyr Met Gly Glu Glu Gln Leu Arg Ala Arg Ser Ala Trp
              195                 200                 205

Leu Pro Pro Ser Gln Pro Ser Cys Pro Ala Arg Glu Lys Ala Gln Glu
210                 215                 220

Leu Ser Asp Trp Ile His Gln Leu Glu Ser Glu Lys Phe Asp Leu Met
225                 230                 235                 240

Ala Lys Leu Lys Gln Gln Lys Tyr Glu Ile Asn Val Leu Tyr Asn Arg
              245                 250                 255

Ile Ser His Ala Gln Lys Phe Arg Lys Gly Ala Gly Lys Gly Arg Val
              260                 265                 270

Gly Gly Arg Trp Lys
              275
```

<210> SEQ ID NO 16
<211> LENGTH: 257
<212> TYPE: PRT
<213> ORGANISM: Unknown
<220> FEATURE:
<221> NAME/KEY: PEPTIDE
<222> LOCATION: (1)..(257)
<223> OTHER INFORMATION: Human fast skeletal troponin T
<220> FEATURE:
<223> OTHER INFORMATION: Swiss prot identification number P45378
<300> PUBLICATION INFORMATION:
<303> JOURNAL: DNA Cell Biol.
<304> VOLUME: 13
<305> ISSUE: 3
<306> PAGES: 217-233
<307> DATE: MAR-1994

<400> SEQUENCE: 16

```
Ser Asp Glu Glu Val Glu Gln Val Glu Glu Gln Tyr Glu Glu Glu
  1               5                  10                  15

Glu Ala Gln Glu Glu Glu Glu Val Gln Glu Asp Thr Ala Glu Glu Asp
```

-continued

```
                20                  25                  30
Ala Glu Glu Glu Lys Pro Arg Pro Lys Leu Thr Ala Pro Lys Ile Pro
         35                  40                  45
Glu Gly Glu Lys Val Asp Phe Asp Asp Ile Gln Lys Lys Arg Gln Asn
     50                  55                  60
Lys Asp Leu Met Glu Leu Gln Ala Leu Ile Asp Ser His Phe Glu Ala
 65                  70                  75                  80
Arg Lys Lys Glu Glu Glu Leu Val Ala Leu Lys Glu Arg Ile Glu
                 85                  90                  95
Lys Arg Arg Ala Glu Arg Ala Glu Gln Gln Arg Ile Arg Ala Glu Lys
             100                 105                 110
Glu Arg Glu Arg Gln Asn Arg Leu Ala Glu Lys Ala Arg Arg Glu
         115                 120                 125
Glu Glu Asp Ala Lys Arg Arg Ala Glu Asp Asp Leu Lys Lys Lys
     130                 135                 140
Ala Leu Ser Ser Met Gly Ala Asn Tyr Ser Ser Tyr Leu Ala Lys Ala
145                 150                 155                 160
Asp Gln Lys Arg Gly Lys Lys Gln Thr Ala Arg Glu Met Lys Lys Lys
                 165                 170                 175
Ile Leu Ala Glu Arg Arg Lys Pro Leu Asn Ile Asp His Leu Gly Glu
             180                 185                 190
Asp Lys Leu Arg Asp Lys Ala Lys Glu Leu Trp Glu Thr Leu His Gln
         195                 200                 205
Leu Glu Ile Asp Lys Phe Glu Phe Gly Glu Lys Leu Lys Arg Gln Lys
     210                 215                 220
Tyr Asp Ile Thr Thr Leu Arg Ser Arg Ile Asp Gln Ala Gln Lys His
225                 230                 235                 240
Ser Lys Lys Ala Gly Thr Pro Ala Lys Gly Lys Val Gly Gly Arg Trp
                 245                 250                 255
Lys

<210> SEQ ID NO 17
<211> LENGTH: 298
<212> TYPE: PRT
<213> ORGANISM: Unknown
<220> FEATURE:
<221> NAME/KEY: PEPTIDE
<222> LOCATION: (1)..(298)
<223> OTHER INFORMATION: Rat cardiac troponin T
<220> FEATURE:
<223> OTHER INFORMATION: Swiss prot identification number P50753
<300> PUBLICATION INFORMATION:
<303> JOURNAL: J. Biol. Chem.
<304> VOLUME: 264
<305> ISSUE: 24
<306> PAGES: 14471-14477
<307> DATE: 1989-08-25

<400> SEQUENCE: 17

Ser Asp Ala Glu Glu Glu Val Val Glu Tyr Glu Glu Glu Gln Glu Glu
  1               5                  10                  15
Glu Asp Trp Ser Glu Glu Glu Asp Glu Gln Glu Glu Ala Val Glu
                 20                  25                  30
Glu Glu Asp Gly Glu Ala Glu Pro Asp Pro Glu Gly Glu Ala Glu Ala
         35                  40                  45
Glu Glu Asp Lys Ala Glu Glu Val Gly Pro Asp Glu Glu Ala Arg Asp
     50                  55                  60
Ala Glu Asp Gly Pro Val Glu Asp Ser Lys Pro Lys Pro Ser Arg Leu
```

```
                65                  70                  75                  80
Phe Met Pro Asn Leu Val Pro Pro Lys Ile Pro Asp Gly Glu Arg Val
                    85                  90                  95

Asp Phe Asp Asp Ile His Arg Lys Arg Met Glu Lys Asp Leu Asn Glu
                100                 105                 110

Leu Gln Thr Leu Ile Glu Ala His Phe Glu Asn Arg Lys Lys Glu Glu
                115                 120                 125

Glu Glu Leu Ile Ser Leu Lys Asp Arg Ile Glu Lys Arg Arg Ala Glu
            130                 135                 140

Arg Ala Glu Gln Gln Arg Ile Arg Asn Glu Arg Glu Lys Glu Arg Gln
145                 150                 155                 160

Asn Arg Leu Ala Glu Glu Arg Ala Arg Arg Glu Glu Glu Glu Asn Arg
                165                 170                 175

Arg Lys Ala Glu Asp Glu Ala Arg Lys Lys Lys Ala Leu Ser Asn Met
                180                 185                 190

Met His Phe Gly Gly Tyr Ile Gln Lys Ala Gln Thr Glu Arg Lys Ser
                195                 200                 205

Gly Lys Arg Gln Thr Glu Arg Glu Lys Lys Lys Ile Leu Ala Glu
            210                 215                 220

Arg Arg Lys Val Leu Ala Ile Asp His Leu Asn Glu Asp Gln Leu Arg
225                 230                 235                 240

Glu Lys Ala Lys Glu Leu Trp Gln Ser Ile His Asn Leu Glu Ala Glu
                245                 250                 255

Lys Phe Asp Leu Gln Glu Lys Phe Lys Gln Lys Tyr Glu Ile Asn
                260                 265                 270

Val Leu Arg Asn Arg Ile Asn Asp Asn Gln Lys Val Ser Lys Thr Arg
                275                 280                 285

Gly Lys Ala Lys Val Thr Gly Arg Trp Lys
            290                 295
```

```
<210> SEQ ID NO 18
<211> LENGTH: 258
<212> TYPE: PRT
<213> ORGANISM: Unknown
<220> FEATURE:
<221> NAME/KEY: PEPTIDE
<222> LOCATION: (1)..(258)
<223> OTHER INFORMATION: Rat fast skeletal troponin T
<220> FEATURE:
<223> OTHER INFORMATION: Swiss prot identification number P09739
<300> PUBLICATION INFORMATION:
<303> JOURNAL: J. Mol. Biol.
<304> VOLUME: 188
<305> ISSUE: 3
<306> PAGES: 313-324
<307> DATE: 1986-04-05

<400> SEQUENCE: 18

Ser Asp Glu Glu Thr Glu Gln Val Glu Glu Tyr Glu Glu Glu Glu
1               5                   10                  15

Glu Ala Gln Glu Glu Glu Val Gln Glu Glu Ala Pro Glu Pro Glu Glu
                20                  25                  30

Val Gln Glu Glu Glu Lys Pro Arg Pro Lys Leu Thr Ala Pro Lys Ile
            35                  40                  45

Pro Glu Gly Glu Lys Val Asp Phe Asp Asp Ile Gln Lys Lys Arg Gln
        50                  55                  60

Asn Lys Asp Leu Met Glu Leu Gln Ala Leu Ile Asp Ser His Phe Glu
65              70                  75                  80
```

```
Ala Arg Lys Lys Glu Glu Glu Leu Ile Ala Leu Lys Glu Arg Ile
             85                  90                  95

Glu Lys Arg Arg Ala Glu Arg Ala Glu Gln Gln Arg Ile Arg Ala Glu
                100                 105                 110

Lys Glu Arg Glu Arg Gln Asn Arg Leu Ala Glu Lys Ala Arg Arg
            115                 120                 125

Glu Glu Glu Asp Ala Lys Arg Arg Ala Glu Asp Leu Lys Lys Lys
130                 135                 140

Lys Ala Leu Ser Ser Met Gly Ala Asn Tyr Ser Ser Tyr Leu Ala Lys
145                 150                 155                 160

Ala Asp Gln Lys Arg Gly Lys Lys Gln Thr Ala Arg Glu Met Lys Lys
                165                 170                 175

Lys Ile Leu Ala Glu Arg Arg Lys Pro Leu Asn Ile Asp His Leu Ser
            180                 185                 190

Asp Asp Lys Leu Arg Asp Lys Ala Lys Glu Leu Trp Asp Thr Leu Tyr
            195                 200                 205

Gln Leu Glu Thr Asp Lys Phe Glu Phe Gly Glu Lys Leu Lys Arg Gln
210                 215                 220

Lys Tyr Asp Ile Thr Thr Leu Arg Ser Arg Ile Asp Gln Ala Gln Lys
225                 230                 235                 240

His Ser Lys Lys Ala Gly Ala Thr Ala Lys Gly Lys Val Gly Gly Arg
                245                 250                 255

Trp Lys

<210> SEQ ID NO 19
<211> LENGTH: 192
<212> TYPE: PRT
<213> ORGANISM: Unknown
<220> FEATURE:
<221> NAME/KEY: PEPTIDE
<222> LOCATION: (1)..(192)
<223> OTHER INFORMATION: rat myosin light chain 1, atrial isoform
<220> FEATURE:
<223> OTHER INFORMATION: Swiss prot identification number P17209
<300> PUBLICATION INFORMATION:
<303> JOURNAL: Nucleic Acids Res.
<304> VOLUME: 18
<305> ISSUE: 6
<306> PAGES: 1581-1586
<307> DATE: 1990-03-25

<400> SEQUENCE: 19

Pro Pro Lys Lys Pro Glu Pro Lys Lys Glu Thr Ala Lys Val Ala Ala
  1               5                  10                  15

Ala Pro Ala Pro Ala Pro Ala Pro Ala Pro Glu Pro Leu Arg Asp Ser
                20                  25                  30

Ala Phe Asp Pro Lys Ser Val Lys Ile Asp Phe Ser Ala Asp Gln Ile
            35                  40                  45

Glu Glu Phe Lys Glu Ala Phe Ser Leu Phe Asp Arg Thr Pro Thr Gly
        50                  55                  60

Glu Met Lys Ile Thr Tyr Gly Gln Cys Gly Asp Val Leu Arg Ala Leu
65                  70                  75                  80

Gly Gln Asn Pro Thr Asn Ala Glu Val Leu Arg Val Leu Gly Lys Pro
                85                  90                  95

Lys Pro Glu Glu Met Asn Ser Lys Thr Leu Asp Phe Glu Met Phe Leu
            100                 105                 110

Pro Ile Leu Gln His Ile Ser Arg Asn Lys Glu Gln Gly Thr Tyr Glu
            115                 120                 125
```

```
Asp Phe Val Glu Gly Leu Arg Val Phe Asp Lys Glu Ser Asn Gly Thr
            130                 135                 140
Val Met Gly Ala Glu Leu Arg His Val Leu Ala Thr Leu Gly Glu Lys
145                 150                 155                 160
Met Ser Glu Ala Glu Val Glu Gln Leu Leu Thr Gly Gln Glu Asp Ala
                165                 170                 175
Asn Gly Cys Ile Asn Tyr Glu Ala Phe Val Lys His Val Met Ser Gly
            180                 185                 190
```

<210> SEQ ID NO 20
<211> LENGTH: 193
<212> TYPE: PRT
<213> ORGANISM: Unknown
<220> FEATURE:
<221> NAME/KEY: PEPTIDE
<222> LOCATION: (1)..(193)
<223> OTHER INFORMATION: Rat cardiac troponin I

<400> SEQUENCE: 20

```
Ala Asp Glu Ser Ser Asp Ala Ala Gly Glu Pro Gln Pro Ala Pro Ala
 1               5                  10                  15
Pro Val Arg Arg Arg Ser Ser Ala Asn Tyr Arg Ala Tyr Ala Thr Glu
            20                  25                  30
Pro His Ala Lys Lys Lys Ser Lys Ile Ser Ala Ser Arg Lys Leu Gln
        35                  40                  45
Leu Lys Thr Leu Met Leu Gln Ile Ala Lys Gln Glu Met Glu Arg Glu
 50                  55                  60
Ala Glu Glu Arg Arg Gly Glu Lys Gly Arg Val Leu Ser Thr Arg Cys
 65                  70                  75                  80
Gln Pro Leu Val Leu Asp Gly Leu Gly Phe Glu Glu Leu Gln Asp Leu
                85                  90                  95
Cys Arg Gln Leu His Ala Arg Val Asp Lys Val Asp Glu Glu Arg Tyr
            100                 105                 110
Asp Val Glu Ala Lys Val Thr Lys Asn Ile Thr Glu Ile Ala Asp Leu
        115                 120                 125
Thr Gln Lys Ile Tyr Asp Leu Arg Gly Lys Phe Lys Arg Pro Thr Leu
130                 135                 140
Arg Arg Val Arg Ile Ser Ala Asp Ala Met Met Gln Ala Leu Leu Gly
145                 150                 155                 160
Thr Arg Ala Lys Glu Ser Leu Asp Leu Arg Ala His Leu Lys Gln Val
                165                 170                 175
Lys Lys Glu Asp Ile Glu Lys Glu Asn Arg Glu Val Gly Asp Trp Arg
            180                 185                 190
Lys
```

<210> SEQ ID NO 21
<211> LENGTH: 192
<212> TYPE: PRT
<213> ORGANISM: Unknown
<220> FEATURE:
<221> NAME/KEY: PEPTIDE
<222> LOCATION: (1)..(192)
<223> OTHER INFORMATION: Human cardiac troponin I

<400> SEQUENCE: 21

```
Ala Asp Gly Ser Ser Asp Ala Ala Arg Glu Pro Arg Pro Ala Pro Ala
 1               5                  10                  15
Pro Ile Arg Arg Arg Ser Ser Asn Tyr Arg Ala Tyr Ala Thr Glu Pro
            20                  25                  30
```

```
His Ala Lys Lys Lys Ser Lys Ile Ser Ala Ser Arg Lys Leu Gln Leu
            35                  40                  45

Lys Thr Leu Leu Leu Gln Ile Ala Lys Gln Glu Leu Glu Arg Glu Ala
     50                  55                  60

Glu Glu Arg Arg Gly Glu Lys Gly Arg Ala Leu Ser Thr Arg Cys Gln
 65                  70                  75                  80

Pro Leu Glu Leu Ala Gly Leu Gly Phe Ala Glu Leu Gln Asp Leu Cys
                 85                  90                  95

Arg Gln Leu His Ala Arg Val Asp Lys Val Asp Glu Glu Arg Tyr Asp
            100                 105                 110

Ile Glu Ala Lys Val Thr Lys Asn Ile Thr Glu Ile Ala Asp Leu Thr
        115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

<210> SEQ ID NO 22
<211> LENGTH: 131
<212> TYPE: PRT
<213> ORGANISM: Unknown
<220> FEATURE:
<221> NAME/KEY: PEPTIDE
<222> LOCATION: (63)..(193)
<223> OTHER INFORMATION: Rat cardiac troponin I

<400> SEQUENCE: 22

Arg Glu Ala Glu Glu Arg Arg Gly Glu Lys Gly Arg Val Leu Ser Thr
  1               5                  10                  15

Arg Cys Gln Pro Leu Val Leu Asp Gly Leu Gly Phe Glu Glu Leu Gln
             20                  25                  30

Asp Leu Cys Arg Gln Leu His Ala Arg Val Asp Lys Val Asp Glu Glu
         35                  40                  45

Arg Tyr Asp Val Glu Ala Lys Val Thr Lys Asn Ile Thr Glu Ile Ala
     50                  55                  60

Asp Leu Thr Gln Lys Ile Tyr Asp Leu Arg Gly Lys Phe Lys Arg Pro
 65                  70                  75                  80

Thr Leu Arg Arg Val Arg Ile Ser Ala Asp Ala Met Met Gln Ala Leu
                 85                  90                  95

Leu Gly Thr Arg Ala Lys Glu Ser Leu Asp Leu Arg Ala His Leu Lys
            100                 105                 110

Gln Val Lys Lys Glu Asp Ile Glu Lys Glu Asn Arg Glu Val Gly Asp
        115                 120                 125

Trp Arg Lys
    130

<210> SEQ ID NO 23
<211> LENGTH: 131
<212> TYPE: PRT
<213> ORGANISM: Unknown
<220> FEATURE:
<221> NAME/KEY: PEPTIDE
<222> LOCATION: (62)..(192)
<223> OTHER INFORMATION: Human cardiac troponin I
```

<400> SEQUENCE: 23

Arg Glu Ala Glu Glu Arg Arg Gly Glu Lys Gly Arg Ala Leu Ser Thr
1               5                   10                  15

Arg Cys Gln Pro Leu Glu Leu Ala Gly Leu Gly Phe Ala Glu Leu Gln
            20                  25                  30

Asp Leu Cys Arg Gln Leu His Ala Arg Val Asp Lys Val Asp Glu Glu
        35                  40                  45

Arg Tyr Asp Ile Glu Ala Lys Val Thr Lys Asn Ile Thr Glu Ile Ala
    50                  55                  60

Asp Leu Thr Gln Lys Ile Phe Asp Leu Arg Gly Lys Phe Lys Arg Pro
65                  70                  75                  80

Thr Leu Arg Arg Val Arg Ile Ser Ala Asp Ala Met Met Gln Ala Leu
                85                  90                  95

Leu Gly Ala Arg Ala Lys Glu Ser Leu Asp Leu Arg Ala His Leu Lys
            100                 105                 110

Gln Val Lys Lys Glu Asp Thr Glu Lys Glu Asn Arg Glu Val Gly Asp
        115                 120                 125

Trp Arg Lys
    130

<210> SEQ ID NO 24
<211> LENGTH: 121
<212> TYPE: PRT
<213> ORGANISM: Unknown
<220> FEATURE:
<221> NAME/KEY: PEPTIDE
<222> LOCATION: (73)..(193)
<223> OTHER INFORMATION: Rat cardiac troponin I

<400> SEQUENCE: 24

Gly Arg Val Leu Ser Thr Arg Cys Gln Pro Leu Val Leu Asp Gly Leu
1               5                   10                  15

Gly Phe Glu Glu Leu Gln Asp Leu Cys Arg Gln Leu His Ala Arg Val
            20                  25                  30

Asp Lys Val Asp Glu Glu Arg Tyr Asp Val Glu Ala Lys Val Thr Lys
        35                  40                  45

Asn Ile Thr Glu Ile Ala Asp Leu Thr Gln Lys Ile Tyr Asp Leu Arg
    50                  55                  60

Gly Lys Phe Lys Arg Pro Thr Leu Arg Arg Val Arg Ile Ser Ala Asp
65                  70                  75                  80

Ala Met Met Gln Ala Leu Leu Gly Thr Arg Ala Lys Glu Ser Leu Asp
                85                  90                  95

Leu Arg Ala His Leu Lys Gln Val Lys Lys Glu Asp Ile Glu Lys Glu
            100                 105                 110

Asn Arg Glu Val Gly Asp Trp Arg Lys
        115                 120

<210> SEQ ID NO 25
<211> LENGTH: 121
<212> TYPE: PRT
<213> ORGANISM: Unknown
<220> FEATURE:
<221> NAME/KEY: PEPTIDE
<222> LOCATION: (72)..(192)
<223> OTHER INFORMATION: Human cardiac troponin I

<400> SEQUENCE: 25

Gly Arg Ala Leu Ser Thr Arg Cys Gln Pro Leu Glu Leu Ala Gly Leu

-continued

```
                1               5                  10                 15
Gly Phe Ala Glu Leu Gln Asp Leu Cys Arg Gln Leu His Ala Arg Val
                    20                  25                 30

Asp Lys Val Asp Glu Glu Arg Tyr Asp Ile Glu Ala Lys Val Thr Lys
            35                  40                 45

Asn Ile Thr Glu Ile Ala Asp Leu Thr Gln Lys Ile Phe Asp Leu Arg
        50                  55                 60

Gly Lys Phe Lys Arg Pro Thr Leu Arg Arg Val Arg Ile Ser Ala Asp
 65                 70                  75                 80

Ala Met Met Gln Ala Leu Leu Gly Ala Arg Ala Lys Glu Ser Leu Asp
                    85                  90                 95

Leu Arg Ala His Leu Lys Gln Val Lys Lys Glu Asp Thr Glu Lys Glu
                100                 105                110

Asn Arg Glu Val Gly Asp Trp Arg Lys
                115                 120
```

<210> SEQ ID NO 26
<211> LENGTH: 17
<212> TYPE: PRT
<213> ORGANISM: Unknown
<220> FEATURE:
<221> NAME/KEY: PEPTIDE
<222> LOCATION: (194)..(210)
<223> OTHER INFORMATION: Rat cardiac troponin I

<400> SEQUENCE: 26

```
Asn Ile Asp Ala Leu Ser Gly Met Glu Gly Arg Lys Lys Lys Phe Glu
 1               5                  10                 15

Gly
```

<210> SEQ ID NO 27
<211> LENGTH: 17
<212> TYPE: PRT
<213> ORGANISM: Unknown
<220> FEATURE:
<221> NAME/KEY: PEPTIDE
<222> LOCATION: (193)..(209)
<223> OTHER INFORMATION: Human cardiac troponin I

<400> SEQUENCE: 27

```
Asn Ile Asp Ala Leu Ser Gly Met Glu Gly Arg Lys Lys Lys Phe Glu
 1               5                  10                 15

Ser
```

<210> SEQ ID NO 28
<211> LENGTH: 180
<212> TYPE: PRT
<213> ORGANISM: Unknown
<220> FEATURE:
<221> NAME/KEY: PEPTIDE
<222> LOCATION: (20)..(199)
<223> OTHER INFORMATION: rat myosin light chain 1, atrial isoform

<400> SEQUENCE: 28

```
Ala Pro Ala Pro Ala Ala Ala Pro Ala Ala Ala Pro Glu Pro Glu Arg
 1               5                  10                 15

Pro Lys Glu Ala Glu Phe Asp Ala Ser Lys Ile Lys Ile Glu Phe Thr
                    20                  25                 30

Pro Glu Gln Ile Glu Glu Phe Lys Glu Ala Phe Gln Leu Phe Asp Arg
            35                  40                 45

Thr Pro Lys Gly Glu Met Lys Ile Thr Tyr Gly Gln Cys Gly Asp Val
```

-continued

```
                50                  55                  60
Leu Arg Ala Leu Gly Gln Asn Pro Thr Gln Ala Glu Val Leu Arg Val
 65                  70                  75                  80

Leu Gly Lys Pro Lys Gln Glu Leu Asn Ser Lys Met Met Asp Phe
                 85                  90                  95

Glu Thr Phe Leu Pro Met Leu Gln His Ile Ser Lys Asn Lys Asp Thr
                100                 105                 110

Gly Thr Tyr Glu Asp Phe Val Glu Gly Leu Arg Val Phe Asp Lys Glu
                115                 120                 125

Gly Asn Gly Thr Val Met Gly Ala Glu Leu Arg His Val Leu Ala Thr
130                 135                 140

Leu Gly Glu Arg Leu Thr Glu Asp Glu Val Glu Lys Leu Met Ala Gly
145                 150                 155                 160

Gln Glu Asp Ser Asn Gly Cys Ile Asn Tyr Glu Ala Phe Val Lys His
                165                 170                 175

Ile Met Ala Ser
                180

<210> SEQ ID NO 29
<211> LENGTH: 19
<212> TYPE: PRT
<213> ORGANISM: Unknown
<220> FEATURE:
<221> NAME/KEY: PEPTIDE
<222> LOCATION: (1)..(19)
<223> OTHER INFORMATION: rat myosin light chain 1, atrial isoform

<400> SEQUENCE: 29

Pro Pro Lys Lys Pro Glu Pro Lys Lys Glu Thr Ala Lys Val Ala Ala
 1               5                  10                  15

Ala Pro Ala

<210> SEQ ID NO 30
<211> LENGTH: 108
<212> TYPE: PRT
<213> ORGANISM: Unknown
<220> FEATURE:
<221> NAME/KEY: PEPTIDE
<222> LOCATION: (191)..(298)
<223> OTHER INFORMATION: Rat cardiac troponin T

<400> SEQUENCE: 30

Asn Met Met His Phe Gly Gly Tyr Ile Gln Lys Ala Gln Thr Glu Arg
 1               5                  10                  15

Lys Ser Gly Lys Arg Gln Thr Glu Arg Glu Lys Lys Lys Lys Ile Leu
                20                  25                  30

Ala Glu Arg Arg Lys Val Leu Ala Ile Asp His Leu Asn Glu Asp Gln
                35                  40                  45

Leu Arg Glu Lys Ala Lys Glu Leu Trp Gln Ser Ile His Asn Leu Glu
 50                  55                  60

Ala Glu Lys Phe Asp Leu Gln Glu Lys Phe Lys Gln Gln Lys Tyr Glu
 65                  70                  75                  80

Ile Asn Val Leu Arg Asn Arg Ile Asn Asp Asn Gln Lys Val Ser Lys
                85                  90                  95

Thr Arg Gly Lys Ala Lys Val Thr Gly Arg Trp Lys
                100                 105

<210> SEQ ID NO 31
<211> LENGTH: 190
```

```
<212> TYPE: PRT
<213> ORGANISM: Unknown
<220> FEATURE:
<221> NAME/KEY: PEPTIDE
<222> LOCATION: (1)..(190)
<223> OTHER INFORMATION: Rat cardiac troponin T

<400> SEQUENCE: 31

Ser Asp Ala Glu Glu Val Val Glu Tyr Glu Glu Glu Gln Glu Glu
 1               5                  10                  15

Glu Asp Trp Ser Glu Glu Glu Asp Glu Gln Glu Glu Ala Val Glu
                20                  25                  30

Glu Glu Asp Gly Glu Ala Glu Pro Asp Pro Gly Glu Ala Glu Ala
            35                  40                  45

Glu Glu Asp Lys Ala Glu Val Gly Pro Asp Glu Glu Ala Arg Asp
        50                  55                  60

Ala Glu Asp Gly Pro Val Glu Asp Ser Lys Pro Lys Pro Ser Arg Leu
 65                  70                  75                  80

Phe Met Pro Asn Leu Val Pro Pro Lys Ile Pro Asp Gly Glu Arg Val
                85                  90                  95

Asp Phe Asp Asp Ile His Arg Lys Arg Met Glu Lys Asp Leu Asn Glu
            100                 105                 110

Leu Gln Thr Leu Ile Glu Ala His Phe Glu Asn Arg Lys Lys Glu Glu
        115                 120                 125

Glu Glu Leu Ile Ser Leu Lys Asp Arg Ile Glu Lys Arg Arg Ala Glu
    130                 135                 140

Arg Ala Glu Gln Gln Arg Ile Arg Asn Glu Arg Lys Glu Arg Gln
145                 150                 155                 160

Asn Arg Leu Ala Glu Glu Arg Ala Arg Glu Glu Glu Glu Asn Arg
                165                 170                 175

Arg Lys Ala Glu Asp Glu Ala Arg Lys Lys Lys Ala Leu Ser
            180                 185                 190

<210> SEQ ID NO 32
<211> LENGTH: 106
<212> TYPE: PRT
<213> ORGANISM: Unknown
<220> FEATURE:
<221> NAME/KEY: PEPTIDE
<222> LOCATION: (182)..(287)
<223> OTHER INFORMATION: Human cardiac troponin T

<400> SEQUENCE: 32

His Phe Gly Gly Tyr Ile Gln Lys Gln Ala Gln Thr Glu Arg Lys Ser
 1               5                  10                  15

Gly Lys Arg Gln Thr Glu Arg Glu Lys Lys Lys Ile Leu Ala Glu
                20                  25                  30

Arg Arg Lys Val Leu Ala Ile Asp His Leu Asn Glu Asp Gln Leu Arg
            35                  40                  45

Glu Lys Ala Lys Glu Leu Trp Gln Ser Ile Tyr Asn Leu Glu Ala Glu
        50                  55                  60

Lys Phe Asp Leu Gln Glu Lys Phe Lys Gln Lys Tyr Glu Ile Asn
 65                  70                  75                  80

Val Leu Arg Asn Arg Ile Asn Asp Asn Gln Lys Val Ser Lys Thr Arg
                85                  90                  95

Gly Lys Ala Lys Val Thr Gly Arg Trp Lys
            100                 105
```

-continued

```
<210> SEQ ID NO 33
<211> LENGTH: 181
<212> TYPE: PRT
<213> ORGANISM: Unknown
<220> FEATURE:
<221> NAME/KEY: PEPTIDE
<222> LOCATION: (1)..(181)
<223> OTHER INFORMATION: Human cardiac troponin T

<400> SEQUENCE: 33

Ser Asp Ile Glu Glu Val Val Glu Glu Tyr Glu Glu Glu Glu Gln Glu
  1               5                  10                  15

Glu Ala Ala Val Glu Glu Gln Glu Glu Ala Ala Glu Glu Asp Ala Glu
             20                  25                  30

Ala Glu Ala Glu Thr Glu Glu Thr Arg Ala Glu Glu Asp Glu Glu Glu
         35                  40                  45

Glu Glu Ala Lys Glu Ala Glu Asp Gly Pro Met Glu Glu Ser Lys Pro
     50                  55                  60

Lys Pro Arg Ser Phe Met Pro Asn Leu Val Pro Pro Lys Ile Pro Asp
 65                  70                  75                  80

Gly Glu Arg Val Asp Phe Asp Asp Ile His Arg Lys Arg Met Glu Lys
                 85                  90                  95

Asp Leu Asn Glu Leu Gln Ala Leu Ile Glu Ala His Phe Glu Asn Arg
            100                 105                 110

Lys Lys Glu Glu Glu Glu Leu Val Ser Leu Lys Asp Arg Ile Glu Arg
        115                 120                 125

Arg Arg Ala Glu Arg Ala Glu Gln Gln Arg Ile Arg Asn Glu Arg Glu
    130                 135                 140

Lys Glu Arg Gln Asn Arg Leu Ala Glu Glu Arg Ala Arg Arg Glu Glu
145                 150                 155                 160

Glu Glu Asn Arg Arg Lys Ala Glu Asp Glu Ala Arg Lys Lys Lys Ala
                165                 170                 175

Leu Ser Asn Met Met

<210> SEQ ID NO 34
<211> LENGTH: 13
<212> TYPE: PRT
<213> ORGANISM: Unknown
<220> FEATURE:
<221> NAME/KEY: PEPTIDE
<222> LOCATION: (136)..(148)
<223> OTHER INFORMATION: Rat cardiac troponin I

<400> SEQUENCE: 34

Arg Gly Lys Phe Lys Arg Pro Thr Leu Arg Arg Val Arg
  1               5                  10

<210> SEQ ID NO 35
<211> LENGTH: 47
<212> TYPE: PRT
<213> ORGANISM: Unknown
<220> FEATURE:
<221> NAME/KEY: PEPTIDE
<222> LOCATION: (129)..(175)
<223> OTHER INFORMATION: Rat cardiac troponin I

<400> SEQUENCE: 35

Thr Gln Lys Ile Tyr Asp Leu Arg Gly Lys Phe Lys Arg Pro Thr Leu
  1               5                  10                  15

Arg Arg Val Arg Ile Ser Ala Asp Ala Met Met Gln Ala Leu Leu Gly
             20                  25                  30
```

Thr Arg Ala Lys Glu Ser Leu Asp Leu Arg Ala His Leu Lys Gln
            35                  40                  45

<210> SEQ ID NO 36
<211> LENGTH: 157
<212> TYPE: PRT
<213> ORGANISM: Unknown
<220> FEATURE:
<221> NAME/KEY: PEPTIDE
<222> LOCATION: (54)..(210)
<223> OTHER INFORMATION: Rat cardiac troponin I

<400> SEQUENCE: 36

Leu Gln Ile Ala Lys Gln Glu Met Glu Arg Glu Ala Glu Arg Arg
 1               5                  10                  15

Gly Glu Lys Gly Arg Val Leu Ser Thr Arg Cys Gln Pro Leu Val Leu
                20                  25                  30

Asp Gly Leu Gly Phe Glu Glu Leu Gln Asp Leu Cys Arg Gln Leu His
            35                  40                  45

Ala Arg Val Asp Lys Val Asp Glu Arg Tyr Asp Val Glu Ala Lys
        50                  55                  60

Val Thr Lys Asn Ile Thr Glu Ile Ala Asp Leu Thr Gln Lys Ile Tyr
 65                  70                  75                  80

Asp Leu Arg Gly Lys Phe Lys Arg Pro Thr Leu Arg Arg Val Arg Ile
                85                  90                  95

Ser Ala Asp Ala Met Met Gln Ala Leu Leu Gly Thr Arg Ala Lys Glu
            100                 105                 110

Ser Leu Asp Leu Arg Ala His Leu Lys Gln Val Lys Lys Glu Asp Ile
            115                 120                 125

Glu Lys Glu Asn Arg Glu Val Gly Asp Trp Arg Lys Asn Ile Asp Ala
        130                 135                 140

Leu Ser Gly Met Glu Gly Arg Lys Lys Lys Phe Glu Gly
145                 150                 155

<210> SEQ ID NO 37
<211> LENGTH: 188
<212> TYPE: PRT
<213> ORGANISM: Unknown
<220> FEATURE:
<221> NAME/KEY: PEPTIDE
<222> LOCATION: (1)..(188)
<223> OTHER INFORMATION: Rat cardiac troponin I

<400> SEQUENCE: 37

Ala Asp Glu Ser Ser Asp Ala Ala Gly Glu Pro Gln Pro Ala Pro Ala
 1               5                  10                  15

Pro Val Arg Arg Arg Ser Ser Ala Asn Tyr Arg Ala Tyr Ala Thr Glu
                20                  25                  30

Pro His Ala Lys Lys Lys Ser Lys Ile Ser Ala Ser Arg Lys Leu Gln
            35                  40                  45

Leu Lys Thr Leu Met Leu Gln Ile Ala Lys Gln Glu Met Glu Arg Glu
        50                  55                  60

Ala Glu Glu Arg Arg Gly Glu Lys Gly Arg Val Leu Ser Thr Arg Cys
 65                  70                  75                  80

Gln Pro Leu Val Leu Asp Gly Leu Gly Phe Glu Glu Leu Gln Asp Leu
                85                  90                  95

Cys Arg Gln Leu His Ala Arg Val Asp Lys Val Asp Glu Glu Arg Tyr
            100                 105                 110

Asp Val Glu Ala Lys Val Thr Lys Asn Ile Thr Glu Ile Ala Asp Leu

-continued

```
                115                 120                 125
Thr Gln Lys Ile Tyr Asp Leu Arg Gly Lys Phe Lys Arg Pro Thr Leu
            130                 135                 140

Arg Arg Val Arg Ile Ser Ala Asp Ala Met Met Gln Ala Leu Leu Gly
145                 150                 155                 160

Thr Arg Ala Lys Glu Ser Leu Asp Leu Arg Ala His Leu Lys Gln Val
                165                 170                 175

Lys Lys Glu Asp Ile Glu Lys Glu Asn Arg Glu Val
            180                 185

<210> SEQ ID NO 38
<211> LENGTH: 199
<212> TYPE: PRT
<213> ORGANISM: Unknown
<220> FEATURE:
<221> NAME/KEY: PEPTIDE
<222> LOCATION: (1)..(199)
<223> OTHER INFORMATION: Rat cardiac troponin I

<400> SEQUENCE: 38

Ala Asp Glu Ser Ser Asp Ala Ala Gly Glu Pro Gln Pro Ala Pro Ala
1               5                   10                  15

Pro Val Arg Arg Arg Ser Ser Ala Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Met Leu Gln Ile Ala Lys Gln Glu Met Glu Arg Glu
    50                  55                  60

Ala Glu Glu Arg Arg Gly Glu Lys Gly Arg Val Leu Ser Thr Arg Cys
65                  70                  75                  80

Gln Pro Leu Val Leu Asp Gly Leu Gly Phe Glu Glu Leu Gln Asp Leu
                85                  90                  95

Cys Arg Gln Leu His Ala Arg Val Asp Lys Val Asp Glu Glu Arg Tyr
            100                 105                 110

Asp Val Glu Ala Lys Val Thr Lys Asn Ile Thr Glu Ile Ala Asp Leu
        115                 120                 125

Thr Gln Lys Ile Tyr Asp Leu Arg Gly Lys Phe Lys Arg Pro Thr Leu
            130                 135                 140

Arg Arg Val Arg Ile Ser Ala Asp Ala Met Met Gln Ala Leu Leu Gly
145                 150                 155                 160

Thr Arg Ala Lys Glu Ser Leu Asp Leu Arg Ala His Leu Lys Gln Val
                165                 170                 175

Lys Lys Glu Asp Ile Glu Lys Glu Asn Arg Glu Val Gly Asp Trp Arg
            180                 185                 190

Lys Asn Ile Asp Ala Leu Ser
        195

<210> SEQ ID NO 39
<211> LENGTH: 12
<212> TYPE: PRT
<213> ORGANISM: Unknown
<220> FEATURE:
<221> NAME/KEY: PEPTIDE
<222> LOCATION: (188)..(199)
<223> OTHER INFORMATION: Human cardiac troponin I

<400> SEQUENCE: 39

Gly Asp Trp Arg Lys Asn Ile Asp Ala Leu Ser Gly
1               5                   10
```

```
<210> SEQ ID NO 40
<211> LENGTH: 6
<212> TYPE: PRT
<213> ORGANISM: Unknown
<220> FEATURE:
<221> NAME/KEY: PEPTIDE
<222> LOCATION: (70)..(75)
<223> OTHER INFORMATION: rat myosin light chain 1, atrial isoform

<400> SEQUENCE: 40

Tyr Gly Gln Cys Gly Asp
 1               5

<210> SEQ ID NO 41
<211> LENGTH: 36
<212> TYPE: PRT
<213> ORGANISM: Unknown
<220> FEATURE:
<221> NAME/KEY: PEPTIDE
<222> LOCATION: (157)..(192)
<223> OTHER INFORMATION: rat cardiac troponin I

<400> SEQUENCE: 41

Ala Leu Leu Gly Thr Arg Ala Lys Glu Ser Leu Asp Leu Arg Ala His
 1               5                  10                  15

Leu Lys Gln Val Lys Lys Glu Asp Ile Glu Lys Glu Asn Arg Glu Val
                20                  25                  30

Gly Asp Trp Arg
            35

<210> SEQ ID NO 42
<211> LENGTH: 65
<212> TYPE: PRT
<213> ORGANISM: Unknown
<220> FEATURE:
<221> NAME/KEY: PEPTIDE
<222> LOCATION: (1)..(65)
<223> OTHER INFORMATION: rat cardiac troponin I

<400> SEQUENCE: 42

Ala Asp Glu Ser Ser Asp Ala Ala Gly Glu Pro Gln Pro Ala Pro Ala
 1               5                  10                  15

Pro Val Arg Arg Arg Ser Ser Ala Asn Tyr Arg Ala Tyr Ala Thr Glu
                20                  25                  30

Pro His Ala Lys Lys Lys Ser Lys Ile Ser Ala Ser Arg Lys Leu Gln
            35                  40                  45

Leu Lys Thr Leu Met Leu Gln Ile Ala Lys Gln Glu Met Glu Arg Glu
        50                  55                  60

Ala
 65

<210> SEQ ID NO 43
<211> LENGTH: 11
<212> TYPE: PRT
<213> ORGANISM: Unknown
<220> FEATURE:
<221> NAME/KEY: PEPTIDE
<222> LOCATION: (189)..(199)
<223> OTHER INFORMATION: rat cardiac troponin I

<400> SEQUENCE: 43

Gly Asp Trp Arg Lys Asn Ile Asp Ala Leu Ser
 1               5                  10
```

```
<210> SEQ ID NO 44
<211> LENGTH: 12
<212> TYPE: PRT
<213> ORGANISM: Unknown
<220> FEATURE:
<221> NAME/KEY: PEPTIDE
<222> LOCATION: (137)..(148)
<223> OTHER INFORMATION: rat cardiac troponin I

<400> SEQUENCE: 44

Gly Lys Phe Lys Arg Pro Thr Leu Arg Arg Val Arg
 1               5                  10

<210> SEQ ID NO 45
<211> LENGTH: 47
<212> TYPE: PRT
<213> ORGANISM: Unknown
<220> FEATURE:
<221> NAME/KEY: PEPTIDE
<222> LOCATION: (96)..(142)
<223> OTHER INFORMATION: Synthetic skeletal troponin I

<400> SEQUENCE: 45

Thr Gln Lys Ile Tyr Asp Leu Arg Gly Lys Phe Lys Arg Pro Thr Leu
 1               5                  10                  15

Arg Arg Val Arg Ile Ser Ala Asp Ala Met Met Gln Ala Leu Leu Gly
             20                  25                  30

Thr Arg Ala Lys Glu Ser Leu Asp Leu Arg Ala His Leu Lys Gln
         35                  40                  45

<210> SEQ ID NO 46
<211> LENGTH: 27
<212> TYPE: PRT
<213> ORGANISM: Unknown
<220> FEATURE:
<221> NAME/KEY: PEPTIDE
<222> LOCATION: (28)..(54)
<223> OTHER INFORMATION: Rat cardiac troponin I

<400> SEQUENCE: 46

Ala Tyr Ala Thr Glu Pro His Ala Lys Lys Lys Ser Lys Ile Ser Ala
 1               5                  10                  15

Ser Arg Lys Leu Gln Leu Lys Thr Leu Met Leu
             20                  25

<210> SEQ ID NO 47
<211> LENGTH: 12
<212> TYPE: PRT
<213> ORGANISM: Unknown
<220> FEATURE:
<221> NAME/KEY: PEPTIDE
<222> LOCATION: (137)..(148)
<223> OTHER INFORMATION: human cardiac troponin I

<400> SEQUENCE: 47

Lys Phe Lys Arg Pro Thr Leu Arg Arg Val Arg Ile
 1               5                  10

<210> SEQ ID NO 48
<211> LENGTH: 161
<212> TYPE: PRT
<213> ORGANISM: Unknown
<220> FEATURE:
<221> NAME/KEY: PEPTIDE
<222> LOCATION: (1)..(161)
<223> OTHER INFORMATION: human cardiac/slow skeletal troponin C
```

-continued

```
<400> SEQUENCE: 48

Met Asp Asp Ile Tyr Lys Ala Ala Val Glu Gln Leu Thr Glu Glu Gln
 1               5                  10                  15

Lys Asn Glu Phe Lys Ala Ala Phe Asp Ile Phe Val Leu Gly Ala Glu
                20                  25                  30

Asp Gly Cys Ile Ser Thr Lys Glu Lys Gly Lys Val Met Arg Met Lys
            35                  40                  45

Gly Gln Asn Pro Thr Pro Glu Glu Lys Gln Glu Met Ile Asp Glu Val
     50                  55                  60

Asp Glu Asp Gly Ser Gly Thr Val Asp Phe Asp Glu Phe Leu Val Met
 65                  70                  75                  80

Met Val Arg Cys Met Lys Asp Asp Ser Lys Gly Lys Ser Glu Glu
                 85                  90                  95

Leu Ser Asp Leu Phe Arg Met Phe Asp Lys Asn Ala Asp Gly Tyr Ile
                100                 105                 110

Asp Leu Glu Glu Leu Lys Ile Met Leu Gln Ala Thr Gly Glu Thr Ile
            115                 120                 125

Thr Glu Asp Asp Ile Glu Glu Leu Met Lys Asp Gly Asp Lys Arg Arg
    130                 135                 140

Asp Gly Arg Ile Asp Tyr Asp Glu Phe Leu Glu Phe Met Lys Gly Val
145                 150                 155                 160

Glu

<210> SEQ ID NO 49
<211> LENGTH: 94
<212> TYPE: PRT
<213> ORGANISM: Unknown
<220> FEATURE:
<221> NAME/KEY: PEPTIDE
<222> LOCATION: (1)..(94)
<223> OTHER INFORMATION: human cardiac/slow skeletal troponin C

<400> SEQUENCE: 49

Met Asp Asp Ile Tyr Lys Ala Ala Val Glu Gln Leu Thr Glu Glu Gln
 1               5                  10                  15

Lys Asn Glu Phe Lys Ala Ala Phe Asp Ile Phe Val Leu Gly Ala Glu
                20                  25                  30

Asp Gly Cys Ile Ser Thr Lys Glu Lys Gly Lys Val Met Arg Met Lys
            35                  40                  45

Gly Gln Asn Pro Thr Pro Glu Glu Lys Gln Glu Met Ile Asp Glu Val
     50                  55                  60

Asp Glu Asp Gly Ser Gly Thr Val Asp Phe Asp Glu Phe Leu Val Met
 65                  70                  75                  80

Met Val Arg Cys Met Lys Asp Asp Ser Lys Gly Lys Ser Glu
                 85                  90

<210> SEQ ID NO 50
<211> LENGTH: 194
<212> TYPE: PRT
<213> ORGANISM: Unknown
<220> FEATURE:
<221> NAME/KEY: PEPTIDE
<222> LOCATION: (1)..(194)
<223> OTHER INFORMATION: human cardiac myosin light chain 1

<400> SEQUENCE: 50

Ala Pro Lys Lys Pro Glu Pro Lys Lys Asp Asp Ala Lys Ala Ala Pro
 1               5                  10                  15
```

-continued

```
Lys Ala Ala Pro Ala Pro Ala Pro Pro Pro Glu Pro Glu Arg Pro Lys
            20              25              30

Glu Val Glu Phe Asp Ala Ser Lys Ile Lys Ile Glu Phe Thr Pro Glu
        35              40              45

Gln Ile GLu Glu Phe Lys Glu Ala Phe Met Leu Phe Asp Arg Thr Pro
        50              55              60

Lys Cys Glu Met Lys Ile Thr Tyr Gly Gln Cys Gly Asp Val Leu Arg
65              70              75              80

Ala Leu Gly Gln Asn Pro Thr Gln Ala Glu Val Leu Arg Val Leu Gly
            85              90              95

Lys Pro Arg Gln Glu Glu Leu Asn Thr Lys Met Met Asp Phe Glu Thr
            100             105             110

Phe Leu Pro Met Leu Gln His Ile Ser Lys Asn Lys Asp Thr Glu Tyr
        115             120             125

Tyr Glu Asp Phe Val Glu Gly Leu Arg Val Phe Asp Lys Glu Gly Asn
    130             135             140

Gly Thr Val Met Gly Ala Glu Leu Arg His Val Leu Ala Thr Leu Gly
145             150             155             160

Glu Arg Leu Thr Glu Asp Glu Val Glu Lys Leu Met Ala Gly Gln Glu
            165             170             175

Asp Ser Asn Gly Cys Ile Asn Tyr Glu Ala Phe Val Lys His Ile Met
            180             185             190

Ser Ser
```

METHODS OF DIAGNOSING MUSCLE DAMAGE

RELATED APPLICATIONS

This application claims the benefit of priority of U.S. Provisional Patent Application No. 60/052,697, filed Jul. 16, 1997, the contents of which is incorporated herein by reference.

FIELD OF THE INVENTION

This invention relates to methods for assessing the extent of cellular damage of muscle tissue, particularly skeletal and cardiac muscle.

BACKGROUND OF THE INVENTION

When circulation of blood, and therefore oxygen, to muscle is interrupted (ischemia), the ability of the muscle to contract is impaired. Even if circulation is restored (e.g., by reperfusion), muscle function can remain depressed. In certain types of muscle, such as cardiac muscle, the effects of ischemia can have severe consequences, and inadequate circulation of blood to the heart is one of the most important causes of morbidity in developed countries. Clinically, ischemia and reperfusion injury manifest as a spectrum. In its mildest form, ischemia is transient, reperfusion is established quickly and the reduced contractility of the muscle tissue is temporary and reversible. However, longer and more severe ischemia produces irreversible damage and cellular necrosis.

The functions of myofilament specific proteins, such as troponin I and troponin T (members of the regulatory complex), myosin light chain 1 (MLC1), and α-actinin are affected during hypoxemia (i.e., reduced delivery of oxygen due to a reduced partial pressure and/or arterial content of oxygen), ischemia, and/or ischemia/reperfusion injury. These changes affect contraction of muscle by apparently altering the interaction of troponin I, troponin T, myosin light chain 1, and α-actinin with other proteins critical for normal muscle contraction.

Troponin I is a key component of the troponin regulatory complex which directly controls striated (cardiac and skeletal) muscle contraction and relaxation. Troponin T is also part of the troponin complex and is involved in assembly of troponin-tropomyosin on the actin filament. α-actinin is a cytoskeletal protein, the main component of the Z lines. Traditionally α-actinin was believed to keep the actin filaments aligned. However, the large changes in conformation of Z lines during the cross bridge cycle suggest that α-actinin has a dynamic role during muscle contraction. Myosin light chain 1 is an integral part of the myosin myofibril. Myosin light chain 1 is found in slow and fast skeletal and atrial and ventricular cardiac muscles.

To date, the underlying molecular changes responsible for the reduced contractility of injured muscles resulting from hypoxemia, hypoxemia, ischemia, and reperfusion are not known. As a result, early diagnosis of the above-mentioned states and assessment of the extent of muscle damage in a subject, particularly the difference between reversible and irreversible muscle damage, has not been possible. The current serum diagnostic indicators used in diagnosing myocardial infarction (e.g., anti-troponin I, anti-troponin T and anti-creatine kinase MB antibodies by Spectral Diagnostics Inc., Toronto, Canada; anti-troponin T, anti-MLC1 antibodies by Baxter Inc., Chicago, Ill.; and anti-troponin I antibody by Baxter Inc.) are indicators of myocardial necrosis (irreversible damage) since they detect proteins which are released from the heart myocyte following the loss of cellular membrane integrity. These indicators provide no information as to the extent or type of myocardial damage, or the molecular nature of which would clearly benefit the art. To date there are no commercially-available serum or urine markers for skeletal muscle damage.

SUMMARY OF THE INVENTION

The present invention provides methods for assessing cardiac and skeletal muscle damage in a subject. The method includes obtaining a biological sample from a subject being assessed for muscle damage and evaluating the sample for presence or absence of one or more myofilament protein modification products, including, for example, individual protein fragments, or covalent or non-covalent complexes formed from two or more myofilament proteins, which may be intact proteins or protein fragments in the biological sample.

According to one aspect of the invention, the amount of myofilament protein modification product present in a biological sample can be assessed as an indication of the extent of muscle damage in the subject. In accordance with the invention, a method of assessing muscle damage in a subject comprises obtaining a biological sample from a subject, incubating the biological sample with at least one compound which specifically binds to one or more different myofilament proteins or myofilament protein modification products present in the sample, under conditions which allow the compound to form one or more complexes with the myofilament proteins or myofilament protein modification products, detecting said one or more complexes, and characterizing the profile of said one or more myofilament proteins or myofilament protein modification products contained in said one or more complexes, as an indication of the extent or type of muscle damage in the subject. The compound can for example be an antibody, a protein, a peptide or a peptidomimetic that forms a complex with the myofilament protein modification product. In certain embodiments, the myofilament protein is troponin I, troponin T, troponin C, myosin light chain 1, α-actinin or a fragment(s) or combination(s) thereof.

The invention also provides a kit for assessing myocardial damage in a biological sample obtained from a subject. In one embodiment, the kit includes a compound which specifically binds to a myofilament protein modification product and instructions explaining how to use the kit to assess muscle damage in a biological sample obtained from a subject. In other embodiments the compound may bind to one or more myofilament protein modification products. The kit may also include a label or labelled compound used to identify the myofilament protein modification product(s) thereof. The kit may further include a reagent(s) appropriate for detecting the label.

The invention further provides assays, e.g., screening tests, for identifying an agent which modulates the level of one or more myofilament protein modification products in a biological sample. The assay involves obtaining a biological sample containing a myofilament protein modification product from a subject, testing the biological sample with an agent (e.g., contacting the sample with the agent), and determining the effect of the agent on the level of the myofilament protein modification product in the biological sample, wherein an agent(s) which modulate the level of the myofilament protein modification product in a biological sample are identified.

In accordance with the invention, the presence and level of myofilament modification products in a biological sample are detected. The biological sample can be obtained from any subject exhibiting, exposed to, suspected of having, or being treated for, a condition or conditions which could cause hypoxemic/ischemic damage to muscle tissue. The invention therefore also provides for the assessment of efficacy of, for example, treatments such as cardioplegia (preservation) and preconditioning of the myocardium, and rehabilitation following heart disease-related injury such as infarction. The invention is also applicable to rehabilitation of patients with skeletal muscle damage, disease such as rhabdomyolysis, respiratory diseases such as, but not restricted to, chronic obstructive pulmonary disease, emphysema, asthma and bronchitis, bullectomy (lung reduction surgery), and following insult due to surgery or other trauma. The invention further provides for the assessment of the appropriateness of the level of training in athletes and animals such as race horses, where myofilament modification products as indicators of skeletal muscle breakdown can be detected. Yet other applications of the invention include the diagnosis of respiratory muscle dysfunction, wherein myofilament modification products can also exist.

Other features and advantages of the invention will be apparent from the following detailed description, and from the claims.

BRIEF DESCRIPTION OF THE DRAWINGS

Embodiments of the invention will now be described, by way of example, with reference to the accompanying drawings, wherein.

Figure 6:
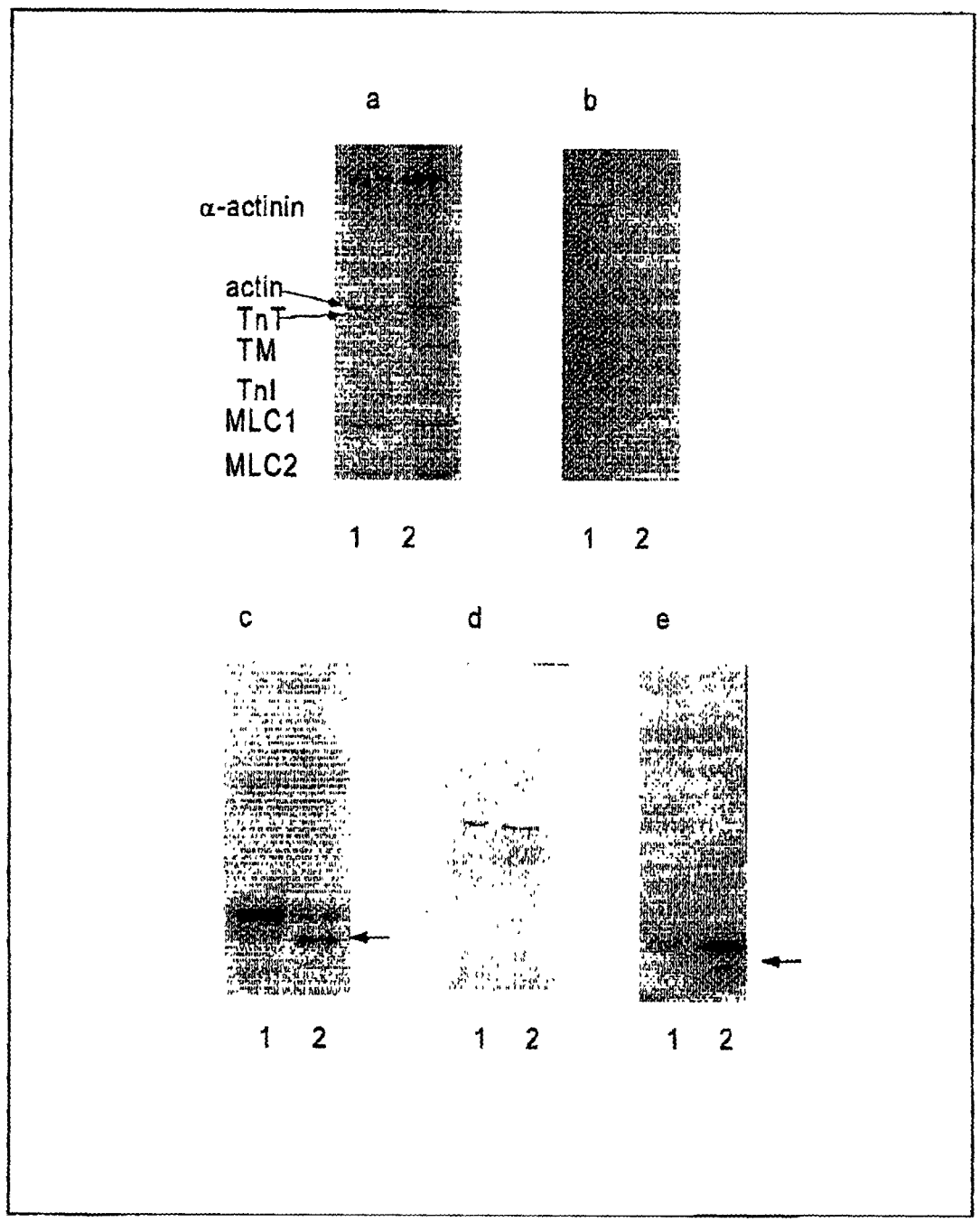

FIG. 6 show the results of an SDS-PAGE analysis of isolated myofibrils from control and globally ischemic rat hearts. Left ventricular tissue samples obtained from isolated rat hearts were placed in saline in plastic bag for 60 min at either 4° C. (control, 1) or 39° C. (global ischemia, 2). Panel A shows the coomassie blue stain of the 12.5% crosslinked gel. Panels B to F show corresponding western blots using anti-α-actinin (panel B), anti-TnI peptide residues 136 to 148 (SEQ ID NO:34) (panel C), anti-TnT (panel D), and anti-MLC1 (panel E) antibodies. Modification products are indicated by arrows. The data reveal a loss of α-actinin in the global ischemic myofibrils and degradation of TnI and MLC1, respectively.

Figure 7:
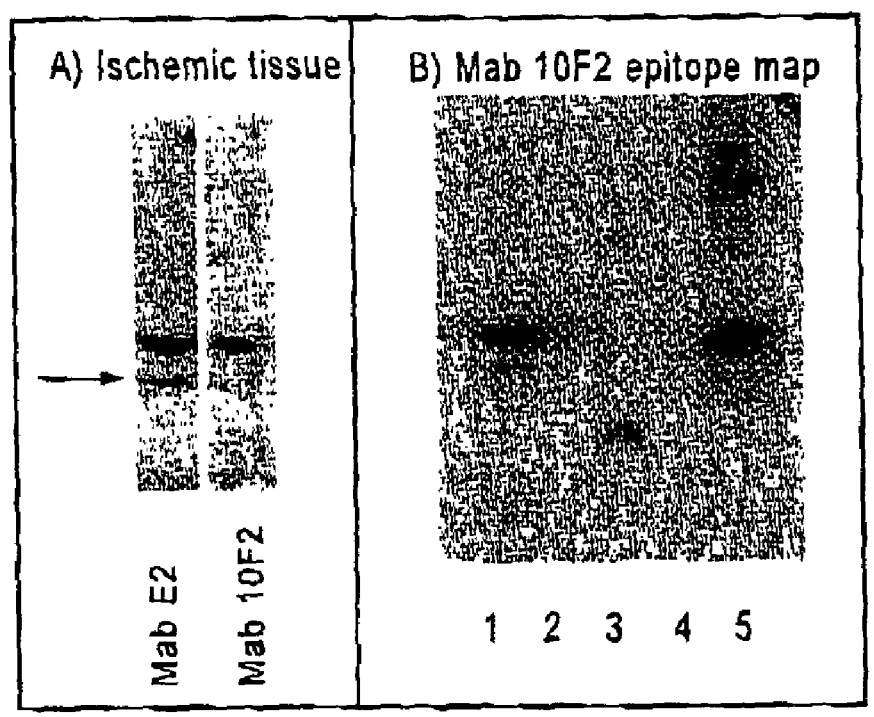

FIG. 7 shows an immunological analysis of the troponin I modification product. FIG. 7A shows a western blot of left ventricular tissue samples obtained from hearts which experience 60 min ischemia followed by 45 min reperfusion (ischemic tissue) using the anti-troponin I antibodies E2 and 10F2. FIG. 7B shows a western blot of MAb 10F2 against intact cardiac troponin I (lane 1), troponin I peptide residues 129-175 (SEQ ID NO:35) (lane 2), troponin I residues 54 to 210 (SEQ ID NO:36) (lane 3), troponin I residues 1 to 188 (SEQ ID NO:37) (lane 4) and troponin I residues 1 to 199 (SEQ ID NO:38) (lane 5). The 22 kDa TnI degradation product has C-terminus proteolysis.

Figure 8:
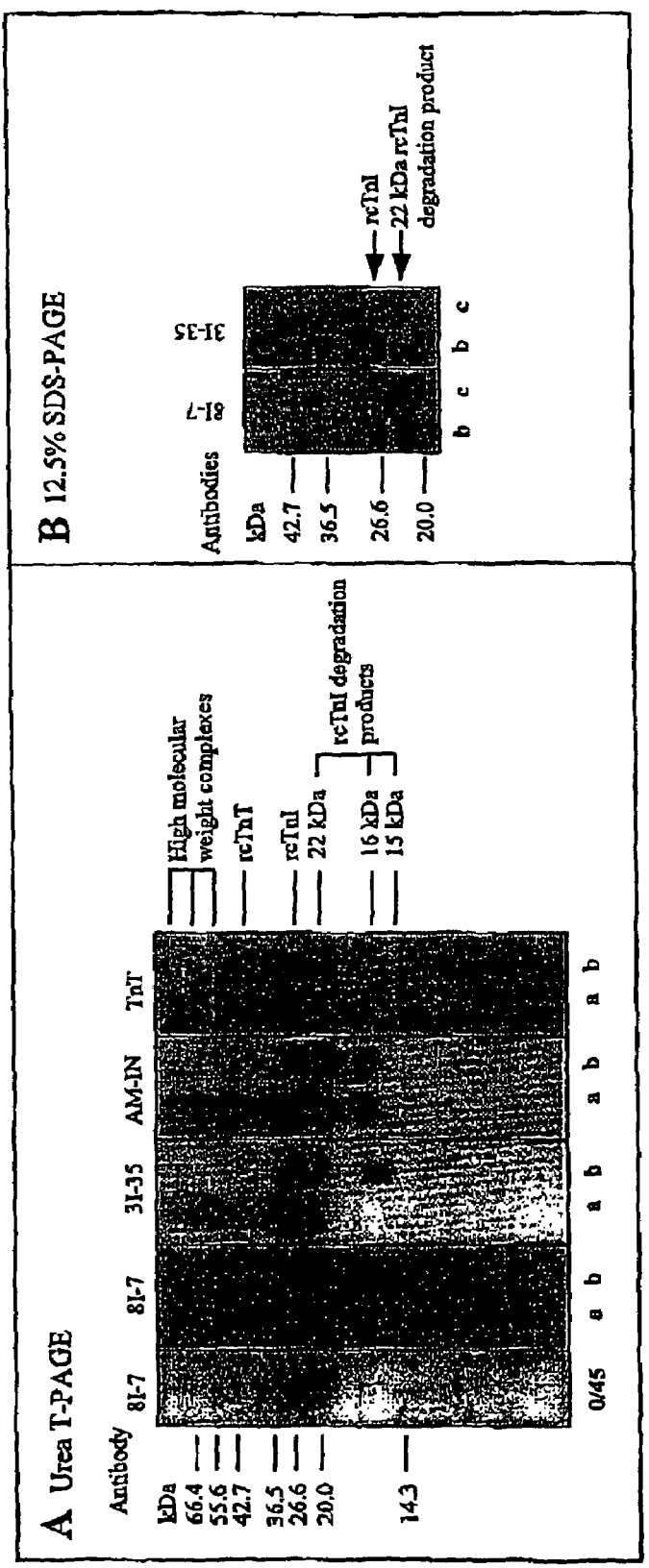

FIG. 8 shows the results of a western blot analysis of ischemia/reperfusion in rat cardiac tissue and effluent. Panel A shows western blots for several anti-TnI MAbs and an anti-TnT MAb used to probe urea T-PAGE separated tissue samples (20 µg) from rat hearts that underwent 0, 15 (lane a), and 60 (lane b) min ischemia followed by 45 min reperfusion. An increase in the severity of ischemia from 15 to 60 min resulted in progressive, and selective, modification of TnI through modification and complex formation. Panel B shows a western blot using the two anti-TnI MAbs 8I-7 and 3I-35 to probe 12.5% SDS-PAGE separated 60/45 tissue (5 µg) (lane b), and 60 min ischemia/45 min reperfusion effluent (lane c). The 22 kDa rat cardiac TnI modification product is released from necrotic cardiomyocytes following severe ischemia. The MAb 3I-35 has weak associations with the 22 kDa TnI modification product. Table 3 quantifies the progressive alteration of TnI with increasing severity of ischemia/reperfusion injury.

Figure 9:
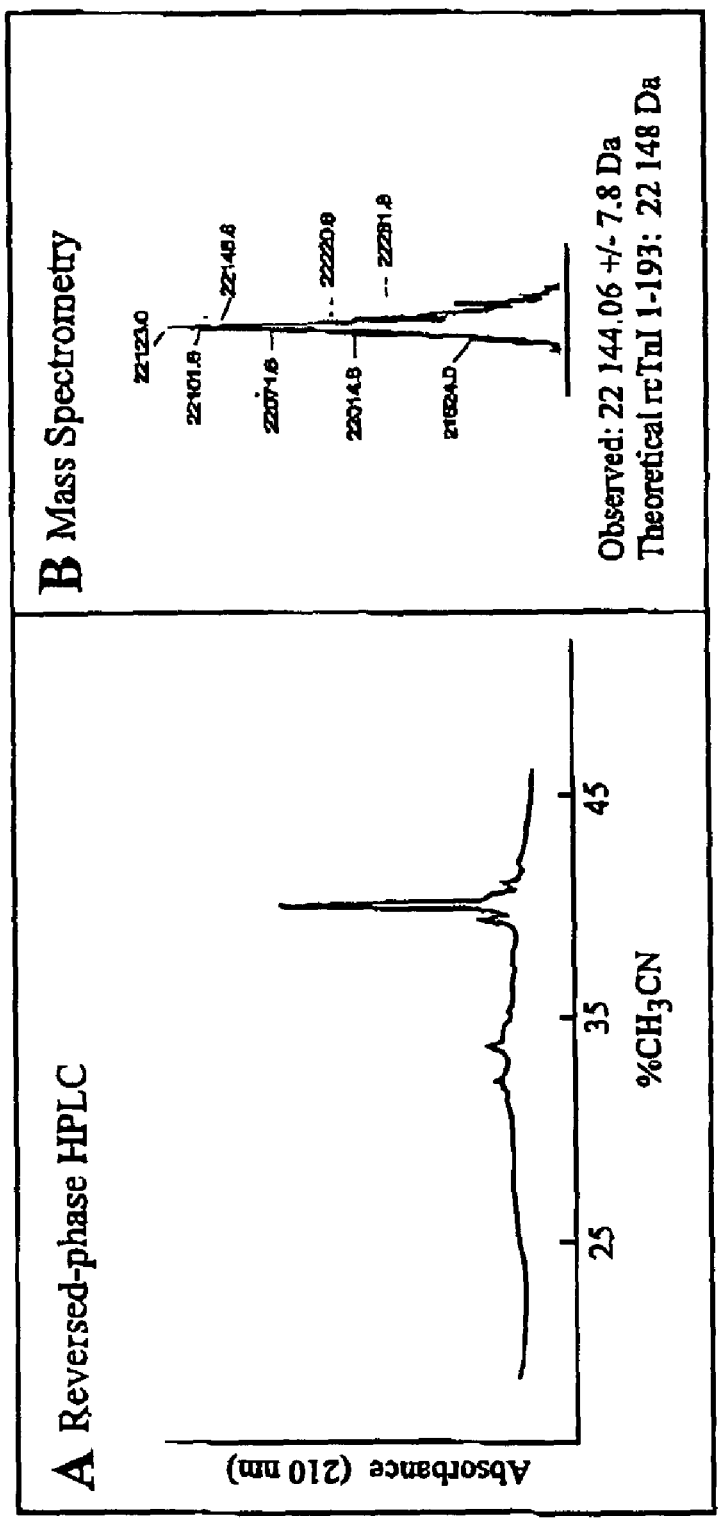

FIG. 9 shows the isolation and identification of a 22 kDa TnI modification product from ischemic/reperfused rat hearts by TnC affinity chromatography. Panel A shows the RP-HPLC elution profile of proteins isolated by TnC affinity chromatography. Left ventricular tissue from rat hearts which experienced 60 min ischemia followed by 45 min reperfusion were homogenized and loaded on to the affinity column. The column was washed with 20 mmol/l Tris-HCl pH 7.4, 50 mmol/l KCl, 1 mmol/l CaCl$_2$, then bound proteins were eluted with 65 mmol/l glycine-HCl pH 3.2. Panel B shows the single peak obtained from electrospray mass spectrometry of the RP-HPLC peak shown in panel A.

Figure 10:
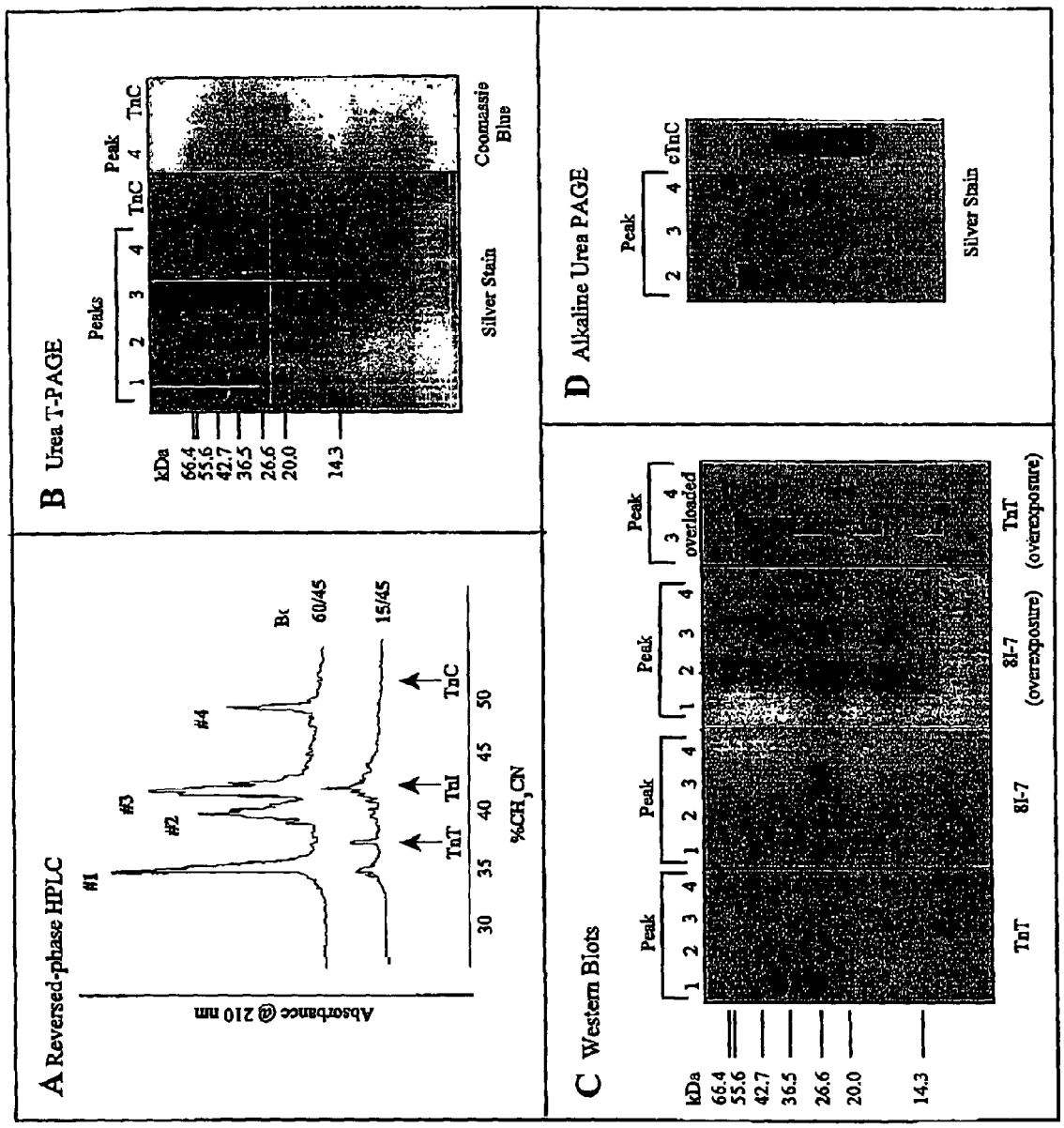

FIG. 10 shows the isolation of modified TnI products from ischemic/reperfused rat hearts by anti-TnI antibody affinity chromatography. Panel A shows RP-HPLC elution profiles of proteins that bound to the 8I-7 MAb affinity column. Left ventricular tissue from rat hearts which experienced either 15/45 or 60/45 ischemia/reperfusion was homogenized and loaded onto the affinity column. The column was washed with 20 mmol/l Tris-HCl pH 7.4, 50 mmol/l potassium chloride, 1 mmol/l calcium chloride, and bound fractions eluted with 65 mmol/l glycine-HCl, pH 3.2. Arrows indicate elution times of isolated intact cardiac TnI, TnC and TnT. Panel B shows the urea tricine-PAGE (T-PAGE) separation of RP-HPLC fractions obtained from 8I-7 MAb affinity chromatography of 60/45 tissue. Peaks 1 to 4 were collected from RP-HPLC, separated by urea T-PAGE, and stained with coomassie blue and silver. Peak numbers correspond to the specific peaks from 60/45 in panel A. Panel C shows western blot analysis of the T-PAGE separated RP-HPLC fractions with MAb 8I-7 and anti-TnT MAb. Overloading of samples and/or overexposure of western blots was necessary to visualize the covalent complexes, due to their low amounts. Panel D shows alkaline urea PAGE analysis of peaks 2 to 4 (since peak 1 contains TnT). TnI and TnT will only migrate into the gel if complexed to TnC.

Figure 11:
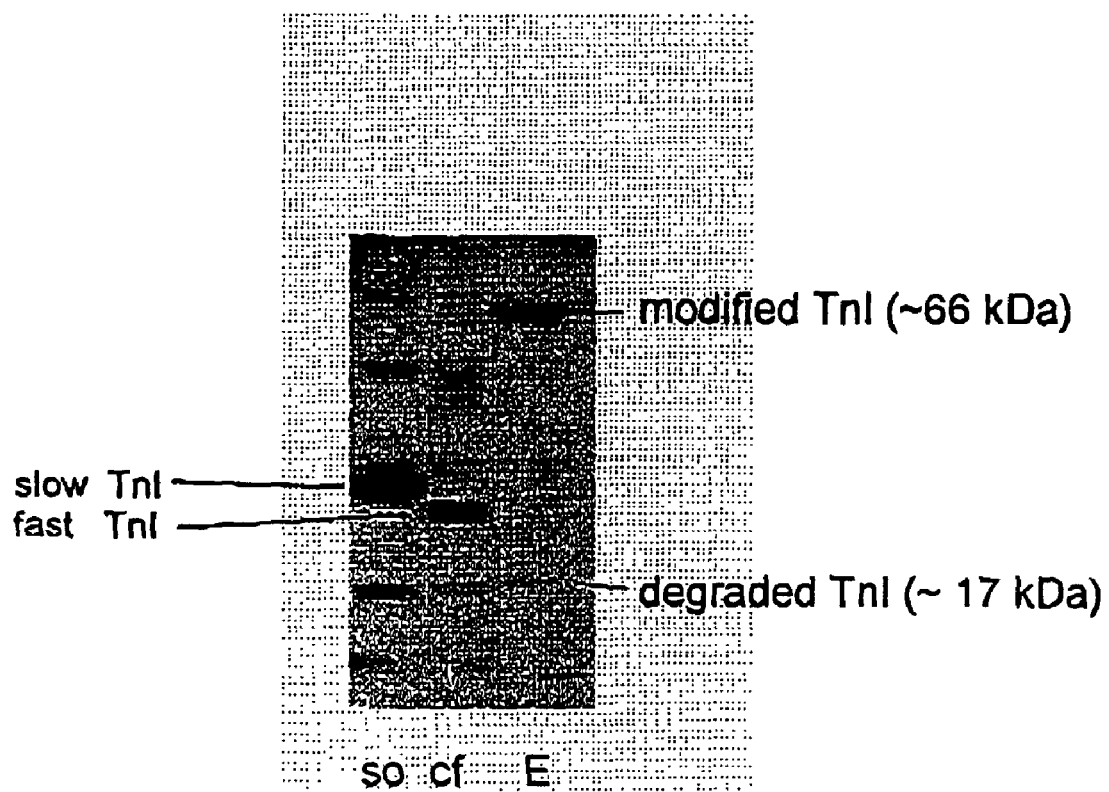

FIG. 11 is a western blot showing skeletal TnI in the effluent from an isolated rat diaphragm (skeletal muscle) preparation. Feline caudofemoralis (CF; fast skeletal muscle) and soleus (SO; slow skeletal muscle) were used to identify the fast and slow isoforms of TnI. The effluent (E) was collected during stimulation (see below) of the in vitro rat diaphragm. Degraded and modified forms of TnI are visible using the anti-TnI MAb C5.

Figure 12A:
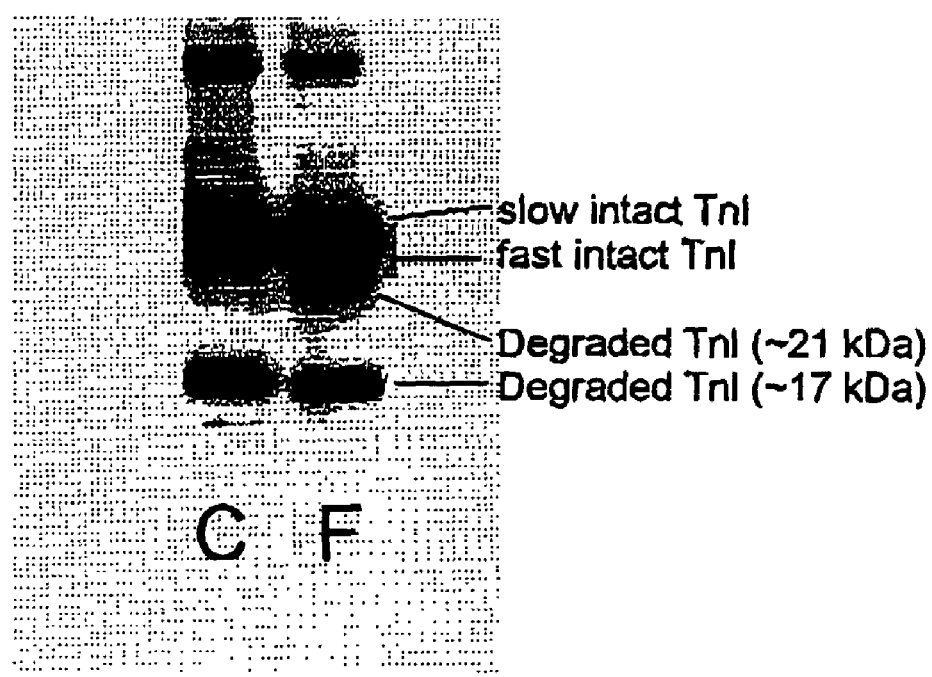

FIGS. 12A and B show detection of skeletal TnI and TnT, respectively, in the isolated rat diaphragm preparation before (C) and following stimulation (F) using the anti-TnI MAb C5 and the anti-TnT MAb JLT-12.

Figure 13A:
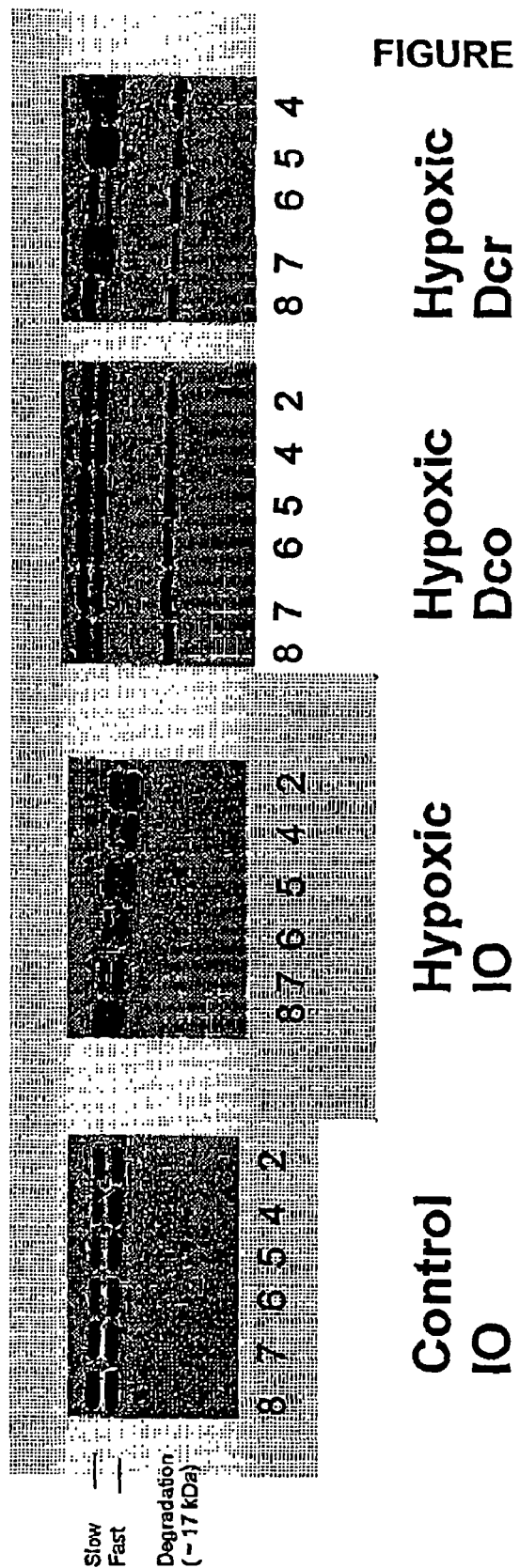

FIG. 13A shows detection of skeletal TnI in selected canine respiratory muscles (IO—internal oblique; Dco—diaphragm costal; Dcr—diaphragm crural) by western blot analysis using the anti-TnI MAb C5. The top band is the slow isoform with the next lower band the fast isoform of troponin I. The third band (seen only in the two right blots) is the degraded portion of troponin I.

Figure 13B:
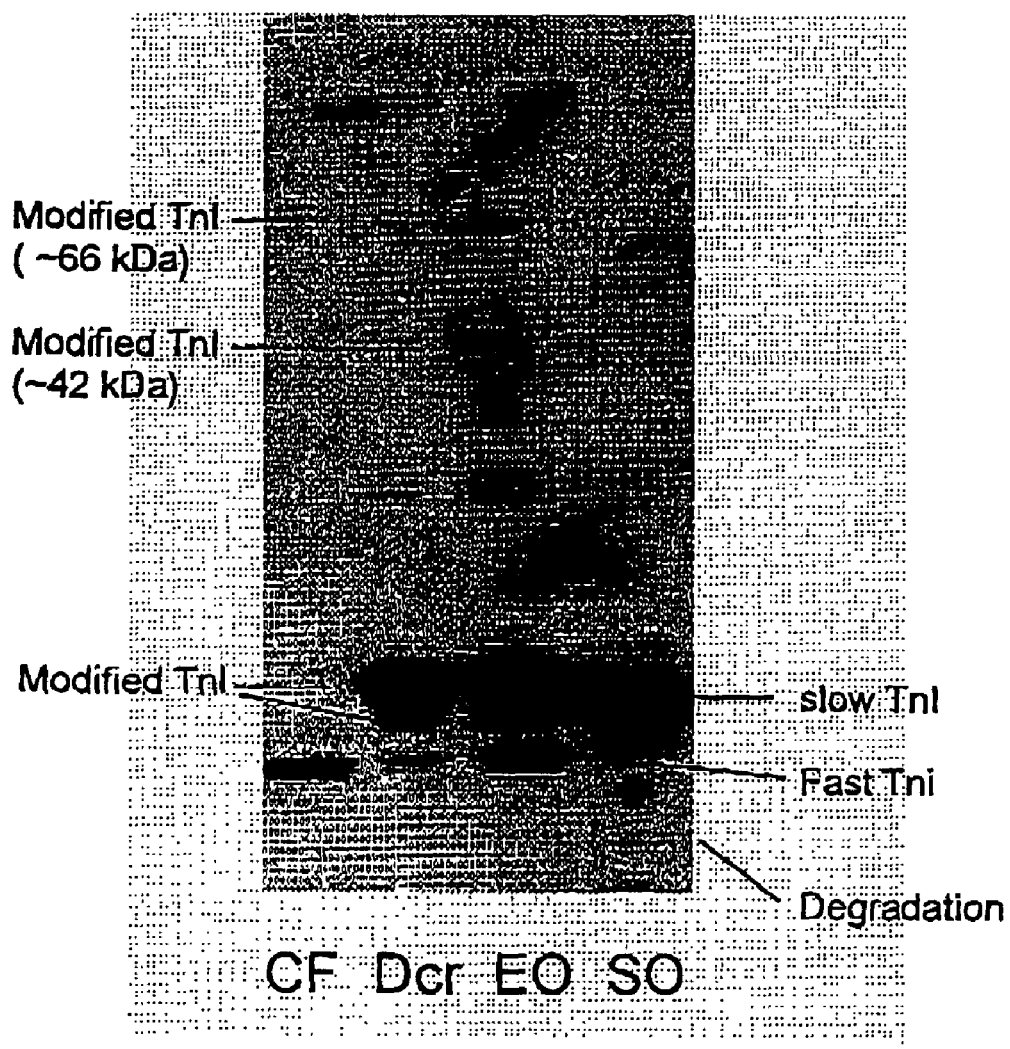

FIG. 13B shows a western blot of skeletal TnI using the anti-TnI MAb 8I-7 with canine respiratory muscle samples. Feline caudofemoralis (CF; fast skeletal) and soleus (SO; slow skeletal) were used to identify the fast and slow isoforms of TnI. Several modified forms of TnI can be visualized from the hypoxic tissues from the crural diaphragm (Dcr) and external oblique (EO) tissue samples.

Figure 14:
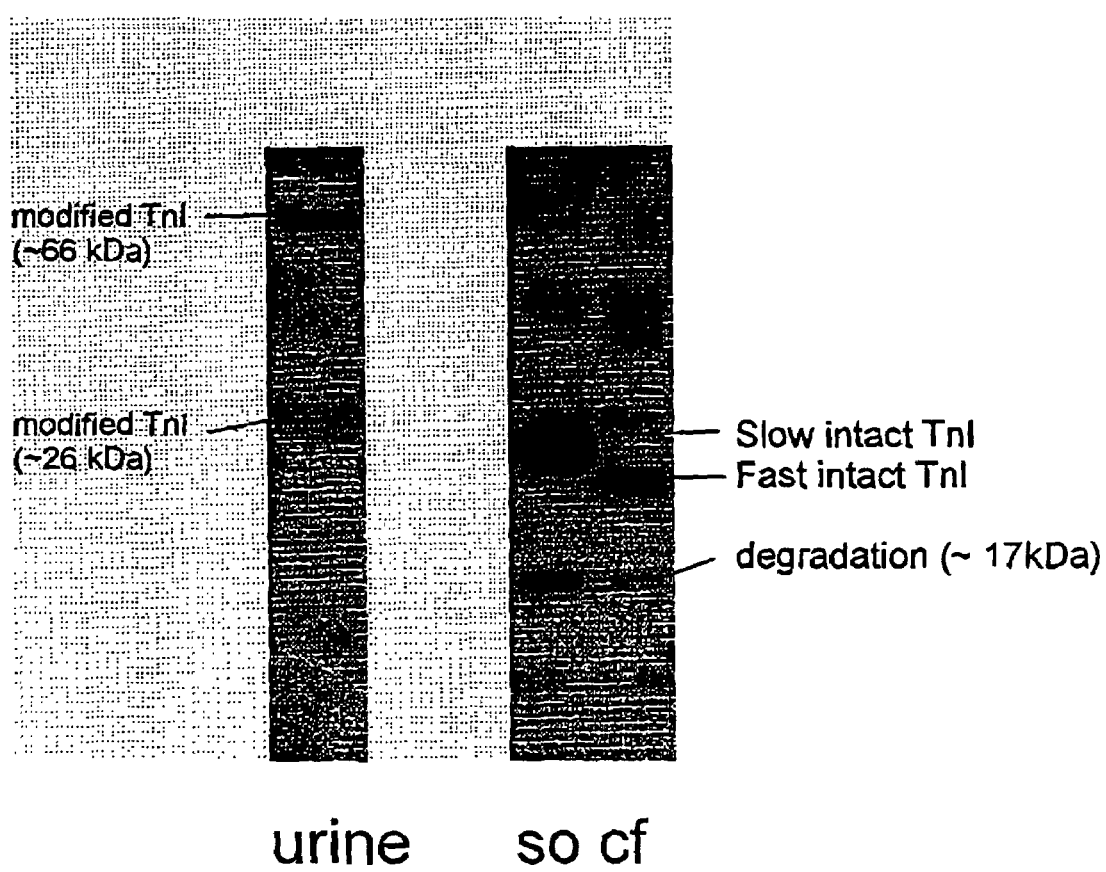

FIG. 14 shows western blots of canine urine and skeletal muscle for troponin I (TnI) using the anti-TnI MAb C5. Feline caudofemoralis (CF; fast skeletal) and the soleus (SO; slow skeletal) were used to identify the fast and slow isoforms of skeletal TnI. Several modified forms of TnI can be visualized in canine urine during severe hypoxemia.

Figure 15:
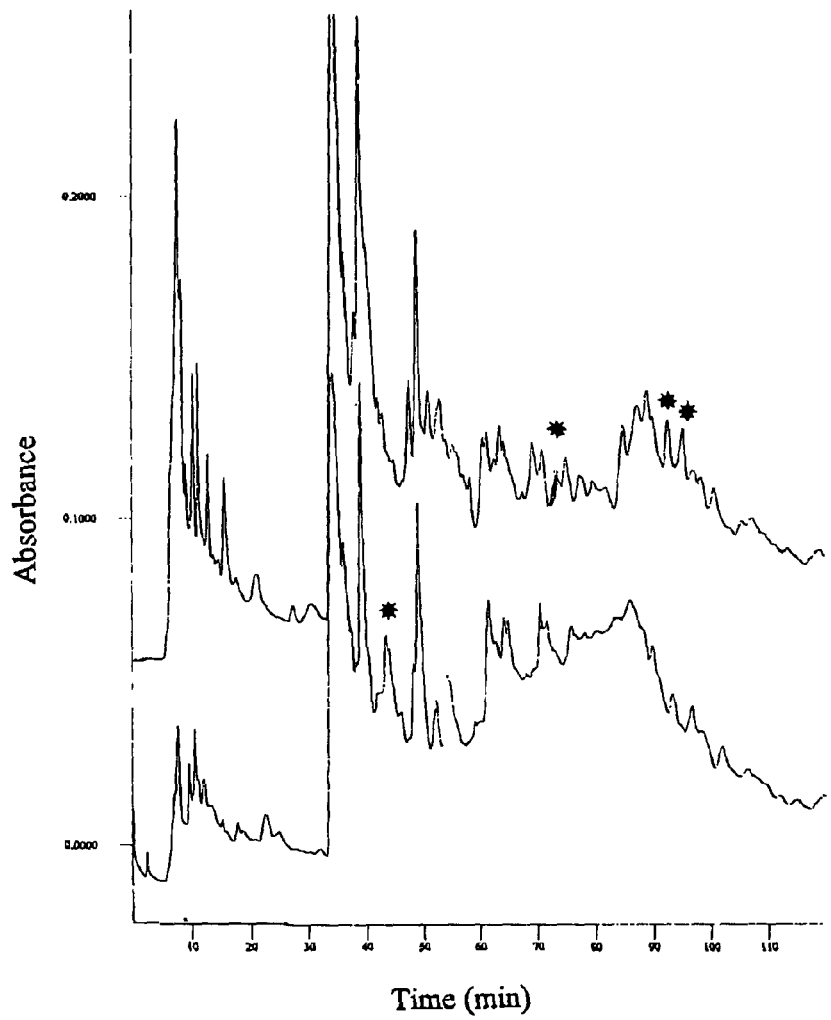

FIG. 15 shows the results of a RP-HPLC analysis of urine from a normoxic (bottom trace) and hypoxemic (top trace) dog displayed at 278 nm. Some differences are noted with an asterisk. Each peak represents one or more proteins. The proteins were eluted with a 20 min isocyanic wash (100% A) followed by a linear gradient to 110 min (72% A; 28% B) followed by another linear gradient to 120 min (20% A; 80% B). A: 0.05% aqueous TFA; B: 0.05% TFA in acetonitrile.

Figure 16:
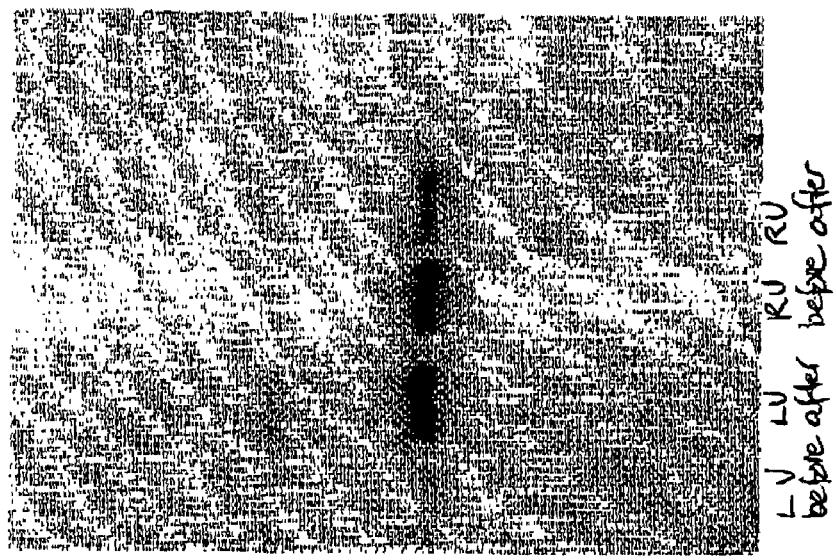
Figure 16:
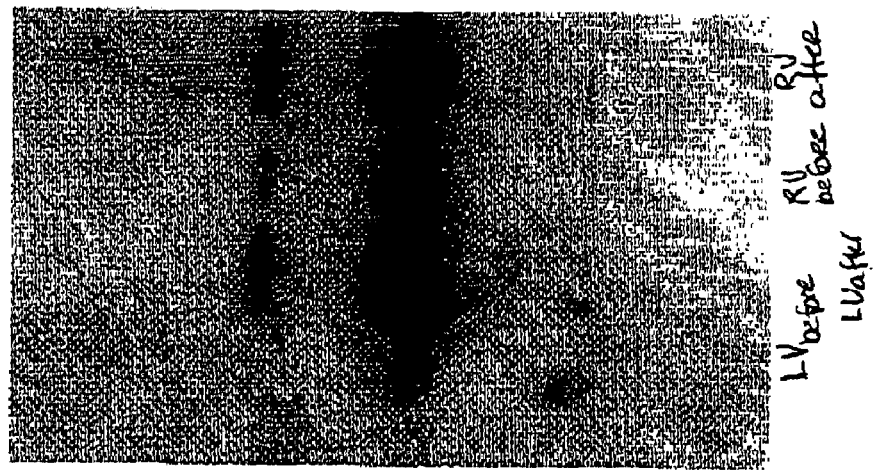

FIG. 16 shows a western blot of myocardial biopsy tissue samples taken before and following coronary bypass surgery in two human patients (panels A and B), and shows TnI modification. The biopsy samples from the left (LV) and right ventricles (RV) were immediately frozen in liquid nitrogen before the cross clamp was positioned (before) and 10 minutes following removal of the crossclamp (after). Proteins were separated by 12% SDS-PAGE and transferred to nitrocellulose for western blot analysis using the anti-cardiac TnI MAb 8I-7 (epitope TnI amino acid residues 137 to 148 (SEQ ID NO:47).

FIGS. 17A to D show complete amino acid sequences for human TnI (SEQ ID NO:8; A), rat TnI (SEQ ID NO:11; B), human TnT (SEQ ID NO:14; C) and rat TnT (SEQ ID NO:17; D) and the literature references therefor. These sequences are also compiled and are available at the website (http://genome with the extension .cs.unc.edu of the world wide web).

DETAILED DESCRIPTION

The invention is based on the discovery that the presence of one or more myofilament protein modification products in a biological sample (e.g., blood, urine, or tissue) obtained from a subject is indicative of striated muscle (i.e., skeletal and cardiac muscle) damage in the subject. The invention is further based on the discovery that the levels and types of myofilament protein modification products detected in the biological sample can be used as indicators of the extent or kind of muscle damage in the subject (e.g., mild to severe ischemia), making detection of these modification products a very useful diagnostic tool.

According to one aspect, the invention provides a method for assessing striated muscle damage in a subject by obtaining a biological sample from the subject and evaluating the sample for the presence or absence of one or more myofilament protein modification products. In one embodiment further described below, the relative amounts (i.e., levels) and types of myofilament protein modification products present in the biological sample are assessed as an indication of the extent of muscle damage in the biological sample.

As used herein, the following terms and phrases are intended to have the definitions provided below:

The phrase "myofilament protein modification product(s)" is intended to include one or more modification products of a myofilament protein associated with damage to the myocardium or skeletal muscle. For example, a myofilament protein modification produce can be a modified form of the protein or a peptide fragment of a myofilament protein such as α-actinin, a troponin (e.g., troponin I, troponin T), or myosin light chain 1. Examples of such peptide fragments include all or a portion of the carboxyl-terminal region consisting of amino acids 194 to 210 (rat sequence, see FIG. 17B, SEQ ID NO:26; corresponding human sequence, see FIG. 17A, SEQ ID NO:27) of troponin I, or all of a portion of the amino-terminal region consisting of amino acids 1 to 193 of troponin I (rat sequence, SEQ ID NO:20; corresponding human sequence, SEQ ID NO:21) (referring to the sequence published in any one of Vallins et al. 1990, FEBS Lett. 270:57-61; Armour et al. 1993, Gene, 131:287-292; or Hunkeler et al. 1991, Circ. Res. 69:1409-14). Alternatively, a myofilament protein modification product can be a peptide fragment of myosin light chain 1, such as all or a portion of the carboxyl-terminal region consisting of amino acids 20 to 199 (SEQ ID NO:28) of myosin light chain 1, or all or a portion of the amino-terminal region consisting of amino acids 1 to 19 (SEQ ID NO:29) of myosin light chain 1 (referring to the sequence published in Zimmermann et al. 1990, J. Mol. Biol. 211(3):505-513). A myofilament protein modification product can be a covalent or non-covalent complex of two or more intact proteins or fragments of proteins, such as α-actinin, troponin I, T, or C, or myosin light chain 1, or covalent or non-covalent complexes of these proteins or fragments thereof with other proteins or fragments thereof. A myofilament protein modification product can also be such a complex of peptide fragments of two or more of α-actinin, troponin I, T, or C, or myosin light chain 1, or such complexes of these proteins with other proteins or fragments thereof. Such complexes include those formed from any combination of the three troponins (troponin I, T, and C), or fragments thereof, such as, for example: TnI (amino acids 1 to 193; rat sequence, SEQ ID NO:20; corresponding human sequence, SEQ ID NO:21) with TnT (amino acids 191 to 298; rat sequence, SEQ ID NO:30; corresponding human sequence, SEQ ID NO:32); and TnI (amino acids 1 to 193; rat sequence, SEQ ID NO:20; corresponding human sequence, SEQ ID NO:21) with TnC (SEQ ID NO:48) (amino acids 1 to 94 (SEQ ID NO:49) (see Table 4).

The term "myocardial damage" is intended to include cellular damage in the myocardium as a result of hypoxia, hypoxemia, ischemia and/or ischemia/reperfusion injuries, as well as any insult or stress that activates or is associated with activation of a protease and/or a cross-linking enzyme such that modification (e.g., cross-linking, degradation) of cardiac myofilament proteins occurs. States characterized by myocardial damage include congestive heart failure, myocardial infarction, and the like.

The term "skeletal muscle damage" is intended to include cellular damage in skeletal muscle as a result of hypoxia, hypoxemia, ischemia and/or ischemic reperfusion injuries, as well as any insult or stress that activates or is associated with activation of a protease and/or a cross-linking enzyme such that modification (e.g., cross-linking, degradation) of skeletal myofilament proteins occurs. Skeletal muscle damage includes, for example, damage sustained after mechanical ventilation has resulted in atrophy of the respiratory muscles, acute (or adult) respiratory distress syndrome (ARDS) or multi-organ system failure due to, for example, sepsis, haemorrhagic shock, carbon monoxide poisoning, muscle damage stemming from surgery, or from physical effort, and the like. Skeletal muscle damage can also be associated with respiratory diseases, such as, but not restricted to, chronic obstructive pulmonary disease (e.g., emphysema, asthma, and bronchitis).

Ischemia/reperfusion injury ranges from mild to severe. The terms "mild ischemia" and "mild ischemia/reperfusion injury" refer to situations in which reversible damage to skeletal muscle or the myocardium has occurred. In these situations, the muscle can eventually regain the ability to contract and a full recovery is possible. Usually, in such situations, the majority of the cells comprising the affected muscle retain integrity of the cellular membrane. Mild myocardial ischemia and/or ischemia/reperfusion injury are marked by the presence of one or more of a cardiac troponin I modification product(s) (e.g., amino acid residues 1 to 193; rat sequence, SEQ ID NO:20; corresponding human sequence, SEQ ID NO:21), the loss of a-actinin, and the formation of covalent and/or non-covalent complex(es). It is expected that mild ischemia or ischemia/reperfusion injury of skeletal muscle will demonstrate similar myofilament protein modification products.

The terms "severe ischemia" and "severe ischemia/reperfusion injury" refer to situations where irreversible damage to skeletal muscle or the myocardium has occurred, i.e., situations where the muscle cannot regain its full ability to contract. Usually, in such situations, there is a loss of cellular membrane integrity and cellular proteins are released and necrosis occurs. Severe myocardial ischemia and/or ischemia/reperfusion injury are often marked by the presence of one or more of a myosin light chain 1 modification product(s) (e.g., amino acid residues 20 to 199), an additional TnI modification product(s) (e.g., amino acid residues 63 to 193; rat sequence, SEQ ID NO:22; corresponding human sequence, SEQ ID NO:23, amino acid residues 73 to 193; rat sequence, SEQ ID NO:24; corresponding human sequence, SEQ ID NO:25), TnT modification product(s), and α-actinin modification product(s).

Skeletal muscle ischemic or hypoxic damage is often marked by the presence of skeletal TnI modification product(s) (e.g., ~17 to 20 MW) and covalent complex formation (e.g., ~60 to 66 kDa identified by SDS-PAGE) and TnT modification product(s).

The term "ischemia" refers to anemia (lack of oxygen delivery) in a tissue due to obstruction of the inflow of arterial blood. The term "hypoxemia" refers to a state in which the oxygen pressure and/or concentration in arterial and/or venous blood is lower than its normal value at sea level (Bartels et al. 1973, *J. Appl. Physiol.* 34:549-558) and includes "hypoxia" (reduced level of oxygen in inspired gas). Hypoxemia may or may not be associated with insufficient blood flow.

The term "ischemia/reperfusion injury" refers to injury due to both ischemia, as defined above, and subsequent attempts to provide oxygen by forcing oxygenated blood through the blood vessels.

The term "biological sample" is intended to include any sample obtained from a subject which may contain a myofilament protein modification product as defined above detectable by the methods of the present invention. In one embodiment, the biological sample is a sample of a tissue derived from a subject, preferably a sample of a cardiac or skeletal muscle tissue. The sample can be a whole tissue or part of a tissue retaining the myofilament protein modification product. For example, a small biopsy tissue from a subject undergoing heart surgery can be used in the method of the invention. Alternatively, the biological sample can be a biological fluid such as whole blood, plasma, lymphatic fluid, amniotic fluid, cerebrospinal fluid, urine, and the like. Fluid extracts of tissues such as heart or skeletal muscle can also be used in the method of the present invention. The preferred biological fluid for this invention, however, is blood serum or urine.

The term "subject" is intended to include any mammal susceptible to myocardial damage (e.g., horses, dogs, humans). In a preferred embodiment, the subject is a primate. In an even more preferred embodiment, the primate is a human.

The term "obtaining" is intended to include recovery of a biological sample from a subject in a way that the myofilament protein modification product(s) is retained in a form that can be recognized by a compound specific for the myofilament protein modification product(s). Biological samples can be obtained from a subject using methods known in the art. For example, blood can be drawn from a subject suffering from congestive heart failure or a biopsy tissue can be obtained from a subject undergoing heart surgery, using standard techniques.

Assessment of myocardial or skeletal muscle damage in a biological sample can be performed by incubating the biological sample with a compound specific for one or more myofilament protein modification product(s), under conditions which allow the compound to form a complex with the myofilament protein modification product, and then detecting the complex, for example, by assaying for the presence of a label attached to the compound.

Assessment of myocardial or skeletal muscle damage in a biological sample can be performed by direct detection of myofilament protein modification product(s) in the sample, using, for example, chromatography techniques such as HPLC, or electrophoresis. These analyses are used to detect differences between elution profiles of samples obtained before and after, for example, treatment of hypoxemia, hypoxia, ischemia or ischemia/reperfusion. As well, the appearance or disappearance of one or more myofilament protein modification products, peptides, or fragments, such as, for example, cardiac TnI residues 194 to 210 (rat sequence, SEQ ID NO:26; corresponding human sequence, SEQ ID NO:27) or myosin light chain residues 1 to 199 (SEQ ID NO:28), in the elution profiles obtained during HPLC analysis can be used as indicators of muscle damage.

Prescreening of biological samples such as urine or tissue homogenates can be used to detect high (e.g., above 32 kDa) or low (e.g., below 20 kDa) molecular weight myofilament protein modification products, peptides, or fragments, in the samples, can also be performed using, for example, specific molecular weight cut-off membranes (e.g., dialysis tubing, filters). The presence one or more myofilament protein modification products, in particular TnI or TnI fragments or covalent and/or non-covalent complexes and/or an increase in the quantity of total protein (due to the presence of such complexes or proteolytic fragments) in either the high or low molecular weight fraction would indicate muscle damage.

As used herein the term "compound" is intended to include any agent which specifically recognizes and binds to an intact myofilament protein and/or a modification product thereof as defined herein. For example, the compound can be an antibody, a target protein, a peptide or a peptidomimetic, either synthetic or native, labeled or unlabeled. The term "specifically binds" means binding to a particular intact myofilament protein (e.g., troponin I) and/or a modification product thereof (e.g., cardiac TnI residues 1 to 193 (rat sequence, SEQ ID NO:20; corresponding human sequence, SEQ ID NO:21), covalent complex comprising myofilament fragments such as TnI residues 1 to 193 (rat sequence, SEQ ID NO:20; corresponding human sequence, SEQ ID NO:21) with TnT residues 191 to 298 (rat sequence, SEQ ID NO:30; corresponding human sequence, SEQ ID NO:32), or covalent complex comprising, for example, intact TnI and TnT, such as a 66 kDa complex found in skeletal muscle or human cardiac biopsy) without substantially binding to any other intact myofilament protein and/or a modification product thereof present in the biological sample. The term "antibody" as used herein encompasses all forms of antibodies known in the art, such as polyclonal, monoclonal, chimeric, recombinatorial, single chain and humanized antibodies, as well as functional fragments thereof (e.g., F(ab')$_2$ fragments), either synthetic or native, labeled or unlabeled, which specifically bind to a myofilament protein modification product. Binding between the compound and the myofilament protein modification product can be covalent or, preferably, non-covalent. When the myofilament protein modification product is a covalent complex, the compound can be a recombinant, native, or synthetic peptide or fragment thereof that recognizes a region or a portion of a region of the complex corresponding to the covalent bond.

In one embodiment, the compound is a monoclonal antibody which recognizes one or more myofilament protein modification product(s). The antibodies can be recombinant, synthetic, or native, fragments or intact, screened to recognize the myofilament protein modification product(s) of interest. Monoclonal antibodies capable of recognizing myofilament protein modification products of the invention can be prepared using methods well known in the art. Such methods are described, for example, in detail in U.S. Pat. No. 4,942,131 to Yamasaki et al., issued Jul. 17, 1990, and U.S. Pat. No. 5,583,053 to Kim, issued Dec. 10, 1996. The term "monoclonal antibody," as used herein, refers to a population of antibody molecules that contain only one species of an antigen binding site capable of immunoreacting with a particular epitope of a myofilament protein modification product. Said epitope may also be present in intact myofilament protein. A monoclonal antibody composition thus typically displays a single binding affinity for a myofilament protein modification product.

Monoclonal antibodies useful in the methods of the invention are directed to an epitope of a myofilament protein modification product, such that the complex formed between the antibody and the myofilament protein modification product can be recognized in detection assays such as ELISA, RIA etc. A monoclonal antibody to an epitope of a myofilament protein modification product can be prepared by using a technique which provides for the production of antibody molecules by continuous cell lines in culture. These include but are not limited to the hybridoma technique originally described by Kohler and Milstein (1975, *Nature* 256:495-497), and the more recent human B cell hybridoma technique (Kozbor et al. 1983, *Immunol Today* 4:72), EBV-hybridoma technique (Cole et al. 1985, *Monoclonal Antibodies and Cancer Therapy,* Alan R. Liss, Inc., pp. 77-96), and trioma techniques. Other methods which can effectively yield monoclonal antibodies useful in the present invention include phage display techniques (Marks et al. 1992, *J. Biol. Chem.* :16007-16010).

In one embodiment, the antibody preparation applied in the subject method is a monoclonal antibody produced by a hybridoma cell line. Hybridoma fusion techniques were first introduced by Kohler and Milstein (Kohler et al. 1975, *Nature* 256:495-97; Brown et al. 1981, *J. Immunol.* 127: 539-46; Brown et al. 1980, *J. Biol. Chem.* 255:4980-83; Yeh et al. 1976, *PNAS* 76:2927-31; and Yeh et al. 1982, *Int. J. Cancer* 29:269-75). Thus, the monoclonal antibody compositions of the present invention can be produced by immunizing an animal with a myofilament protein modification product. The immunization is typically accomplished by administering the myofilament protein modification product to an immunologically competent mammal in an immunologically effective amount, i.e., an amount sufficient to produce an immune response. Preferably, the mammal is a rabbit or a rodent such as a rat or a mouse. The mammal is then maintained for a period sufficient for the mammal to produce cells secreting antibody molecules that immunoreact with the myofilament protein modification product. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay. These screening methods are well known to those of skill in the art, e.g., ELISA, flow cytometry, and/or the Dipstick by Spectral Diagnostics Inc, Toronto, Canada.

A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Manassas, Va.

The resulting cells, which include the desired hybridomas, are then grown in a selective medium, such as HAT medium, in which non fused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the myofilament protein modification product antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. 1982, in: *Monoclonal Hybridoma Antibodies: Techniques And Applications,* Hurell (ed.), CRC Press, pp. 51-52). Hybridomas produced according to these methods can be propagated in vitro or in vivo (in ascites fluid) using techniques known in the art.

Monoclonal antibodies or fragments thereof suitable for use in the present invention (i.e., which recognize and specifically bind to myofilament protein modification products) can also be produced by other methods well known to those skilled in the art of recombinant DNA technology. Such alternative methods include the "combinatorial antibody display" method in which antibodies and antibody fragments having a particular antigen specificity are identified and isolated, and can be utilized to produce monoclonal anti-myofilament protein modification product antibodies (for descriptions of combinatorial antibody display see e.g., Sastry et al. 1989, *PNAS* 86:5728; Huse et al. 1989, *Science* 246:1275; and Orlandi et al. 1989, *PNAS* 86:3833). After immunizing an animal with a myofilament protein modification product immunogen as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers corresponding to a conserved 3' constant region primer can be used for PCR amplification of the heavy and light chain variable regions from a number of murine antibodies (Larrick et al. 1991, *Biotechniques* 11:152-156). A similar strategy can also been used to amplify human heavy and light chain variable regions from human antibodies (Larrick et al. 1991, *Methods: Companion to Methods in Enzymology* 2:106-110).

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System,* catalog no. 27-9400-01; and the Stratagene SurfZAP™ phage display kit, catalog no. 240612), examples of methods and reagents particularly amenable for use in generating a variegated anti-myofilament protein modification product antibody display library can be found in, for example, Ladner et al., U.S. Pat. No. 5,223,409; Kang et al., International Publication No. WO 92/18619; Dower et al., International Publication No. WO 91/17271; Winter et al., International Publication WO 92/20791; Markland et al., International Publication No. WO 92/15679; Breitling et al., International Publication WO 93/01288; McCafferty et al., International Publication No. WO 92/01047; Garrard et al., International Publication No. WO 92/09690; Ladner et al., International Publication No. WO 90/02809; Fuchs et al. 1991, *Bio/Technology* 9:1370-1372; Hay et al. 1992, *Hum Antibod Hybridomas* 3:81-85; Huse et al. 1989, *Science* 246:1275-1281; Griffths et al. 1993, *EMBO J* 12:725-734; Hawkins et al. 1992, *J Mol Biol* 226:889-896; Clackson et al. 1991, *Nature* 352:624-628; Gram et al. 1992, *PNAS* 89:3576-3580; Garrad et al. 1991, *Bio/Technology* 9:1373-1377; Hoogenboom et al. 1991, *Nuc Acid Res* 19:4133-4137; and Barbas et al. 1991, *PNAS* 88:7978-7982.

In an alternative embodiment, the compound is a peptide or a peptidomimetic. As used herein, the term "peptide" encompasses any protein or protein fragment which specifically recognizes and binds a myofilament protein modification product. For example, the peptide can be derived from a troponin C protein. As used herein, the term "peptidomimetic" is intended to include peptide analogs which serve as appropriate substitutes for peptides in interactions with, e.g., receptors and enzymes. The peptidomimetic must possess not only affinity, but also efficacy and substrate function. That is, a peptidomimetic exhibits function(s) of a peptide, without restriction of structure. Peptidomimetics of the present invention, i.e., analogs of peptides which specifically bind to myofilament protein modification products, include amino acid residues or other moieties which provide the functional characteristics described herein. Peptidomimetics and methods for their preparation and use are described in Morgan et al. 1989, "Approaches to the discovery of non-peptide ligands for peptide receptors and peptidases," In *Annual Reports in Medicinal Chemistry* (Virick, F. J., ed.), Academic Press, San Diego, Calif., pp. 243-253.

Prior to incubation with the biological sample and complexing with a myofilament protein modification product in the sample, the compound can be immobilized on a suitable solid phase surface by various methods known to those skilled in the art. The solid surface can be selected from a variety of materials including plastic tubes, beads, microtiter plates, latex particles, magnetic particles, cellulose beads, agarose beads, paper, dipsticks, and the like. The methods for immobilizing the compound are not narrowly critical, and could include passive absorption, covalent linkage, physical trapping, and the like. In general, the compound can be absorbed onto the solid support as a result of hydrophobic interactions between non-polar protein substructures and non-polar support matrix material.

As used herein the language "label" is intended to include any observable or measurable moiety which can be directly or indirectly attached to a complex formed between the compound and the myofilament protein modification product so that the complex can be detected.

For example, the label can be a direct label which, in its natural state, is readily visible, either to the naked eye, or with the aid of an optical filter and/or applied stimulation, e.g. U.V. light to promote fluorescence. Examples of coloured labels, which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dye latex such as described by May, supra, Snyder (EP-A) 280 559 and 0 281 327); or dyes encapsulated in liposomes as described in Campbell et al. (U.S. Pat. No. 4,703,017). Other direct labels include a radionucleotide, a fluorescent moiety or a luminescent moiety. In addition to these direct labelling devices, indirect labels including enzymes can also be used according to the present invention. Various types of enzyme linked immunoassays are well known in the art, for example, alkaline phosphatase, horseradish peroxidase, luciferase, beta-galactosidase, lysozyme, glucose-6-phosphate dehydrogenase, lactate dehydrogenase, and urease. These immunoassays and others have been discussed in Engvall et al. 1980, Enzyme Immunoassay ELISA and EMIT, *Methods in Enzymology,* 70:419-439 and in U.S. Pat. No. 4,857,453.

Reagents for assessing the extent of myocardial damage in a biological sample obtained from a subject can be assembled in a kit suitable for commercial manufacture and sale. The kit can include, e.g., in separate containers, compounds specific for myofilament protein modification products and reagents appropriate for the formation and detection of the complex formed between the compound and the myofilament protein modification product. The compound can be an antibody, peptide or peptidomimetic. The compound in the kit can also be immobilized on a solid phase and can be labelled. If an enzyme label is used, the kit can further include the enzyme substrate. The kit can still further include appropriate standards, positive and negative controls and instructions for performing the assay. In other embodiments the kit can include any items and/or reagents required for direct detection of myofilament protein modification product(s) using, for example, HPLC or molecular sieve techniques.

In yet another embodiment, the invention provides a method for screening for an agent which modulates the level of a myofilament protein modification product present in a biological sample. The method involves providing a biological sample containing a myofilament protein modification product, from a subject, contacting at least a portion of the biological sample with a test agent and determining the effect of the test agent on the level of the myofilament protein modification product in the so-contacted biological sample.

As used herein the term "test agent" is intended to include an agent that modulates the levels of a myofilament protein modification product in a biological sample, such as a calcium sensitizer. Such agents can be, for example, a drug, an antibiotic, an enzyme, a chemical compound, a mixture of chemical compounds, a cardioplegic solution, a biological macromolecule, and analogs thereof.

The level of the myofilament protein modification product can be determined using a compound which binds specifically to the myofilament protein modification product, using the methods described above.

In many drug screening programs which test libraries of modulating agents and natural extracts, high throughput assays are desirable in order to maximize the number of modulating agents surveyed in a given period. Assays which are performed in cell-free systems, such as may be derived with cardiac muscle cell extracts, or from purified or recombinant proteins and/or peptides, are preferred as "primary" screens in that they can be generated to permit rapid development and relatively easy detection of an alteration in the level of a myofilament protein modification product, which is mediated by a test modulating agent. Moreover, the effects of cellular toxicity and/or bioavailability of the test modulating agent can be generally ignored in the in vitro system, the assay instead being focussed primarily on the effect of the test agent on the levels of a myofilament protein modification product(s).

The invention thus provides for the use of myofilament protein modification products in drug screening tests and tests for assessing the efficacy of treatments and interventions on patients that experience muscle dysfunction due to hypoxia, hypoxemia, ischemia, and/or reperfusion damage. Further, transgenic animals or cell lines expressing or transfected with one or more myofilament protein modification products could be used to mimic hypoxic, hypoxemic, ischemic and/or reperfusion damage, and provide valuable tools for carrying out such screening tests and evaluation of treatments. In addition, in vitro assays with purified proteins, peptides, or fragments, isolated myofilaments, cells, or skinned muscle fibers in which one or more myofilament protein modification product(s) is present can similarly be used.

The efficacy of test agents can be assessed by generating dose response curves from data obtained using various concentrations of the test modulating agent. Moreover, a control assay can also be performed to provide a baseline for comparison. In the control assay, the biological sample containing a myofilament protein modification product is incubated in the absence of a test agent.

In a preferred embodiment, the agent being screened for is a calcium sensitizer, (i.e., an agent that increases the sensitivity of striated muscle cells to calcium).

In yet another aspect, the invention provides a method for assessing the extent (e.g., mild to severe, as defined herein) or type (e.g., reversible or irreversible, as defined herein) of skeletal muscle or myocardial damage in a biological sample obtained from a subject. The method involves obtaining a biological sample from the subject, and incubating the biological sample with at least one compound (e.g., antibody) which specifically binds to one or more different myofilament proteins or myofilament protein modification products present in the sample, under conditions which allow the compound to form one or more complexes with the myofilament proteins or myofilament protein modification products. The method further involves detecting formation of the complexes and then characterizing the profile of the one or more myofilament proteins or myofilament protein modification products contained in the complexes as an indication of the extent or type of skeletal muscle or myocardial damage in the subject.

In certain embodiments, the formation of complexes is detected using ELISA, RIA, immunoblot ("western blot") analysis, HPLC analysis, or PAGE analysis (SDS or native). These methods are known in the art and are described below in the "Examples" section.

Characterizing the profile of different myofilament proteins or myofilament protein modification products (which can be from the same or from different myofilament proteins) can be achieved either qualitatively or quantatively. Qualitative characterization involves comparing the sizes of the proteins and modification products and quantative characterization involves quantifying and comparing their relative amounts.

For example, when qualitatively characterizing different myofilament proteins and/or modification products present in the biological sample, antibodies can be used which differentially recognize epitopes present in the various modification products. Using a label that has a measurable moiety attached to it (e.g., β-galactosidase), a profile or "fingerprint" of the proteins and modification products can be obtained. This profile, which is expected to include, for example, characteristic ratios of various proteins and/or fragments from the same (e.g., cardiac TnI residues 1 to 193 (rat sequence, SEQ ID NO:20; corresponding human sequence, SEQ ID NO:21) vs. cardiac TnI residues 63 to 193 (rat sequence, SEQ ID NO:22; corresponding human sequence, SEQ ID NO:23)) from different (e.g., TnI vs. myosin light chain I) proteins, can then be associated with a level (i.e., extent) or type of myocardial damage.

Different myofilament proteins and/or modification products present in the biological sample can also be quantitatively characterized (e.g., compared to a standard). For example, levels of different troponin I modification products (e.g., a cardiac troponin I fragment consisting of amino acids 1 to 193 (rat sequence, SEQ ID NO:20; corresponding human sequence, SEQ ID NO:21)) can be compared to one another, or to levels of the intact troponin I protein, and this pattern of protein levels can be associated with a level (i.e., extent) or type of myocardial damage. Levels of myofilament proteins and/or modification products can be detected using for example quantifiable labels (e.g. antibodies labeled with an enzyme, the activity of which can be measured and correlated with levels of antibody binding), as are known in the art, which specifically bind to the proteins and/or modification products.

In one embodiment, the method of the invention is used to diagnose mild ischemia by detecting the presence of skeletal or cardiac troponin I fragment (e.g., cardiac TnI residues 1 to 193 (rat sequence, SEQ ID NO:20; corresponding human sequence, SEQ ID NO:21)) and comparing the levels of this fragment to the levels of intact troponin I.

As the invention shows linkage or correlation between the modifications of specific myofilament proteins and the degree of myofilament/muscle damage that has occurred, the profile at a given time point of the specific modifications to several myofilament proteins provides an indication of the extent of muscle damage that has occurred. Both the type of modification of a particular protein(s) and the quantity of a particular protein modification product(s) change over time, and can be used to characterize the level of damage that has occurred.

For example, we describe herein that the extent and type of modification to TnI (amino acid residue 1 to 210 of rat TnI (SEQ ID NO:11); corresponding human sequence depicted in SEQ ID NO:8) change depending on whether mild or severe ischemic damage has occurred. With mild ischemia and/or ischemia/reperfusion, TnI is specifically degraded, yielding a fragment with apparent molecular weight of 22 kDa by SDS-PAGE, corresponding to amino acid residues 1 to 193 (rat sequence, SEQ ID NO:20; corresponding human sequence, SEQ ID NO:21), due to proteolysis of 16 amino acid residues form the C-terminus of TnI. In addition (or shortly thereafter), TnI 1 to 193 (rat sequence, SEQ ID NO:20; corresponding human sequence, SEQ ID NO:21) forms covalent complexes with TnC or TnT (32 kDa by SDS-PAGE). Later, with increasing severity of ischemic and/or ischemic/reperfusion damage, TnI is further degraded, yielding smaller fragments TnI 63 to 193 (rat sequence, SEQ ID NO:22; corresponding human sequence, SEQ ID NO:23) and 73 to 193 (rat sequence, SEQ ID NO:24; corresponding human sequence, SEQ ID NO:25) (16 and 15 kDa by SDS-PAGE. Therefore, if a profile from a biological sample shows only a 22 kDa TnI protein fragment, rather than both a 22 kDa and a 16 kDa TnI fragment, the indication is that mild/reversible rather than severe/irreversible damage has occurred.

Different myofilament proteins are more or less susceptible to modification depending on the extent of ischemic or ischemic/reperfusion injury that has occurred. Thus, the appearance of a certain modification to a specific proteins can be used as a marker/index for extent of muscle damage. For example, MLC1 degradation (residues 20-199) occurs only with very severe ischemia in the myocardium. Therefore, if one detects this smaller fragment of MLC1 in a biological sample, it is an indication that the myocardium is severely and possibly irreversibly damaged.

Moreover, it is useful to study in parallel the profiles presented by different myofilament proteins and their products. By monitoring several proteins simultaneously, and determining the quantity and quality of the various species of these proteins, a finer analysis, and potentially more accurate assessment, can be made. The quantity as well as the appearance of the various modifications in a particular sample type is expected to be diagnostic for each increment along the pathway from mild to severe muscle damage. For example, in a tissue sample from myocardium, the following changes would be expected over time as severity of injury increased:

1. TnI degradation product residues 1 to 193 (rat sequence, SEQ ID NO:20; corresponding human sequence, SEQ ID NO:21) and loss of α-actinin.
2. TnI or TnI 1 to 193 (rat sequence, SEQ ID NO:20; corresponding human sequence, SEQ ID NO:21) covalent complex formation. (As proteolysis and covalent complex formation may occur very rapidly the two species may thus be indistinguishable from one another.)
3. TnI further degraded (Residues 63 to 193 (rat sequence, SEQ ID NO:22; corresponding human sequence, SEQ ID NO:23)).
4. TnI further degraded (Residues 73 to 193 (rat sequence, SEQ ID NO:24; corresponding human sequence, SEQ ID NO:25)).
5. TnT degradation.
6. MLC1 degradation (residues 20-199).
7. Appearance of these protein species in blood, as opposed to only in the myocardium tissue sample. It is expected that these proteins and protein modification products would also be observed in urine at this level of severity of damage.

The invention is further illustrated by the following examples, which should not be construed as further limiting. The contents of all references, pending patent applications, and published patents cited throughout this application are hereby expressly incorporated by reference.

EXAMPLES

I. Rat Cardiac Muscle

Preparation of Global Ischemic Model for Isolated Rat Hearts

To prepare a model of globally ischemic rat hearts, rats (250 to 350 g) were anaesthetized with ether, the hearts were excised and quickly placed in 2.5 ml of saline within an airtight plastic bag for 60 minutes at 4° C. (control) or 37° C. as described in Westfall et al. 1992, *Circ. Res.* 70:302-13. The left ventricle was removed and myofilaments isolated as described in Rarick et al. 1996, *J. Biol. Chem.* 271:1039-1043. A cocktail of protease inhibitors (50 μM phenyl methylsulfonyl fluoride, 3.6 μM leupeptin and 2.1 μM pepstatin A) was used at all steps of the isolation procedure. Isolated myofilaments were stored at −70° C. until preparation for SDS-PAGE analysis.

Perfusion of Isolated Rat Hearts

Cardiac function was measured in a non-recirculating Langendorff perfusion apparatus. Rats (250 to 350 g) were anaesthetized with sodium pentobarbital (50 mg/kg) and injected with heparin (200 units) before the heart was excised. The hearts were quickly excised and placed in ice cold saline. The aorta was cannulated with a 1.6 mm glass cannula (Radnoti Glass Inc.) and perfused in a non-recirculating apparatus with heart chamber (Radnoti Glass Inc.) at a coronary flow of 14 ml/min with Krebs Ringer bicarbonate buffer equilibrated with 95% $O_2$ and 5% $CO_2$ at 37° C. The Krebs Ringer bicarbonate buffer consisted of 100 mM sodium chloride, 4.74 mM potassium chloride, 1.18 mM potassium dihydrogen phosphate, 1.18 mM magnesium sulfate, 1.15 mM calcium chloride, 25 mM sodium bicarbonate, 11.5 mM glucose, 4.92 mM pyruvate and 5.39 mM fumarate, pH 7.4. The hearts were paced at 360 beats per minute. All hearts were equilibrated with Krebs Ringer bicarbonate buffer for 15 minutes prior to the experimental protocols described below. Hearts were subjected to either continuous flow for 45 minutes (control), 15 minutes no-flow ischemia, or 60 minutes no-flow ischemia with or without 45 minutes of reperfusion. No-flow ischemia was produced by wrapping the hearts in an impermeable plastic bag and submerging them in a water bath at 37° C. The left ventricular pressure was measured with a pressure transducer. Left ventricular pressures were 61.5±7.5 mm Hg during the 10 min equilibration period and 78.8±8.0 mm Hg after 45 min of perfusion. The pressure during reperfusion was 90.2±17.3 and 133.5±29.1 mm Hg following 15 min of ischemia and 60 min of ischemia, respectively.

Tissue and Effluent Sample Preparation

Fractions were collected at the end of the equilibration period. During reperfusion and the 45 minutes of perfusion (control), fractions were collected either every minute for 10 minutes, then every three minutes for the remainder of the protocol, or as entire effluent samples. The fractions were frozen immediately at −70° C. to −80° C. and then stored frozen or lyophilized. The left ventricles were frozen in liquid nitrogen and stored at −70° C. until analyzed.

Skinned Fiber Bundle Experiments

Figure 1:
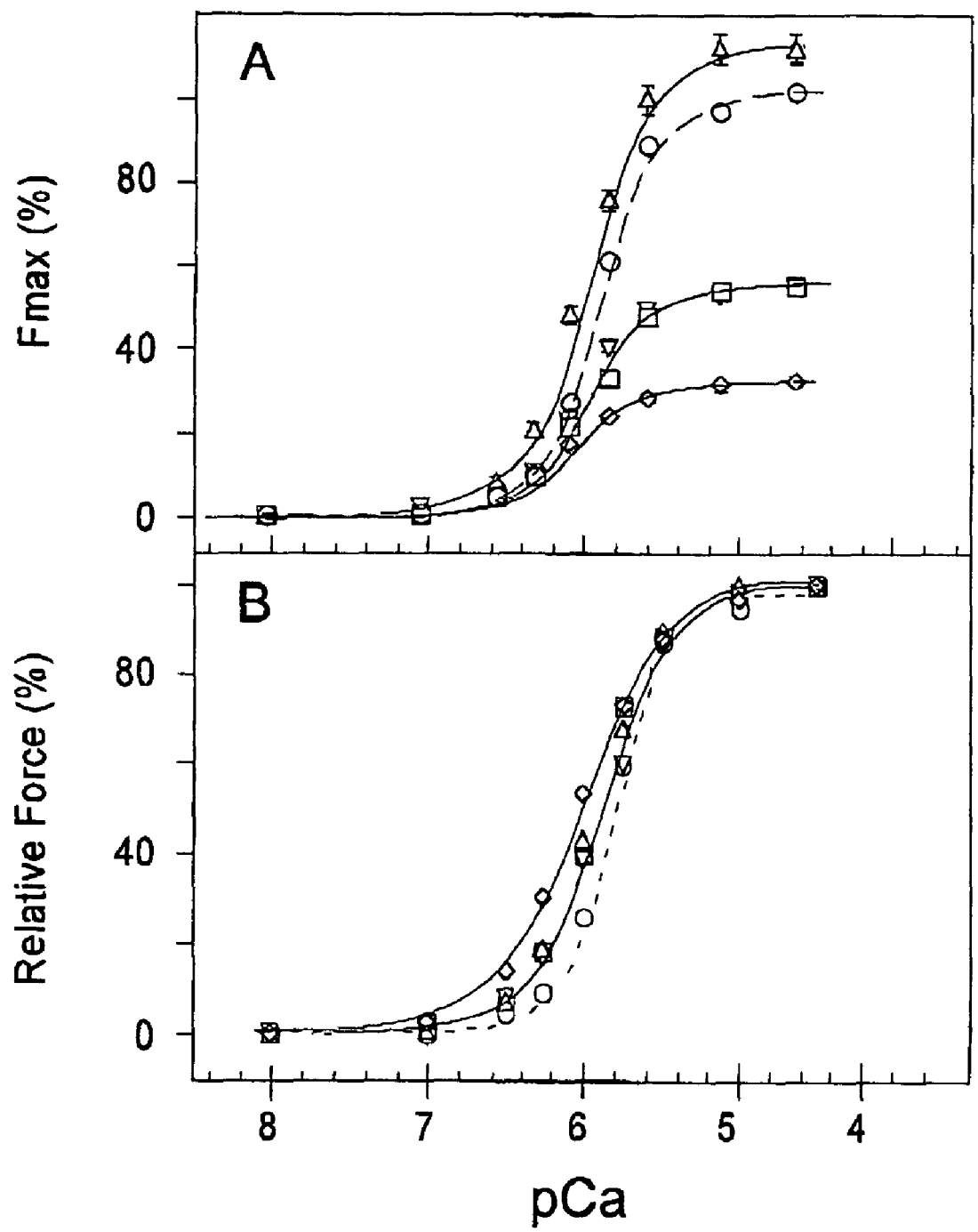
FIG. 1 is a graph showing the effect of reperfusion on the isometric force/pCa relation of Triton X-100 skinned cardiac muscle fiber bundles obtained from isolated rat hearts that experienced increasing durations of ischemia. Isometric force was measured as a function of increasing calcium concentrations for each skinned trabecula muscle bundle obtained from rats which had undergone 15 min of equilibrium followed by: 45 min of perfusion (control n=4, ○), 15 min ischemia (n=4, △), 15 min ischemia followed by 45 min of reperfusion (n=4, ▽), 60 min of ischemia (n=4, □) or 60 min ischemia followed by 45 min reperfusion (n=6, ◇). Force is plotted as the percent of either the maximum force produced by the control skinned muscle fiber bundles (Fmax=force of fiber/maximum calcium-dependent force of control fiber bundle (100%), panel A) or as the relative force (maximum calcium-dependent force of the fiber bundle=100%, panel B) with respect to changing calcium concentration. The experimental protocols of the Langendorf perfusion and skinned muscle fiber bundle analysis are described below. Data are presented as ±SEM for skinned fibers obtained from 4 to 6 rat hearts for each experimental condition. Where the error bars are not shown, the standard error is small and lies within the symbol.

Hearts removed from the Langendorff perfusion apparatus were immediately placed in cold relaxing buffer [0.1 mM ethylene glycol bis (β-amino ethyl ether)-N,N,N',N',-tetraacetic acid (EGTA), 2 mM magnesium chloride, 79.2 mM potassium chloride, 5.4 mM ATP, 12 mM creatine phosphate, 20 mM 3-(M-morpholino) propanesulfonic acid (MOPS), pH 7.0 (ionic strength 150 mM)] plus the protease inhibitor cocktail. Trabelculae were quickly dissected from the heart and placed in 50% (v/v) glycerol and relaxing buffer, protease inhibitor cocktail and 10 mM butanedione monoamine. The trabeculae were used in skinned fiber bundle experiments within a week. The remaining left ventricle was frozen on dry ice and stored at −80° C. The fiber bundles (about 100 μm in diameter) from each rat were glued to a force transducer at one end and to a fixed post attached to a micro-manipulator. The fibers were skinned in relaxing buffer containing 10 UI/ml creatine kinase and 1% Triton X-100 for 30 minutes. The fibers were transferred to relaxing buffer containing 10 IU/ml creatine kinase and the sarcomere lengths set at 2.2 μm, based on the laser diffraction pattern. Isometric pCa-force relations were determined by bathing the skinned fiber bundles sequentially in solutions [10 mM EGTA, 2 mM magnesium chloride, 79.2 mM potassium chloride, 5.4 mM magnesium ATP, 12 mM creatine phosphate, 10 IU/ml creatine kinase, 20 mM MOPS, pH 7.0 (ionic strength 150 mM)] that contained increasing concentrations of calcium chloride to achieve pCa values from 8.0 to 4.5. All results, shown in FIG. 1, are presented as mean±standard error. Data were linearized using the Hill transformation and the force/pCa relation fitted to the A. V. Hill equation using nonlinear regression analysis to derive the $pCa_{50}$ value and Hill coefficient. Shifts in the $pCa_{50}$ value were analyzed with an unpaired student's t-test with significance set at p<0.01. The total protein for each skinned fiber bundle was determined using the Lowry assay (Lowry et al. 1964, *J. Biol. Chem.* 193:265-275). At the same fiber bundle length, relative tension expressed as force/cross-sectional area (average of controls about 50 mN/mm$^2$) was similar to force/mg protein. This allowed an alternative comparison and analysis of relative tension generated by fiber bundles from different rat heart preparations with different treatments. In the figures, tension is normalized to the maximum tension of control preparations. FIG. 1 and Table 1 show the results obtained from this assay, which indicate that ischemia alone induces myofilament dysfunction and that reperfusion or increasing duration of ischemia further aggravates myofilament dysfunction.

SDS-PAGE and Western Blot Analysis of Tissue and Effluent Samples

Left ventricular tissue samples following Langendorf perfusion were skinned in 50% (v/v) glycerol and relaxing buffer containing protease inhibitor cocktail. The myofibrils from the global ischemia model and the left ventricular tissue were homogenized in 160 mM Tris, pH 8.8 plus the protease inhibitor cocktail. The protein content of the homogenate was determined using the Lowry assay. Homogenized samples were diluted two-fold with sample buffer consisting of 2% SDS, 5 mM Tris, pH 6.5, 20% sucrose, 0.05% bromophenol blue and 1 mM β-mercaptoethanol. Effluent samples used for SDS PAGE analysis were dialyzed against 1 mM hydrochloric acid, 1 mM β-mercaptoethanol with dialysis bags having a molecular weight cut off of 6000 daltons. The samples were then freeze-dried and taken up into 50 μl of 160 mM Tris, pH 8.8 plus the protease inhibitor cocktail and diluted two fold with gel dissolving buffer. Tissue samples (30 μg of total protein) and effluent samples (20 μg of total protein) were loaded on a 12.5% SDS polyacrylamide gel using a Hoeffer (Baie D'Urfé, Canada) or Biorad (Hercules, Calif.) mini-gel apparatus. Homogenized tissue samples, effluent samples, and RP-HPLC peaks collected from the affinity columns (see below) were separated by 12.5% SDS-PAGE, or by a modified tricine-SDS-PAGE system (T-PAGE) (Schagger et al. 1987, *Anal. Biochem.* 166:368-79) using the Mini-gel system (Biorad). T-PAGE was performed with a 10% T (total acrylamide concentration), 3% C (concentration of bis-acrylamide) resolving gel and 4% T, 3% C stacking gel, containing 6 M urea, 0.1% SDS, 1 M Tris-HCl, pH 8.45 (urea T-PAGE). The cathode running buffer consisted of 0.1 mol/l Tris-HCl pH 8.25, 0.1 mol/l tricine, 0.1% SDS, and the anode buffer consisted of 0.2 mol/l Tris-HCl pH 8.9. Samples were diluted 2 fold with sample buffer containing 2% SDS, 5 mmol/l Tris-HCl, pH 6.5, 20% sucrose, 0.05% bromophenol blue, with 100 mmol/l β-mercaptoethanol (β-ME) for SDS-PAGE, or with 6 mol/l urea and 100 mmol/l β-ME for urea T-PAGE. Samples were boiled for 5 min, loaded onto the gel, and run at 105 V for 1 to 1.5 h. Gels were transferred to nitrocellulose or PUDF using a wet transfer apparatus (Biorad) with 10 mmol/l 3-cyclohexylamino-1-propanesulfonic acid (CAPS), pH 11.0 for 16 h at 27 mA or 60 min at 100 V, at 4° C., or stained with Coomassie Blue and silver (Coligan et al. 1995, *Current protocols in protein science*. John Wiley & Sons, New York). Proteins were quantified on the stained gel or western blot by densitometric scanning using an Ultrascan XL enhanced Laser densitometer (Pharmacia LKB Biotechnology, Uppsala, Sweden) or by Corel Photohouse (version 8).

Western blot analysis was done according to Van Eyk et al. 1998 (*Circ. Res.* 82:261-71) or else the primary antibodies were detected with goat anti-mouse IgG conjugated to alkaline phosphatase (Jandel Scientific) and CDP-Star chemiluminesence reagent (NEN-Mandel). The monoclonal antibodies used were anti-TnT clone JLT-12 (Sigma Chemical Co., St. Louis, Mo.), anti-α-actinin clone EA-53, (Sigma) or anti-α-actinin clone 157 (provided by Spectral Diagnostics, Toronto, Canada), anti-MLC1 (provided by Abbott Laboratories, Chicago, Ill.) which recognizes amino acid residues 70 to 75 (SEQ ID NO:40), anti-TM (Sigma), anti-sarcomeric actin (Sigma), and anti-glyceraldehyde phosphate dehydrogenase (Cedarline Lab. Ltd, Canada). Several different anti-TnI antibodies were utilized: anti-TnI clone 3309 which recognizes amino acid residues 157 to 192 (SEQ ID NO:41) and clone AM-NI which recognizes TnI residues 1 to 65 (SEQ ID NO:42) (provided by Dr. J. Ladenson, Washington University St. Louis, Mo.), anti-TnI clone 10F2 (MAb 10F2) which recognizes amino acid residues 189 to 199 (SEQ ID NO:43) (see epitope map FIG. 8 in Van Eyk et al. 1998, *Circ. Res.* 82:261-71), antibody provided by Dr. C. Larue at Univ. Innsbruck Med. School, Austria, MAb C5 (Research Diagnostics, Flanders, NS), and our anti-TnI peptide (P143T) residues 137 to 148 (SEQ ID NO:44) (MAb E2). The production of the anti-TnI peptide monoclonal antibodies including MAb E2 has been described in Van Eyk et al. 1995 (*Prot. Sci.* 4:781-90). MAb E2 recognizes intact skeletal and cardiac TnI and cardiac TnI peptides containing amino acid residues 136 to 148 (SEQ ID NO:34) (data not shown). As well, anti-TnI antibodies MAb 8I-7 and 3I-35 (both Spectral Diagnostics, Toronto, Canada), and MAb C5 (Research Diagnostics, Flanders, NS), which recognize TnI amino acid residues 137 to 148 (SEQ ID NO:47), 188 to 199 (SEQ ID NO:39), and 188 to 199 (SEQ ID NO:39), respectively, see McDonough et al. 1998, *Biophysical J.* 74:A354). Epitope mapping of these various antibodies was carried out by 12% SDS PAGE of intact cardiac TnI and various TnI fragments followed by western blot analysis as outlined above. Bovine cardiac TnI and rabbit skeletal TnI were purified by HPLC (Ingraham et al. 1988, *Biochemistry* 27:5891-98); recombinant rat cardiac TnI fragments 54 to 210 (SEQ ID NO:36), 1 to 188 (SEQ ID NO:37), and 1 to 199 (SEQ ID NO:38) were provided by Dr. A Martin (Univ. Illinois at Chicago, Chicago, Ill.; Rarick et al. 1997, *J. Biol. Chem.* 272:26887-92), and the synthetic skeletal TnI peptide 96 to 142, which is equivalent to the cardiac peptide residues 129 to 175 (SEQ ID NO:45), was prepared by solid-phase peptide synthesis (Tripet et al. 1997, *J. Mol. Biol.* 271:728-50).

Alkaline urea PAGE was used to analyze for TnC as outlined by Head et al. 1974 (*Biochem. J.* 137:145-54). Samples were prepared in buffer containing 6 mol/l urea, 100 mmol/l β-ME, 20 mmol/l Tris-HCl pH 8.9, 3 mmol/l calcium chloride, and loaded onto the gel. The gel consisted of 8% T, 0.8% C resolving and 5% T, 0.8% C stacking gels, with 6 mol/l urea, 20 mmol/l Tris-HCl, and 124 mmol/l glycine at pH 8.6. The gel was then electrophoresed at 105 V for 1 h, and stained with Coomassie blue or silver.

Figure 3:
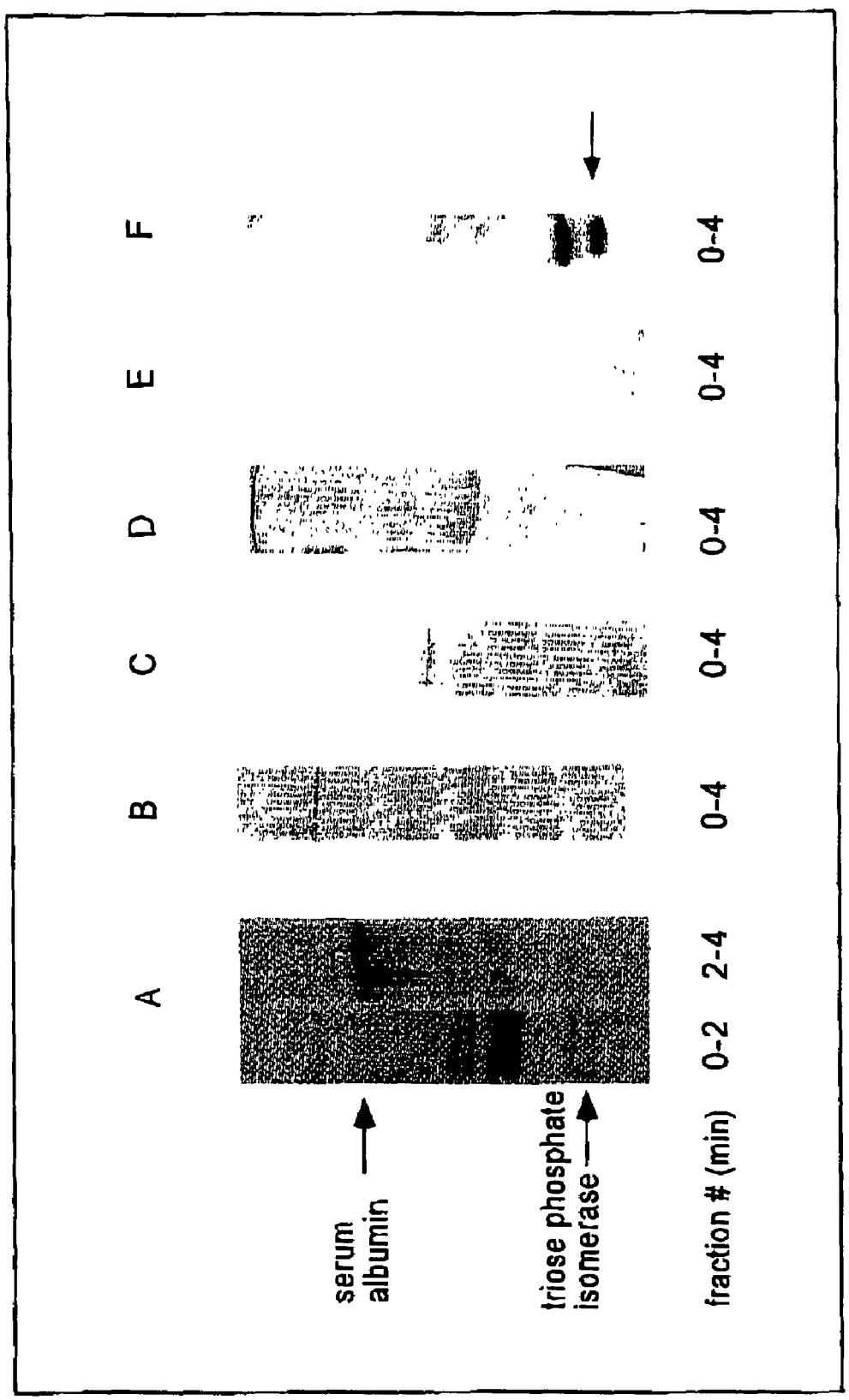
FIG. 3 shows the results of an SDS-PAGE analysis of reperfusion effluent. Reperfusion effluent was collected from rat hearts which had undergone 15 min equilibration followed by 60 min of ischemia. Panel A shows the 12.5% SDS polyacrylamide gel stained with coomassie blue of the two minute effluent fractions collected at 0 and 2 min. Serum albumin and triose phosphate isomerase were identified by amino acid sequencing (Table 2). Panels B to F show the western blots of the combined effluent fractions (0 to 4 min) probed with anti-α-actinin (panel B), anti-TnT (panel C), anti-tropomyosin (TM) (panel D), anti-TnI peptide P142T (residues 136 to 148; SEQ ID NO:34) (MAb E2, panel E) and anti-MLC1 (panel F) antibodies. The MLC1 modification product is indicated by an arrow.
Figure 4:
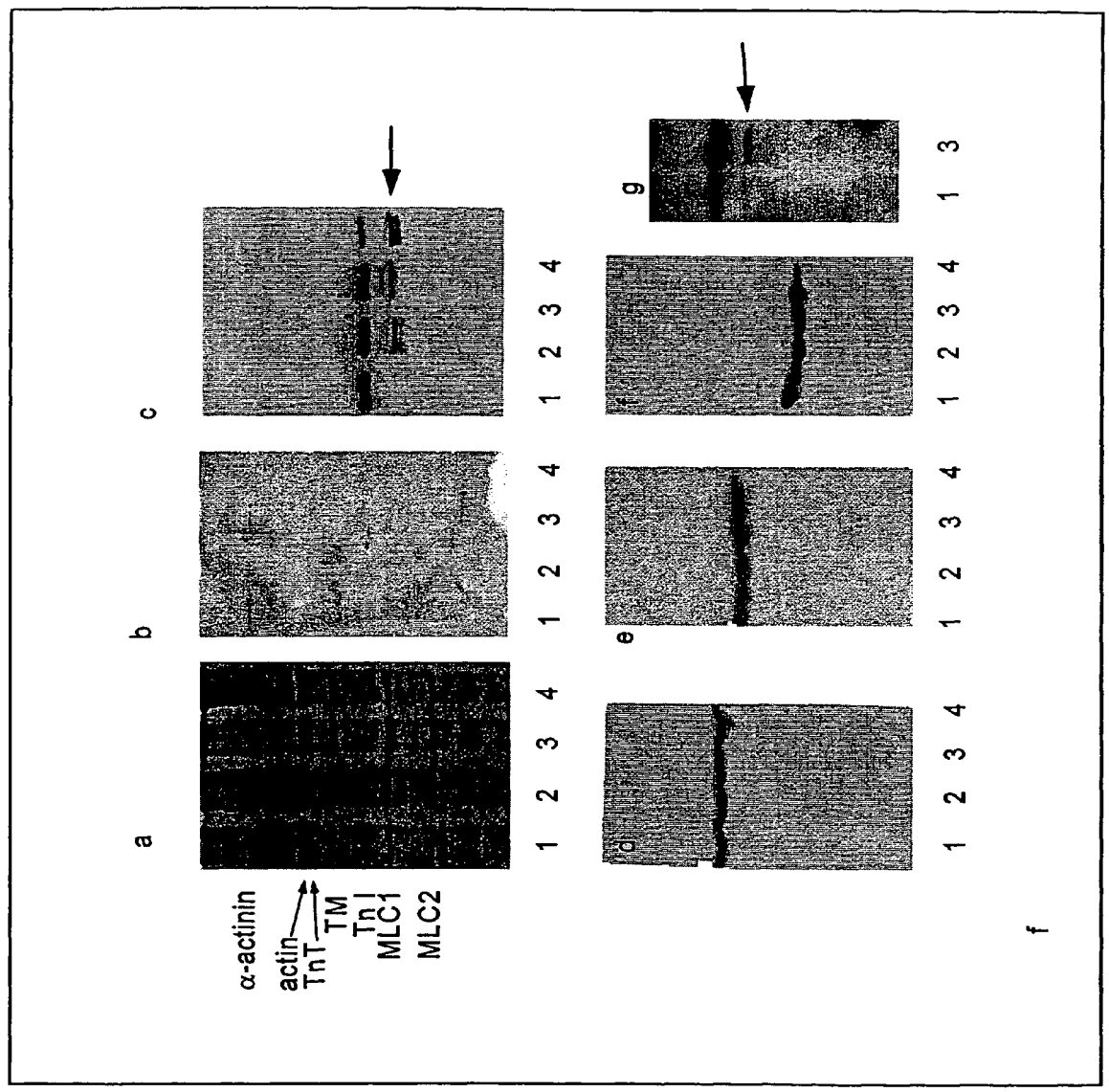
FIG. 4 shows the results of an SDS-PAGE analysis of skinned left ventricle tissue samples from isolated rat hearts. Tissue samples obtained from hearts which experienced 15 min equilibration followed by either 45 min perfusion (control, 1), 15 min ischemia followed by 45 min reperfusion (i.e., 15/45; 2), 60 min ischemia (3) or 60 min ischemia followed by 45 minutes reperfusion (i.e., 60/45; 4) were skinned in 50% glycerol prior to being prepared for SDS-PAGE analysis. Panel A shows the coomassie blue stain of the 12.5% crosslinked gel. Panels B-F show corresponding western blots using anti-α-actinin (panel B), anti-TnI peptide residues 136 to 148 (SEQ ID NO:34) (MAb E2, panel C), anti-TnT (panel D), anti-TM (panel E), and anti-MLC1 (panel F) antibodies. Panel G shows the western blot of a 10% SDS-PAGE of control tissue and tissue obtained from rats which experienced 60 min ischemia (2). The western blot was probed with anti-α-actinin antibody. Modification products are indicated by arrows.

Results of the SDS-PAGE analysis and subsequent western blots of rat heart reperfusion effluent are shown in FIG. 3, and of tissue from global ischemic rat hearts in FIG. 6, wherein MLC1 modification product is identified by an arrow (FIG. 6E). FIG. 8 and FIGS. 10C and 10D show that complexes are formed from fragments of TnI, TnT, and TnC. FIG. 4 shows the SDS-PAGE analysis and subsequent western blots of rat skinned ventricular tissue, wherein TnI modification products can be seen (FIG. 4C, arrow). Note that α-actinin was lost (FIG. 4B) with mild ischemia, and α-actinin degradation (FIG. 4G) appeared with more severe ischemia.

Amino Acid Sequencing of Tissue and Effluent Samples

Figure 5:
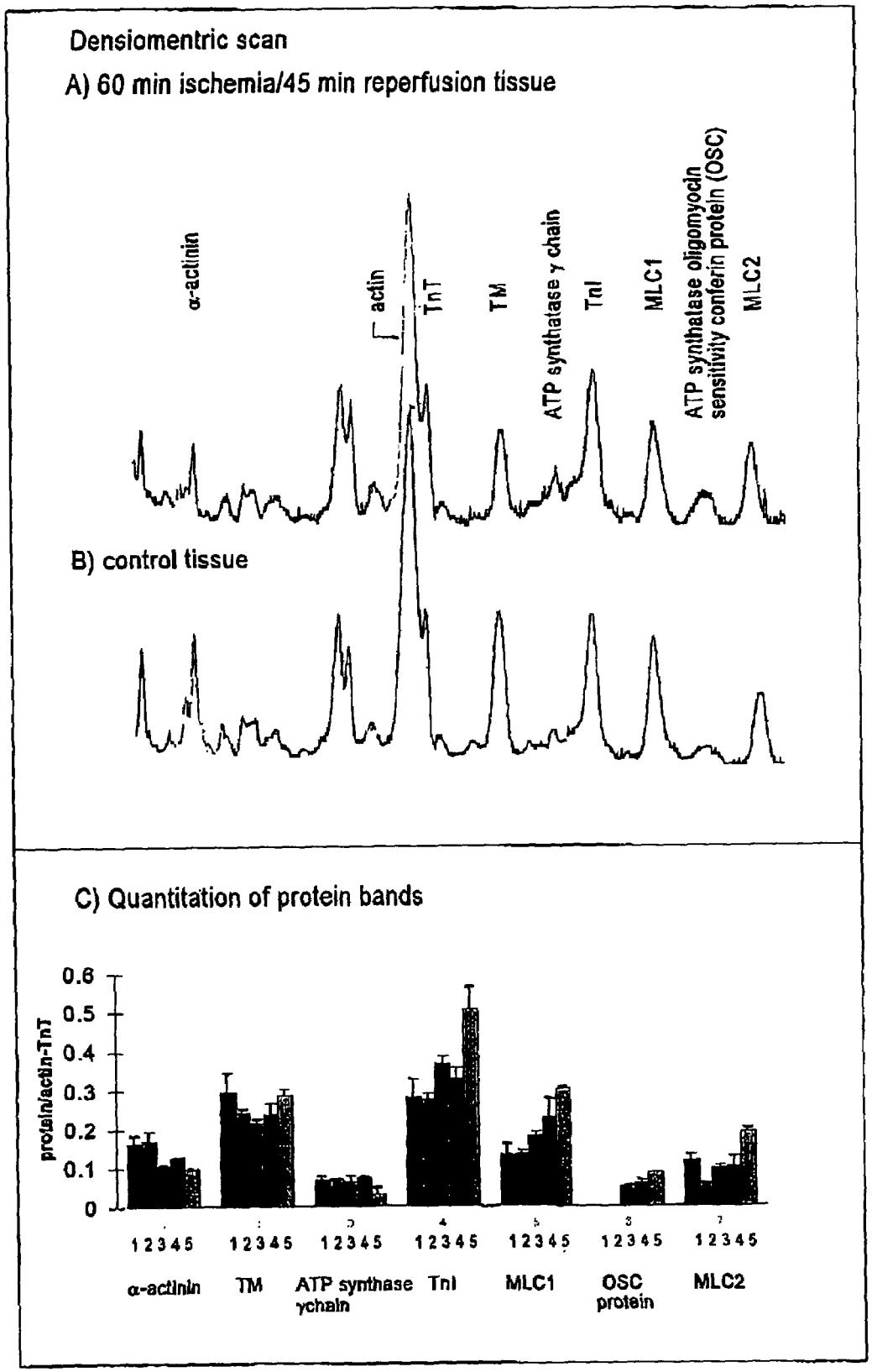
FIG. 5 shows densitometry scans of SDS-PAGE runs of skinned left ventricular tissue samples. Panels A and B show densitometric scans of a 12.5% SDS-PAGE of tissue from rat hearts that experienced 15 min equilibration followed by either 45 min perfusion (control, panel B) or 60 min ischemia followed by 45 min reperfusion (60/45, panel A). Proteins identified in panel A were identified by western blot analysis except ATP synthetase oligomyocin sensitivity conferring protein (OSC protein) and ATP synthase γ chain which were identified by amino acid sequencing. Panel C shows the quantity of protein at each corresponding peak of the densitometric scan. Tissue samples from 4 to 6 rats were analyzed for each of the following conditions: 45 min perfusion (control, lane 1), 15 min ischemia (lane 2), 15 min ischemia followed by 45 min reperfusion (15/45, lane 3), 60 min ischemia (lane 4) and 60 min ischemia followed by 45 min reperfusion (60/45, lane 5). 30 µg of total protein were loaded on each gel lane. Variation in the amounts loaded was taken into account by standardizing the quantity of each peak with respect to the quantity of TnT-actin peak.

Tissue and effluent samples were prepared and electrophoresed on a 12.5% SDS polyacrylamide gel as described above. The proteins were transferred onto a polyvinyline difluoride protein sequencing membrane (PVDF, Biorad) using 10 mM 3-(cyclohexylamino)-1-propanesulfonic acid buffer (Matsudaira et al. 1987, *J. Biol. Chem.* 262:10035-41) at 100 mA for 55 min using a Biorad mini-transfer system. A Hewlett Packard G1005A protein sequencer was used to sequence the initial amino acids of selected bands from the PVDF membrane using standard procedures (Alberta Peptide Institute, Edmonton, Canada). Table 2 and FIG. 5 show the results from this assay which indicate that other proteins, including malate dehydrogenase, ATP synthase r subunit, and OSC, are also present in all ischemic tissue samples. Further, cellular proteins such as myofilament proteins and others such as triose phosphate isomerase (FIG. 3) are present in the effluent.

HPLC Analysis of Effluent

Figure 2:
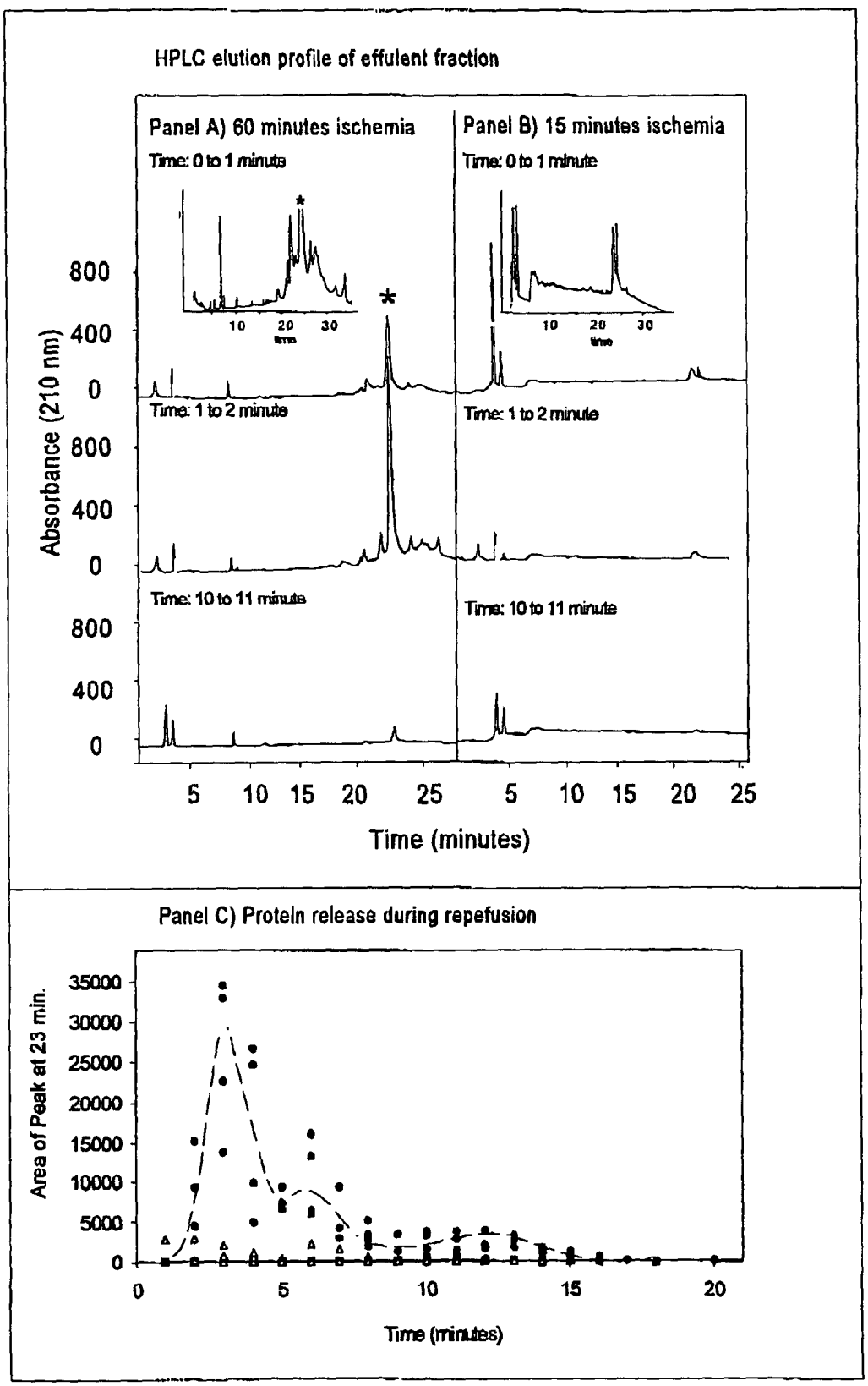
FIG. 2 shows the results of a reversed-phase high performance liquid chromatographic (RP-HPLC) analysis of proteins present in the reperfusion effluent following release from the isolated rat heart. Depicted are the RP-HPLC elution profiles of one minute fractions of the reperfusion effluent obtained from hearts which had experienced 15 min equilibration and either 15 min ischemia (panel A) or 60 min ischemia (panel B). Shown are elution profiles of one minute fractions collected at zero (top), 1 (middle) and 10 (bottom) min during reperfusion (−50 to 800 milliabsorbance units at 210 nm). Fractions were run on an analytical C8 reversed-phase column and proteins eluted using linear 2% AB gradient where buffer A was 0.05% aqueous TFA and buffer B was 0.05% TFA in acetonitrile. The insert shows enlarged scale (−20 to 200 milliabsorbance units) of the elution profile of the initial one minute fraction following 60 min ischemia. Injection peak occurs at 6 min and the peak eluted at 23 min (*) was integrated to determine its peak area. The peak area reflects the amount of protein present in the effluent at that time point. Each fraction (one minute fractions were collected for 10 min and three minute fractions for remaining 35 min) were analyzed by HPLC and the area of the peak eluted at 23 min was determined for each fraction. Panel C shows the area of the peak eluted at 23 min for each fraction collected during the reperfusion. Circles represent the proteins eluted into the effluent following 60 min of ischemia, triangles following 15 min of ischemia and squares (control) during perfusion with no ischemia. Data represent 4 to 6 rats used in each experimental protocol.

The lyophilized effluent fractions from isolated rat hearts were dissolved in 1 ml of water for every min of perfusion. HPLC analysis of the effluent was performed on an analytical Zorbax C8 300SB reversed-phase column (4.6 mm I.D.×250 mm). The HPLC system consisted of a Hewlett Packard series 1090 LC coupled to a Hewlett Packard Vectra 486 166 MHz XM processor or Varian HPLC system comprising a 9100 autosampler, a 9012 solvent delivery system, and a 9065 polychromatograph. The proteins were eluted using an A/B buffer system. Buffer A was composed of 0.05% trifluoroacetic acid and buffer B of 0.05% trifluoroacetic acid in acetonitrile. The gradient consisted of an isocratic hold (100% A) for 5 min followed by a 2% B linear gradient at 1 ml/min. The proteins and protein fragments were monitored at an optical density of 210 nm or 278 nm. The quantity of protein present in each effluent fraction was estimated by determining the area of the peak eluted at 23 min. We have previously shown that peak area is directly related to the quantity of protein present (see Van Eyk et al. 1997, *J. Biol. Chem.* 272:10529-37). This method of quantification assumes that the same protein(s) is eluted at 23 min in the various effluent fractions from the different protocols. FIG. 2 shows representative protein elution profiles of these fractions for the 0, 1 and 10 min samples following 60 (panel A) or 15 (panel B) min of ischemia. The inset shows an enlarged scale of the 0 to 1 min fraction. These results indicate that, compared to 15 min ischemia, the 60 min ischemic episode resulted in release of many more different proteins and protein fragments. These results indicate that loss of cellular membrane integrity occurs after 15 min ischemia.

Determination of the Site of Modification in Troponin I

To identify the site of modification in troponin I, specific antibodies to the amino- and carboxyl-termini of troponin I were used to find out which antibodies bind to the different modification products. The antibodies MAb 10F2 (recognizes residues 188 to 199 (SEQ ID NO:39)) and MAb 3350 (2F6.6) (recognizes residues 28 to 54 (SEQ ID NO:46)) were used (Van Eyk et al. 1998, *Circ. Res.* 82:261-71). The various modification products were run on either a 12% SDS-PAGE or 10% T-PAGE (described in Schagger et al. 1987, *Analytical Biochemistry,* 166:368-79). The proteins were transferred to nitrocellulose using a 10 mM CAPS buffer pH 11.0 for 16 h at 27 V (described in Towbin et al. 1979, *PNAS* 76:4350-54). The carboxyl-terminus is usually the first to be clipped (FIG. 7), yielding residues 1 to 193 (rat sequence, SEQ ID NO:20; corresponding human sequence, SEQ ID NO:21) (FIG. 9), but in addition there are further modifications occurring at the amino-terminus with more severe ischemia (FIG. 9). Further TnI degradation products were identified as listed in Table 4.

Isolation and Identification of Modified TnI Products

Approximately 10 mg of left ventricle from 2 hearts was homogenized in 20 mmol/l Tris-HCl pH 7.4, 6 mol/l urea, 200 mmol/l potassium chloride, with a protease inhibitor cocktail (described above) which was used throughout subsequent experiments. Tissue homogenates were sequentially dialyzed against 2 mol/l urea, 1 mol/l potassium chloride, 1 mmol/l dithiothreitol (DTT), 20 mmol/l Tris-HCl pH 7.4, with decreasing concentration of potassium chloride from 1 mol/l to 500 mmol/l and 200 mmol/l. In the final two dialysis steps, DTT was not added, but samples were maintained in reduced form with nitrogen gas bubbled through the dialysis buffer. Samples were then centrifuged at 15,000 rpm for 10 min at room temperature. Total protein concentrations of tissue homogenates and effluents were determined prior to further analysis by the Lowry assay (Lowry et al. 1964).

Affinity Chromatography

Cardiac TnC was crosslinked to 3M Emphaze Resin (Pharmacia) according to the manufacturer's protocol. The anti-TnI MAb 8I-7 (Spectral Diagnostics) (epitope residues 137 to 148 (SEQ ID NO:47)) was crosslinked to CNBr Sepharose (Pharmacia) according to the manufacturer's protocol. Both columns were equilibrated in 20 mmol/l Tris-HCl pH 7.4, 50 mmol/l potassium chloride, 1 mmol/l calcium chloride. Tissue homogenates were loaded onto the column (10 mg), and washed with 10 column volumes of buffer. Bound proteins were eluted with 65 mmol/l glycine-HCl, pH 3.1. Fractions of 1 ml were collected into tubes containing 0.86 mol/l 3-N-morpholino promane-sulfonic acid, pH 8.0 to neutralize pH. The lyophilized fractions were resuspended in 0.05% aqueous trifluoroacetic acid, and analyzed by reversed phase high performance liquid chromatography (RP-HPLC), on an analytical Zorbax C8 300SB reversed-phase column (4.6-mm internal diameter×250 mm, Chromagraphic Specialists Inc). The HPLC system consisted of a Varian 9100 Autosampler, 9012 Solvent Delivery System, and 9065 Polychrom (Varian, Mississauga, Canada). The proteins were eluted using an AB solvent system, where solvent A was composed of 0.05% aqueous trifluoroacetic acid, and solvent B was composed of 0.05% trifluoroacetic acid in acetonitrile. The AB gradient consisted of an isocratic hold (100% buffer A) for 5 minutes followed by a 2% buffer B/min linear gradient at a flow rate of 1 ml/min. The peaks were collected, lyophilized, and analyzed by mass spectrometry, western blotting, and amino acid microsequencing.

Traces from RP-HPLC and mass spectrometry analyses are shown in FIGS. 9 and 10. Panel B of FIG. 9 shows the single peak obtained from electrospray mass spectrometry of the RP-HPLC peak shown in panel A, isolated from TnC by affinity chromatography. Analysis of the rat cardiac (rc) TnI amino acid sequence identified a single sequence of appropriate mass, rcTnI residues 1 to 193 (rat sequence, SEQ ID NO:20; corresponding human sequence, SEQ ID NO:21) (see Table 4) (intact rcTnI has 210 amino acid residues, see FIG. 17B).

Mass Spectrometry

Approximately 2 mg of each lyophilized RP-HPLC peak from the affinity columns was analysed by electrospray (Fisons VG Quattro) or matrix assisted laser desorption/ionization mass spectrometry (Kratos). The masses of fractions isolated by MAb 8I-7 affinity chromatography are listed in Table 4. From these masses, TnI, TnC, and TnT fragments were determined using the SwissProt protein database and the PeptideMass tool from the world wide web molecular biology server of the Swiss Institute of Bioinformatics at http://expasy.hcuge.ch/. Protein sequence from rat cardiac TnI, mouse cardiac TnC, and rat cardiac TnT were sequentially clipped from the amino and carboxy termini until a match to the observed mono-isotopic mass was found. Masses and sequences of the TnC and TnT components of the high molecular weight complexes were determined by considering all amino acid sequences which conformed to the necessary restrictions, as described in McDonough et al. 1998 (*Biophysical J.* 74:A354).

Identification of the 32 kDa HPLC Peak (Covalent Complex)

The 32 kDa peak was not dissociated to lower molecular weight components by any of the following procedures: standard reverse phase HPLC; dissolving in 8 M urea, 1 mM DTT, 1 mM EGTA and incubating at 37° C. for 30 min; subjecting to 50% acetonitrile 0.05% trifluoroacetic acid; urea SDS-PAGE; and T-PAGE analysis (which includes urea) in the presence of DTT. Accordingly, it was concluded to be a covalent complex of proteins and/or protein fragments. In order to identify the components of the 32 kDa complex, fractions collected from MAb 8I-7 affinity chromatography were first subjected to HPLC. The resulting fractions were subjected to several different types of analysis. (A) SDS-PAGE analysis followed by a western blot analysis were performed, using TnI-specific antibodies and TnT-specific antibodies (FIG. 10). (B) Alkaline urea gels were run to detect TnC complexes. That is, only TnC, or complexes containing TnC or a fragment thereof were expected to be able to enter the alkaline urea gels, as TnC is acidic, whereas the other possible component proteins are basic and not able to enter alkaline urea gels. (C) Putative amino acid composition of the complexes (see Table 4) were deduced based on mass determined by mass spectrometry (see below).

Similarly, the high molecular weight complex (66 kDa, Table 4) is expected to include two or three proteins or protein fragments with covalent linkage(s) therebetween. Similar analytical methods to those employed above for the 32 kDa complex are utilized.

II. Isolated Rat Diaphragm

Tissue Preparation

Male Sprague-Dawley rats (200 to 250 g) were decapitated. The costal diaphragm with the phrenic nerve and adjacent rib sections was removed in <5 min and placed in a dissection tray filled with cold modified Krebs solution with the following composition (in mM): 135 NaCl, 5 KCl, 2.5 $CaCl_2$, 1 $MgSO_4$, 1 $NaH_2PO_4$, 15 $NaHCO_3$, and 11 glucose, pH adjusted to ~7.4. A strip of muscle (~5 mm wide) from the rib to the central tendon and containing the phrenic nerve was dissected from each hemidiaphragm. A silk thread was looped through the central tendon. The muscle with attached nerve was fixed in a water-jacketed organ bath (~8 ml) by clamping a metal clip over the rib. Each muscle strip was suspended vertically with the silk thread looped over a hooked metal rod attached to a stain gauge which was, in turn, fixed in a stereotaxic holder controlled with a micrometer so that the resting length of the muscle could be adjusted. The tissue was superperfused at 16 ml/min with 37° C. Krebs solution continuously aerated with 95% $O_2$-5% $CO_2$ (carbogen).

To stimulate the nerve, a suction electrode was constructed and used as follows: a glass pipette was heated and pulled to a fine point. The tip was then broken to a diameter which would just accommodate the phrenic nerve. A silver wire was inserted into the barrel of the electrode which was then inserted into a microelectrode holder to which tubing was attached so that suction could be applied to the electrode. A wire connected to the anode of a stimulus isolation unit (Grass SIU-5 driven by a Grass S88 stimulator) was also attached to the metal connector on the holder. The return path to the cathode of the isolation unit consisted of a second wire wrapped around the suction electrode. The suction electrode was lowered into the bath with the tip close to the phrenic nerve. Modest suction applied to the electrode through the attached tubing was sufficient to pull the nerve into the pipette. The nerve was stimulated with single pulses of 200 μs width at a frequency of 0.5 Hz to determine the threshold for eliciting a just-detectable twitch. Approximately 5 times this intensity was used for subsequent (supramaximal) stimulation. Muscle length was adjusted with the micrometer to obtain maximal twitch tension when stimulated with supramaximal pulses.

The output of the transducer was amplified and recorded on paper (Gould TA2000) and on tape after pulse-code modulation (NeuroCorder DR886). The transducer was calibrated by attaching to it weights of known mass.

Experimental Protocol

After a 15 min equilibration period, we stimulated the preparation with supramaximal pulses at 0.1 Hz for 3 min; diaphragmatic strips exhibiting variations in peak tension >5% were discarded. Partial pressures of $O_2$ and $CO_2$ and the pH of both the perfusate and the effluent were measured (Radiometer ABL-30). After this baseline period, we applied a fatiguing stimulation protocol to the left hemidiaphragm which consisted of 1 train/s, each 330 ms duration train having 7 pulses delivered at 20 Hz.

The right (control) hemidiaphragm was prepared identically but not subjected to the fatiguing stimulation protocol. Instead, single shocks were administered at 15 min intervals, the stability of twitch amplitude (compared to control) indicating continuing viability and stability of the preparation. Samples of the effluent (8 ml) were obtained during the 3 min baseline period and at various times after the onset of the fatiguing stimulus protocol (30 s and 2, 4, 6, 30, and 60 min). After 1 h, tissue samples were removed, frozen in liquid $N_2$, and stored at $-70°$ C. along with all samples of effluent.

Tissue Sample Preparation

Frozen tissue samples were homogenized in 25 mM Tris, pH 7.5, plus a cocktail of protease inhibitors consisting of 50 μM phenylmethylsulfonyl fluoride, 3.6 μM leupeptin, 2.1 μM pepstatin A and 10 mM EDTA. Samples were stored at $-70°$ C. for later HPLC, SDS-PAGE and western blot analysis.

SDS-PAGE: The protein content of the homogenate was determined using the Lowry assay. Protein samples were then prepared in Laemmli buffer (1% (w/v) SDS, 2.5 mM Tris, pH 6.5, 10% (w/v) sucrose, 0.025% (w/v) bromophenol blue) and DTT (1 mM) at a total protein concentration of 1 mg/ml before being stored at $-70°$ C.

HPLC: see above (cardiac tissue extract preparation).

Effluent Sample Preparation

Samples were thawed and aliquots (8 ml) were dialyzed against double-distilled water mixed with DTT and HCl (both 1 mM) in dialysis tubing (Fisherbrand, nominal molecular weight cut-off of 6,000 to 8,000). Following dialysis, samples were lyophilized.

SDS-PAGE: Samples were re-suspended in double-distilled water and mixed with Laemmli buffer and DTT. All samples were stored at $-20°$ C. for later analysis.

HPLC: see above (cardiac effluent preparation).

SDS-PAGE and Western Blot Analysis

These were carried out according to the methods set forth for rat cardiac tissue, above.

As shown in FIG. 11, fatiguing contraction of the in vitro rat diaphragm resulted in the appearance in the effluent (E) of two products of TnI, a degradation product at ~17 kDa and a complex at ~66 kDa. The slow and fast isoforms of TnI were identified using the feline soleus (SO) and caudofemoralis (CF), a slow and fast muscle, respectively. TnI, intact and degraded, was visualized using the MAb C5.

Figure 12B:
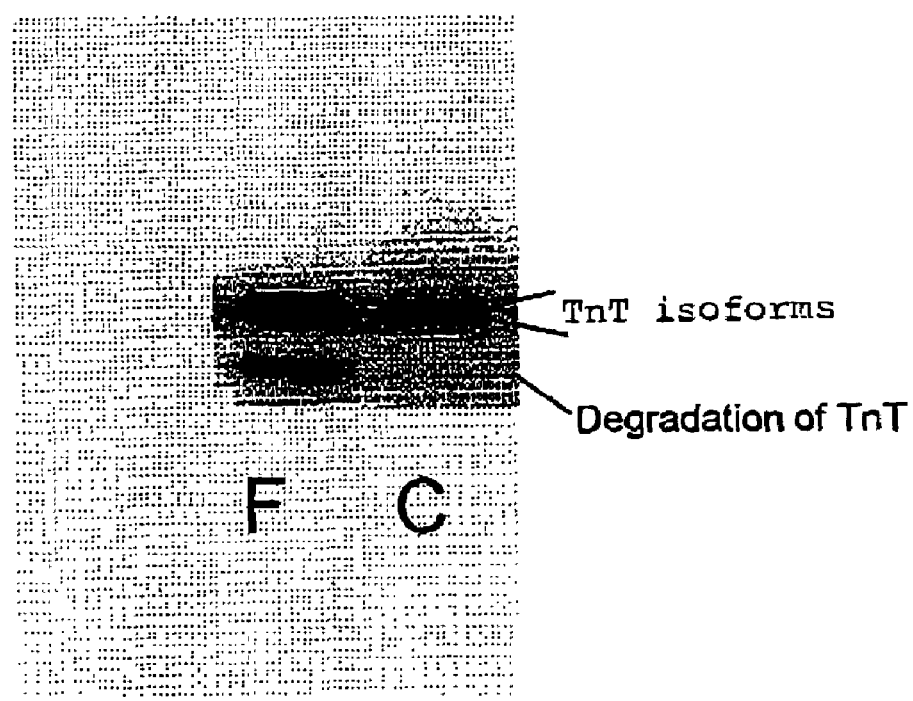

FIG. 12A shows detection in rat diaphragm of TnI before (control, C) and following (F) stimulation using the MAb C5. In both conditions, a 17 kDa modification product was present; a 21 kDa modification product was also present following stimulation. Similarly, FIG. 12B shows detection of skeletal TnT in the in vitro rat diaphragm before (C) and following (F) stimulation using the anti-TnT MAb JLT-12. TnT modification was present only after stimulation.

III. Hypoxemia in Canine Skeletal Muscle

Experiments were conducted according to procedures established by the Canadian Council on Animal Care and after approval by the Animal Care Committee of Queen's University. Six mongrel dogs of either sex (2 males, 4 females; weight 16 to 24.4 kg, mean 19.8 kg) were anaesthetized with an intravenous injection of pentobarbital sodium, 35 mg/kg, supplemented when necessary if the animals displayed a brisk response to noxious stimulation of a toe pad or blinked in response to stimulation of the cornea. Surgical procedures included insertion of an endotracheal tube to which a heat and moisture exchanger was attached, a venous 'butterfly' cannula into a leg vein for administration of supplemental anaesthetic, and a cannula into the carotid artery for measurement of arterial blood pressure and withdrawal of blood for measurements of arterial blood gases. The right jugular vein was dissected and two Swan-Ganz catheters were inserted into the right heart, one into the pulmonary artery and the other into the right atrium. Both placements were made according to measurements of pressure at the tip of the catheter. The former was used for sampling mixed venous blood and both were used for thermal dilution measurements of cardiac output when cold saline was injected into the latter (Edwards 9520 Cardiac Output Computer).

Tissue Samples

Control biopsies were taken at the start of the experiment before imposition of hypoxemia from the following muscles: quadriceps (Q), external oblique (EO), and internal oblique (IO). To gain access to the IO, the aponeurosis of the overlying EO was incised and the muscle reflected laterally. After taking the biopsy, we attempted to stop bleeding using cautery and by packing the site of the biopsy with oxycellulose and/or gelfoam but, by the end of the experiment, most sites had started to bleed again. At the end of the experiment, when all dogs decreased respiratory frequency (f) in response to severe hypoxemia, the dogs were immediately placed on mechanical ventilation and samples taken from Q, EO and IO as well as the transverse abdominis (TA), costal and crural diaphragm, and caudal (intercostal space 9-10) and mid-thoracic (interspace 4-6) external and internal intercostals. Most samples were taken before the heart stopped and all were obtained within 5 min after death.

All tissue samples were excised and quickly washed in cold (4° C.) saline before being frozen in liquid $N_2$ and stored at $-70°$ C. until prepared for SDS-PAGE analysis. Frozen tissue samples were homogenized in 25 mM Tris, pH 7.5, plus a cocktail of protease inhibitors (50 M phenylmethylsulfonyl fluoride, 3.6 M leupeptin, 2.1 M pepstatin A, and 10 mM EDTA). The protein contents of the homogenates were determined using Lowry assay. Protein samples were then prepared in Laemmli buffer (1% (w/v) SDS, 2.5 mM Tris, pH 6.5, 10% (w/v) sucrose, 0.025% (w/v) bromophenol blue) and 1 mM dithiothreitol at a total protein concentration of 1 mg/ml before being stored at $-20°$ C. for later SDS-PAGE and western immunoblot analysis.

Electromyographic Recording (EMGs)

After biopsies had been taken, pairs of fine wires, insulated except for the tips which were bent back over the outside of 23 gauge needles, were inserted under direct visual observation approximately 15 mm apart into the IO on the side opposite to that from which the biopsy had been made. The needles were then withdrawn, leaving the wires in place. A piece of Parafilm was placed over the electrodes. Similar electrodes were placed into the ipsilateral EO. The overlying skin was then closed with clips. Recordings of the diaphragmatic EMG were made by inserting identical electrodes percutaneously at the sixth or seventh right interspace. All signals were amplified and filtered (Grass P511J), the signals being recorded on video tape after pulse code modulation (NeuroCorder DR886) and recorded on paper (Gould TA2000), either as raw signals or after 'integration' (Paynter filter, time constant 100ms).

Hypoxia

Severe "isocapnic" hypoxemia was introduced by having the dogs breathe two gas mixtures using a new technique which prevents the hypocapnia typically associated with inhalation of hypoxic gas mixtures, regardless of the hyperpnea induced by the hypoxia (Sommer et al., *Eur. Respir. J.* in press). In brief, the dogs breathed a gas mixture of 9.5% $O_2$, balance $N_2$ fed at a rate of 2 l/min to a balloon attached to a one-way valve on the inspiratory side of the breathing circuit. The remaining gas inspired by the dogs during the hypoxia-induced increase in ventilation came from a cylinder containing 9.5% $O_2$, 6.5% $CO_2$, balance $N_2$ and connected to a demand valve (US Divers). Thus, any hypoxia-induced ventilation greater than the basal flow provided by the first cylinder was met from the second which, because of its $CO_2$ content, prevented hypocapnia.

Protocol

Two sets of control measurements, 20 min apart, were taken of arterial and mixed venous blood gases and pH (ABL 30) and cardiac output. The dogs were then placed on the breathing circuit. Once the $PaO_2$ had fallen to the desired range (24 to 28 mmHg), measurements were repeated at 20 min intervals until the dogs died. Death was always preceded by a sudden slowing of respiratory frequency, at which time the dog was placed on mechanical ventilation with room air and biopsies taken as described above.

SDS-PAGE and Western Blot Analysis

These were carried out according to the methods set forth for rat cardiac tissue, above.

Western blots of skeletal TnI (using the MAb C5 which identifies both intact isoforms) in canine respiratory muscles (internal oblique, IO; costal diaphragm, Dco; and crural diaphragm, Dcr) before (control) and following 2 to 3 h of severe hypoxemia (hypoxic; arterial $PO_2$~25 mmHg) are shown in FIG. 13A. Hypoxemia caused modification of TnI only in the costal and crural diaphragms.

FIG. 13B shows western blots of skeletal TnI in samples of canine tissues using the MAb 8I-7. Feline caudofemoralis (CF, a fast muscle) and soleus (SO, a slow muscle) were used to identify the fast and slow isoforms of TnI. Hypoxemia resulted in the appearance of several modified forms of TnI in the crural diaphragm (Dcr) and external oblique (EO).

IV. Analysis of Canine Urine

Urine Collection

Urine was collected from: (1) 8 mongrel dogs of either sex, via catheterization, before, during severe hypoxemia, and after cessation of respiration; (2) voided samples from 5 male pigs before and for two weeks following acute myocardial injury (ligation of a coronary artery). Prior to analysis, urine samples were tested for the presence of blood; samples containing blood were discarded. Samples were frozen immediately after collection and stored at $-20°$ C.

Urine samples were thawed and aliquots (10 ml) dialyzed against double-distilled water with 1 mM HCl and 1 mM DTT in dialysis tubing (Fisherbrand, nominal molecular weight cut-off of 6,000 to 8,000) with two exchanges of 5 l each per 5 aliquot samples. Following dialysis, samples were lyophilized. For SDS-PAGE analysis, samples were re-suspended in double-distilled water and mixed with DTT (to yield a final concentration of 1 mM) and Laemmli buffer. Samples for HPLC analysis were resuspended in 0.05% TFA. All samples were stored at $-20°$ C. for later HPLC, SDS-PAGE and western blot analysis.

Urine samples were also spun in a Centricon-10 clinical centrifuge (sieve 10 kDa) at 5,000 rpm for 1 h, before being lyophilized and re-suspended in 0.05% TFA and used for HPLC analysis.

SDS-PAGE and Western Blot Analysis

These were carried out according to the methods set forth for rat cardiac tissue, above.

In the western blots shown in FIG. 14, several modified forms of TnI can be seen in canine urine of hypoxic dogs.

HPLC Analysis of Urine

Protein samples were loaded on reverse phase HPLC. Two different protocols were used: 1) At a flow of 1.00 ml/min, after a 20 min equilibration time with 0.05% TFA, we applied a gradient of 0.71%/min $CH_3CN$ up to 50% followed by a 3%/min $CH_3CN$ gradient up to 80%. 2) At a flow of 0.25 ml/min, after a 20 min equilibration time with 0.05% TFA, we applied a gradient of 0.233%/min $CH_3CN$ from 7% to 28% followed by a 5.2%/min $CH_3CN$ gradient up to 80%.

As shown in the results of the HPLC analysis (FIG. 15), the additional peaks in the urine of a hypoxic dog (top trace), relative to that of a normoxic dog (bottom trace), indicates the presence of additional proteins in urine of the hypoxic dog.

V. Human Cardiac Tissue

Human left and right ventricular tissue biopsy samples were taken from coronary artery bypass patients before cardioplegia, and 10 min after reperfusion (removal of the cross-clamp). The samples were immediately frozen in liquid nitrogen, and stored at $-70°$ C. until analysis. Samples were homogenized in buffer containing 6 mol/l urea, 20 mmol/l Tris-HCl pH 8.8, with a protease inhibitor cocktail (as described above). Samples were then diluted 2-fold in sample buffer containing 6 mol/l urea, 100 mmol/l β-ME, 20 mmol/l Tris-HCl pH 6.8, 0.05% bromophenol blue. The samples were separated by 12.5% SDS-PAGE, and transferred to nitrocellulose with a wet transfer apparatus (Bio-rad) in 124 mmol/l glycine, 25 mmol/l Tris-HCl, pH 8.2, 20% methanol. Western blots were performed as described above.

Data from two patients are shown in FIG. 16, wherein it can be seen that with both patients, there is formation of a TnI high molecular weight complex (~60 kDa) and some TnI modification in left ventricular following bypass surgery. Under these conditions, there is no TnI or CKMB present in the blood, indicating that little or no necrosis occurred during surgery (data not shown).

Equivalents

Those skilled in the art will recognize, or be able to ascertain using no more than routine experimentation, many equivalents to the specific embodiments of the invention described herein. Such equivalents are intended to be encompassed by the following claims.

TABLE 1

Function and protein content of left ventricle tissue from rat hearts subjected to ischemia and ischemia/reperfusion

| Experimental Protocol[a] | | Skinned Fiber Experiment[b] | | Quantity of Protein Present in Tissue[c] | | | | | | Quantity of Protein in Effluent[d] |
|---|---|---|---|---|---|---|---|---|---|---|
| ischemia (minutes) | reperfusion (minutes) | $pCa_{50}$ | maximum force (mg/mg) | Troponin I | α-actinin | TM | MCL1 | OSC protein[f] | MLC2 | relative peak area at 23 min |
| 1) 0 | 45[e] | 5.82 ± 0.01 | 5190 ± 72 | 0.28 ± 0.05 | 0.16 ± 0.01 | 0.29 ± 0.05 | 0.13 ± 0.03 | ND | 0.11 ± 0.02 | – |
| 2) 15 | 0 | 5.92 ± 0.01 | 5830 ± 21 | 0.28 ± 0.02 | 0.17 ± 0.02 | 0.24 ± 0.01 | 0.13 ± 0.01 | ND | 0.05 ± 0.01 | NA |
| 3) 15 | 45 | 5.93 ± 0.02 | 2790 ± 36 | 0.37 ± 0.02 | 0.10 ± 0.04 | 0.24 ± 0.01 | 0.18 ± 0.01 | 0.05 ± 0.01 | 0.09 ± 0.01 | + |
| 4) 60 | 0 | 5.86 ± 0.02 | 2860 ± 52 | 0.33 ± 0.03 | 0.12 ± 0.91 | 0.24 ± 0.03 | 0.23 ± 0.05 | 0.05 ± 0.01 | 0.10 ± 0.03 | NA |
| 5) 60 | 45 | 6.03 ± 0.01 | 1670 ± 12 | 0.51 ± 0.07 | 0.10 ± 0.02 | 0.29 ± 0.02 | 0.30 ± 0.4 | 0.09 ± 0.02 | 0.19 ± 0.05 | +++ |

[a]All rat hearts underwent 15 minutes of equilibration prior to starting the experimental protocol. When required, isoproterenol was added to the perfusated during the final 5 minutes of the equilibrium period.
[b]The $pC_{50}$(–log concentration of calcium required to induce half of the $Ca^{2+}$-dependent change in force) and maximum force (mg/mg) was determined from curve fitting the data in FIG. 1. Force produced by a skinned fiber (mg) per total protein content of the corresponding skinned fiber (mg) with respect to changing calcium concentrations is plotted. This quantifies the amount of force exhibited by each fiber taking into account the size of the fiber.
[c]Quantity of TnI and α-actinin determined from densiometry measurements (±STD) from 12.5% SDS-PAGE. ND = not detected
[d]The quantity of protein present in the effluent was assigned a grading system (+++ most, ++ intermediate and + least) based on HPLC analysis of effluent samples. NA stands for not applicable, protocols were reperfusion was not done.
[e]Control conditions which are 0 minutes ischemia followed by 45 minutes perfusion.
[f]OSC = ATP synthase oligomycin sensitivity conferring protein.

TABLE 2

Identification of proteins affected by ischemia and ischemia/reperfusion by amino acid sequencing

| Amino Acid Sequence | Protein | Residue Number | First Identified Amino Acid (pmole) | Tissue Sampled |
|---|---|---|---|---|
| XXKKPE(P/A)KADDA (SEQ ID NO: 1) | myosin light chain 1 | 1-12 | 2.6 | global ischemia myofibrils & 60I/45RP tissue |
| XPAPAAAPAAAP (SEQ ID NO: 2) | myosin light chain 1 | 20-31 | 6.0 | global ischemia myofibrils |
| XKVALGAXGGI (SEQ ID NO: 3) | malate dehydrogenase | 1-11 | 3.2 | 60I/45 RP tissue |
| XXLKDITRRLKSI (SEQ ID NO: 4) | ATP g synthase chain | 1-13 | 4.5 | 60I/45 RP tissue |
| XXKLVRPPVQ (SEQ ID NO: 5) | ATP synthase oligomycin conferring protein | 1-10 | 2.3 | 60I/45 RP tissue |
| XAHKSEIAHR (SEQ ID NO: 6) | serum albumin | 1-10 | 12.4 | 60I/45 RP effluent |
| XPS(R/L)KFFVGGN (SEQ ID NO: 7) | triose phosphate isomerase | 1-11 | 9.9 | 60I/45 RP effluent |

TABLE 3

Progressive Alteration of TnI with Increasing Severity of Ischemia.

| Ischemia/Reperfusion Induced TnI Product | | A. Left Ventricle Tissue Percentage of Total TnI* | | | B. Anti-TnI Affinity Chromatography Percentage of Total TnI[†] | |
|---|---|---|---|---|---|---|
| | | 0/45[‡] | 15/45 | 60/45 | Peak 2 | Peak 3 |
| Covalent Complexes[§] | | 0 | 16.9% | 3.1% | N/D[//] | N/D |
| rcTnI | | 94.4% | 52.2% | 35.3% | 71.7% | 91.4% |
| rcTnI Degradation Products | ~22 kDa | 5.6% | 24.1% | 21.3% | 25.5% | 6.4% |
| | ~16 kDa | 0 | 0 | 15.1% | 2.8% | 2.2% |
| | ~15 kDa | 0 | 0 | 17.2% | N/D | N/D |

*The ischemia/reperfusion-induced modified TnI products observed in urea T-PAGE separated left ventricular tissue which underwent either 0/45, 15/45, or 60/45 (FIG. 8) were quantified from 8I-7 MAb Western blots (FIG. 8A). The quantity of each TnI component was determined as a percentage of the total TnI (intact and modified) present in each tissue sample. Only those products which are positively identified in Table 4 are included here, identified by their apparent molecular weight (FIG. 8A).
[†]The ischemia/reperfusion-induced modified TnI products observed from 8I-7 MAb affinity chromatography of 60/45 left ventricular tissue (FIG. 10) were quantified from 8I-7 MAb Western blots (FIG. 10B), and the amount of each TnI component determined as a percentage of the total in each sample.
[‡]Control tissue, which experienced no ischemic episode, but 45 minutes of reperfusion.
[§]The quantity of the two TnI-containing covalent complexes combined.
[//]Quantities less than 2% of total TnI could not be accurately determined.

TABLE 4

Identification of Ischemia-Induced TnI Products by Mass Spectrometry.

| Ischemia/Reperfusion-Induced TnI Product[a] | | Source[¶] | Immunoreactivity with MAb's[†] | | | | Alk. Urea PAGE[‡] | Putative Identification[§] | Observed Mass (Da ± S.E.) | Theoretical Mass (Da)[//] |
|---|---|---|---|---|---|---|---|---|---|---|
| | | | 8I-7 | 3I-35 | AM-IN | TnT | | | | |
| Covalent Complexes | ~66 kDa | peak 3 | + | ± | + | + | − | rcTnI(1-193)/ TnT(191-298) | 32 872 ± 9[#] | 32 871 |
| | ~55 kDa | peak 2 | + | ± | + | − | + | rcTnI(1-193)/ TnC(1-94) | 32 734 ± 14[#] | 32 730 |
| rcTnI Degradation Products | ~22 kDa | peak 2 | + | ± | + | − | − | rcTnI 1-193 | 22 144 ± 8[§] | 22 148 |
| | ~16 kDa | peak 2 | + | ± | ± | − | − | rcTnI 63-193 | 15 348 ± 15** | 15 337 |
| | ~15 kDa | peak 2 | + | − | − | − | − | rcTnI 73-193 | 14 130**,[††] | 14 096 |

[a]TnI products identified by their apparent molecular weights (FIG. 8A).
[†]Immunological analysis (Western blots, FIGS. 8A, 10C) of protein products bound to Mabs: strong (+), weak (±), or no binding (−).
[‡]Electrophoretic mobility in alkaline urea PAGE (FIG. 10): mobile (+, TnC containing), non-mobile (−, not containing TnC).
[§]The amino acid sequence(s) of proteins which are the theoretical best match to the observed masses.
[//]Best match to the observed masses was determined by calculating the mass of rcTnI, rcTnT, and mouse cTnC, sequentially clipped from the N- and C-termini using the PeptideMass tool from the Swiss Institute for Bioinformatics website.
[¶]The source of the TnI products indicates the peak from RP-HPLC analyzed 8I-7 affinity column fractions of 60/45 tissue (FIG 4).
[#]Mass determined by electrospray mass spectrometry.
**Mass determined by matrix assisted laser desorption/ionization mass spectrometry.
[††]The difference between the observed and theoretical masses is equal to that of a sodium ion (MW 35 Da), which is commonly found associated with mass spectrometrically analyzed proteins (as a result of the ionization process).

We claim:

1. A method for assessing skeletal muscle damage in a subject, comprising detecting the presence or absence or measuring the amount of:
   (a) a peptide fragment of a myofilament protein; or
   (b) a covalent or non-covalent complex of at least:
      (i) a peptide fragment of a myofilament protein and an intact myofilament protein; or
      (ii) two peptide fragments of myofilament proteins,
   in a biological sample obtained from a subject being assessed for skeletal muscle damage, said biological sample being selected from the group consisting of skeletal muscle tissue, a component of skeletal muscle tissue, blood, blood serum and urine, by incubating the biological sample with an antibody or antigen specific fragment thereof that specifically binds to the peptide fragment of a myofilament protein under conditions which allow the antibody or antigen specific fragment thereof to form a complex with the
   (a) peptide fragment of a myofilament protein; or
   (b) covalent or non-covalent complex of at least:
      (i) a peptide fragment of a myofilament protein and an intact myofilament protein; or
      (ii) two peptide fragments or myofilament proteins,
   and detecting or measuring the formed complex, wherein said peptide fragment of the myofilament protein or said peptide fragment of the covalent or non-covalent complex formation consists of:
   a skeletal troponin I peptide fragment, or
   a skeletal troponin T peptide fragment,
   and wherein the presence or amount of:
   (a) the peptide fragment of the myofilament protein; or
   (b) the covalent or non-covalent complex of at least:
      (i) the peptide fragment of the myofilament protein and the intact myofilament protein; or
      (ii) two peptide fragments of myofilament proteins,
   in the biological sample is associated with skeletal muscle damage.

2. The method of claim 1, wherein the peptide fragment of the myofilament protein or the covalent or non-covalent complex of at least:
   (i) a peptide fragment of a myofilament protein and an intact myofilament protein; or
   (ii) two peptide fragments of myofilament proteins consists of a covalent complex.

3. The method of claim 1 wherein the presence of at least two different peptide fragments of myofilament proteins or covalent or non-covalent complexes is detected.

4. The method of claim 1 wherein the amounts of at least two different peptide fragments of myofilament proteins or covalent or non-covalent complexes are measured and the measured amounts are compared as an indication of the extent of skeletal muscle damage in the subject.

5. The method of claim 1 wherein the ratio of at least two different peptide fragments of myofilament proteins or covalent or non-covalent complexes is assessed as an indication of the extent of skeletal muscle damage in the subject.

6. The method of claim 1, wherein the complex is detected or measured by assaying for the presence of a label.

7. The method of claim 1, wherein the antibody or functional fragment of the antibody is labeled with an enzyme which is detected by measuring enzymatic activity associated therewith.

8. The method of claim 7, wherein the enzyme is selected from the group consisting of alkaline phosphatase, horseradish peroxidase, luciferase, beta-galactosidase, lysozyme, glucose-6-phosphate dehydrogenase, lactate dehydrogenase, and urease.

9. The method of claim 1, wherein the antibody or a functional fragment of an antibody is immobilized on a solid phase.

10. The method of claim 9, wherein the solid phase is a plastic surface.

11. The method of claim 1 wherein the skeletal muscle damage is reversible.

12. The method of claim 11 wherein the skeletal muscle damage is due to at least one condition selected from the group consisting of hypoxia, hypoxemia, ischemia, fatigue and reperfusion.

13. The method of claim 1 wherein the skeletal muscle damage is irreversible.

14. The method of claim 13 wherein the skeletal muscle damage is due to at least one condition selected from the group consisting of hypoxia, hypoxemia, ischemia, and reperfusion.

15. A method for assessing skeletal muscle damage in a subject, comprising detecting the presence or absence or measuring the amounts of at least two different:
   (a) peptide fragments of a myofilament protein
   (b) covalent or non-covalent complexes of at least:
       (i) a peptide fragment of a myofilament protein and an intact myofilament protein; or
       (ii) two peptide fragments of a myofilament protein,
in a biological sample obtained from a subject being assessed for muscle damage, said biological sample being selected from the group consisting of skeletal muscle tissue, a component of skeletal muscle tissue, blood, blood serum and urine, by incubating the biological sample with an antibody or antigen specific fragment thereof that specifically binds to the peptide fragment of a myofilament protein, under conditions which allow the antibody or antigen specific fragment thereof to form a complex with the
   (a) peptide fragment of a myofilament protein; or
   (b) covalent or non-covalent complex of at least:
       (i) a peptide fragment of a myofilament protein and an intact myofilament protein; or
       (ii) two peptide fragments of myofilament proteins,
and detecting or measuring the formed complex, wherein said peptide fragments of the myofilament protein or said peptide fragments of the covalent or non-covalent complexes consist of:
   skeletal troponin I peptide fragments, or
   skeletal troponin T peptide fragments,
wherein the presence or amount of the:
   (a) peptide fragments of the myofilament protein; or
   (b) covalent or non-covalent complexes of at least:
       (i) the peptide fragment of the myofilament protein and the intact myofilament protein; or
       (ii) two peptide fragments of the myofilament protein,
in the biological sample are associated with muscle damage, and wherein the
   (a) peptide fragments of the myofilament protein; or
   (b) covalent or non-covalent complexes of at least:
       (i) the peptide fragment of the myofilament protein and the intact myofilament protein; or
       (ii) two peptide fragments of the myofilament protein,
are from the same myofilament protein.

16. The method of claim 15 wherein the ratio of the
   (a) peptide fragments of the myofilament protein; or
   (b) covalent or non-covalent complexes of at least:
       (i) the peptide fragment of the myofilament protein and the intact myofilament protein; or
       (ii) two peptide fragments of the myofilament protein,
from the same myofilament protein is assessed as an indication of the extent of the muscle damage in the subject.

17. The method of claim 1 wherein said biological sample is skeletal muscle tissue.

18. The method of claim 1 wherein said biological sample is a component of skeletal muscle tissue.

19. The method of claim 1 wherein said biological sample is blood.

20. The method of claim 1 wherein said biological sample is blood serum.

21. The method of claim 1 wherein said biological sample is urine.

22. The method of claim 15 wherein said biological sample is skeletal muscle tissue.

23. The method of claim 15 wherein said biological sample is a component of skeletal muscle tissue.

24. The method of claim 15 wherein said biological sample is blood.

25. The method of claim 15 wherein said biological sample is blood serum.

26. The method of claim 15 wherein said biological sample is urine.

* * * * *